US006875851B1

(12) United States Patent
Travis et al.

(10) Patent No.: US 6,875,851 B1
(45) Date of Patent: Apr. 5, 2005

(54) **PROLYL TRIPEPTIDYL PEPTIDASES NUCLEIC ACID OF *PORPHYROMONAS GINGIVALIS***

(75) Inventors: James Travis, Athens, GA (US); Jan Potempa, Athens, GA (US); Agnieszka Banbula, Athens, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 09/518,550

(22) Filed: Mar. 3, 2000

Related U.S. Application Data

(60) Provisional application No. 60/123,148, filed on Mar. 5, 1999, now abandoned.

(51) Int. Cl.[7] ............................................. C01N 21/02
(52) U.S. Cl. ...................... 536/23.1; 536/23.2; 536/300; 514/44; 435/4; 435/6; 435/69.1; 435/198; 530/350
(58) Field of Search ..................... 514/44; 536/300, 536/302, 23.1; 530/350; 435/6, 198, 69.1, 4

(56) References Cited

U.S. PATENT DOCUMENTS

| | | | | |
|---|---|---|---|---|
| 4,543,329 A | * | 9/1985 | Daum et al. | 435/69.1 |
| 5,223,404 A | * | 6/1993 | Suido et al. | 435/24 |
| 5,432,055 A | * | 7/1995 | Evans et al. | 435/6 |
| 5,475,097 A | * | 12/1995 | Travis et al. | 536/23.2 |
| 5,521,081 A | * | 5/1996 | Inaoka et al. | 435/212 |
| 5,523,390 A | * | 6/1996 | Travis et al. | 536/23.2 |
| 5,824,791 A | * | 10/1998 | Progulske-Fox et al. | 536/237 |
| 5,919,690 A | * | 7/1999 | Halkier et al. | 435/208 |
| 5,976,854 A | * | 11/1999 | Jones et al. | 435/198 |
| 5,981,164 A | * | 11/1999 | Wilstrom | 435/4 |
| 6,129,917 A | * | 10/2000 | Potempa et al. | 424/184.1 |
| 6,274,718 B1 | * | 8/2001 | Travis et al. | 536/23.2 |
| 6,284,511 B1 | * | 9/2001 | Inaoka et al. | 435/212 |
| 6,444,799 B1 | * | 9/2002 | Ross | 536/23.1 |

FOREIGN PATENT DOCUMENTS

| | | | |
|---|---|---|---|
| EP | 255341 | * | 5/1998 |
| JP | 02-5580 | * | 1/1990 |
| WO | 94/23022 | * | 10/1994 |
| WO | 97/4447 | * | 11/1997 |
| WO | WO 00/52147 | | 9/2000 |

OTHER PUBLICATIONS

Martinsson et al, 1993, Genomics, vol. 17, pp. 493–495.*

Hillier et al (Genbank Accession number R11686, created date Apr. 21, 1995), (SEQ Algn. only).*

Kabashima, T et al, J. Biochemistry, vol. 120, pp. 1111–1117, 1996, Swiss–prot accession number P95782, xanthomonas maltophilia dipeptidyl peptidase IV, (sequence alignment abstract only).*

Diefenthal, T et al, Appl. Microbiol. Biotechnol. vol. 40, pp. 90–97, 1993, Cloning of proline–specific endopeptidase gene from *Flavobacterium meningosepticum*:expression in *Escherichia coli* and purification of the heterologous protein.*

(Continued)

Primary Examiner—Lynette R. F. Smith
Assistant Examiner—Ginny Allen Portner
(74) Attorney, Agent, or Firm—Mueting, Raasch & Gebhard P.A.

(57) ABSTRACT

The present invention provides isolated polypeptides, prolyl tripeptidyl-peptidases, and active analogs, active fragments or active modifications thereof, having amidolytic activity for cleavage of a peptide bond present in a target peptide having at least 30 amino acids. Isolated nucleic acid fragments encoding isolated prolyl tripeptidyl-peptidases are also provided, as are methods of reducing growth of a bacterium by inhibiting a prolyl tripeptidyl-peptidase.

3 Claims, 19 Drawing Sheets

OTHER PUBLICATIONS

Kanatani, Akio et al, Journal of Biochemistry, vol. 113, pp. 790–796, 1993, Prolyl Endopeptidase from *Aeromonas hydrophila*: Cloning, sequencing, and expression of the enzyme gene and characterization of the expressed enzyme.*

Vanhoof, G et al, Gene, vol. 149, (1994),pp. 363–366, Cloning and sequence analysis of the gene encoding human lymphocyte prolyl endopeptidase.*

Abbott et al., "Genomic organization, exact localization, and tissue expression of the human CD26 (dipeptidyl peptidase IV) gene" *Immunogenetics* (1994) *40*:331–338, accession No. U1378.

Andersen et al., "Presence and possible role of a renal brush–border Gly–Pro–X–releasing exopeptidase", *American Journal of Physiology*, 253(4 Pt 2):F648–F655 (1987).

Binnie et al., "Isolation and Characterization of Two Genes Encoding Proteases Associated with the Mycelium of *Streptomyces lividans* 66", *Journal of Bacteriology*, 177(21):6033–6040 (1995).

Renn et al., "Characterization and Cloning of Tripeptidyl Peptidase II from the Fruit Fly, *Drosophila melanogaster*", *The Journal of Biological Chemistry*, 273(30):19173–19182 (1998).

Abiko et al., "Glycylprolyl Dipeptidylaminopeptidase from *Bacteroides gingivalis*," *J. Dent. Res.*, 64(2):106–111 (1985).

Altschul et al., "Gapped BLAST and PSI–BLAST: A New Generation of Protein Database Search Programs," *Nuc. Acids Res.*, 25(17):3389–3402 (1997).

Ausubel et al., eds., *Current Protocols in Molecular Biology*, John Wiley & Sons, Inc., United States, title page, publication page and table of contents only, 12 pages (1994).

Banbula et al., "Unusual Processing of Proteins and Polypeptides During the Growth of *Porphyromonas gingivalis*: Implications of a Primary Role for Prolyl Di– and Tripeptidyl–Peptidases," *J. Dent. Res.*, 78:466, Abstract No. 2888 (May, 1999).

Banbula et al., "Unusual Processing of Proteins and Polypeptides During the Growth of *Porphyromonas gingivalis*: Implication of a Primary Role for Prolyl Di and Tripeptidyl–Peptidases," poster presentation (6 pages) at Edward H. Hatton Awards Competition, Vancouver (B.C.), Canada (Mar. 9, 1999).

Banbula et al., "Prolyl Tripeptidyl Peptidase from *Porphyromonas gingivalis*, A Novel Enzyme with Possible Pathological Implications for the Development of Periodontitis," *J. Biol. Chem.*, 274(14):9246–9252 (Apr. 2, 1999).

Banbula et al., "Emerging Family of Proline–Specific Peptidases of *Porphyromonas gingivalis*: Purification and Characterization of Serine Dipeptidyl Peptidase, a Structural and Functional Homologue of Mammalian Prolyl Dipeptidyl Peptidase IV," *Infect. Immun.*, 68(3):1176–1182 (Mar., 2000).

Barua et al., "Purification of an 80,000–$M_r$ Glycylprolyl Peptidase from *Bacteroides gingivalis*," *Infect. Immun.*, 57(8):2522–2528 (1989).

Brosius et al., "Gene Organization and Primary Structure of a Ribosomal RNA Operon from *Escherichia coli*," *J. Mol. Biol.*, *148*:107–127 (1981).

Chen et al., "Purification and Characterization of a 50–kDa Cysteine Proteinase (Gingipain) From *Porphromonas gingivalis*," *J. Biol. Chem.*, 267(26):18896–18901 (1992).

Church et al., "Genomic Sequencing," *Proc. Natl. Acad. Sci. USA*, *81*(7)1991–1995 (1984).

Dashper et al., "Amino Acid and Peptide Uptake by *Porphyromonas gingivalis*," *J. Dent. Res.*, 77(5):1133, Abstract No. 36 (1998).

Fülöp et al., "Prolyl Oligopeptidase: An Unusual Beta–Propeller Domain Regulates Proteolysis," *Cell*, 94(2):161–170 (1998).

Grenier et al., "Isolation of a Membrane–Associated *Bacteroides gingivalis*Glycylprolyl Protease," *Infect. Immun.*, 55(12):3131–3136 (1987).

Hinode et al., "Purification and Characterization of Three Types of Proteases from Culture Supernatants of *Porphyromonas gingivalis*," *Infect. Immun.*, 59(9):3060–3068 (1991).

Kabashima et al., "Cloning, Sequencing, and Expression of the Dipeptidyl Peptidase IV Gene form *Flavobacterium meningosepticum* in *Escherichia coli*," *Arch. Biochem. Biophys.*, 320(1):123–128 (1995), accession No. Q47900.

Kiyama et al., "Sequence Analysis of the *Porphyromonas gingivalis*Dipeptidyl Peptidase IV Gene," *Biochim. Biophys. Acta*, *1396*, 39–46 (1998), Mar. 4.

Kornman, "Controlled–Release Local Delivery Antimicrobials in Periodontics: Prospects for the Future," *J. Periodontol.*, 64(8):782–791 (1993).

Matsudaira, "Sequence from Picomole Quantities of Proteins Electroblotted onto Polyvinylidene Difluoride Membranes," *J. Biol. Chem.*, 262(21):10035–10038 (1987).

"MS–Fit, A peptide–mass fingerprinting tool," Ludwig Institute for Cancer Research & University College London, 2000.

Nakamura et al., "Cloning of the Gene Encoding a Glycylprolyl Aminopeptidase from *Porphyromonas gingivalis*," *Arch. Oral Biol.*, 37(10):807–812 (1992).

"Open Reading Frame Finder," National Center for Biotechnology Information (NCBI), (available on or before Mar. 3, 2000).

Potempa et al., "Host and *Porphyromonas gingivalis*Proteinases in Periodontitis: A Biochemical Model of Infection and Tissue Destruction," *Perspect. Drug Discovery Design*, *2*:445–458 (1995).

Rawlings et al., "A New Family of Serine–type Peptidase Related to Prolyl Oligopeptidase," *Biochem. J.*, *279*(Pt. 3):907–908 (1991).

Sambrook et al., *Molecular Cloning, a Laboratory Manual*, Cold Spring Harbor Laboratory Press, Cold Spring Harbor, New York, title page, publication page and table of contents only, 30 pgs. (1989).

Schägger et al., "Tricine–Sodium Dodecyl Sulfate–Polyacrylamide Gel Electrophoresis for the Separation of Proteins in the Range from 1 to 100 kDa," *Anal. Biochem.*, *166*:368–379 (1987).

Slots et al., "The Occurrence of *Actinobacillus actinomycetemcomitans*, *Bacteroides gingivalis* and *Bacteroides intermedius* in Destructive Periodontal Disease in Adults," *J. Clin. Periodontol.*, *13*:570–577 (1986).

Stenfors et al., "Characterization of Endogenous Neuropeptide Y in Rat Hippocampus and its Metabolism by Nanospray Mass Spectrometry," *J. Biol. Chem.*, 272(9):5747–5751 (1997).

"TIGR," The Institute for Genomic Research, (available on or before Mar. 3, 2000).

Travis et al. Abstract of Grant No. DE 09761, awarded by the National Institutes of Health (available on or before Mar. 3, 2000).

Walter et al., "Proline Specific Endo– and Exopeptidases," *Mol. Cell. Biochem.*, 30(2):111–127 (1980).

Awano et al., "Sequencing, expression and biochemical characterization of the *Porphyromonas gingivalis pepO* gene encoding a protein homologous to human endothelin–converting enzyme," *FEBS Letters*, 1999; 460:139–44.

Banbula et al., "*Porphyromonas gingivalis* DPP–7 Represents a Novel Type of Dipeptidylpeptidase" *The Journal of Biological Chemistry*, Mar. 2, 2001; 276(9):6299–6305.

Barrett et al., *Handbook of Proteolytic Enzymes*, 1998, Academic Press, London, Cover page, Publication page, and Table of Contents only. (13 pgs.).

Beauvais et al., "Biochemical and Antigenic Characterization of a New Dipeptidyl–Peptidase Isolated from *Aspergillus fumigatus*,"*J. Biol. Chem.*, Mar. 7, 1997; 272(10):6238–44.

Berger et al., "Mapping the active site of papain with the aid of peptide substrates and inhibitors," *Phil. Trans. Roy. Soc. Lond. B.*, 1970; 257:249–64.

Birkedal–Hansen et al., "Characterization of collegenolytic activity from strains of *Bacteroides gingivalis*," *J. Periodontal Res.*, Jul. 1988; 23(4):258–264.

Bourgeau et al., "Cloning, Expression, and Sequencing of a Protease Gene (*tpr*) from *Porphyromonas gingivalis* W83 in *Escherichia coli*,"*Infect. Immun.*, Aug. 1992; 60(8):3186–92.

Carmona et al., "Nucleotide sequence of the serine protease gene of *Staphylococcus aureus*, strain V8," *Nucleic Acids Res.*, 1987; 15:6757.

Curtis et al., "Molecular genetics and nomenclature of proteases of *Porphyromonas gingivalis*," *J. Periodontal Res.*, 1999; 34:464–72.

Ellis et al., "Dipeptidyl Arylamidase III of the Pituitary," *J. Biol. Chem.*, Oct. 25, 1967; 242(20):4623–29.

Kato et al., "Sequence Analysis and Characterization of the *Porphyromonas gingivalis prtC* Gene, Which Expresses a Novel Collagenase Activity," *J. Bacteriol.*, Jun. 1992; 174(12):3889–95.

Kumagai et al., "Enzymatic Properties of Dipeptidyl Aminopeptidase IV Produced by the Periodontal Pathogen *Porphyromonas gingivalis* and Its Participation in Virulence," *Infect. Immun.*, Feb. 2000; 68(2):716–24.

Lawson et al., "Biochemical Characterization of *Porphyromonas* (*Bacteroides*) *gingivalis* Collagenase," *Infect. Immun.*, Apr. 1992; 60(4):1524–29.

Groves, "Gene Probes for Bacteria," *Acedemic Press*, 1990; 235–237.

McGuire et al., "Purification and Characterization of Dipeptidyl Peptidase I from Human Spleen," *Arch. Biochem. Biophys.*, Jun. 1992; 295(2):280–88.

"Microbial Genomes Blast Databases" [online]. National Center for Biotechnology Information, 2001 [retrieved on Jul. 2, 2002].

Nelson et al., "Purification and Characterization of a Novel Cysteine Proteinase (Periodontain) from *Porphyromonas gingivalis*," *J. Biol. Chem.*, Apr. 30, 1999; 274(18):12245–51.

Ogasawara et al., "Two Types of Novel Dipeptidyl Aminopeptidases from *Pseudomonas* sp. Strain WO24," *J. Bacteriol.*, Nov. 1996; 178(21):6288–95.

Otogoto et al., "Isolation and Characterization of the *Porphyromonas gingivalis prtT* Gene, Coding for Protease Activity,"*Infect. Immun.*, Jan. 1993; 61(1):117–23.

Pohl et al., "Assignment of the three disulfide bonds in ShK toxin: A potent potassium channel inhibitor from the sea anemone *Stichodactyla helianthus*,"*Lett. Pepetide Sci.*, 1994; 1:291–97.

Rosenfeld et al., "In–Gel Digestion of Proteins for Internal Sequence Analysis after One– or Two–Dimensional Gel Electrophoresis," *Anal. Biochem.*, 1992; 203:173–79.

Travis et al., "The Role of Bacterial and Host Proteinases in Periodontal Disease,"*J. Adv. Exp. Med. Biol.*, 2000; 477:455–65.

Travis, James. "Bacterial Proteinases in Periodontal," Grant Abstract, Grant No. 5R01DE09761–09 [online]. National Institute of Dental Research, Aug. 1, 1991–Dec. 31, 2001.

Vacheron et al., "Caractérisation d'une nouvelle endopeptidase spécifique des liaisons γ–D–glutamyl–L–lysine et γ–D–glutamyl–(L)*meso*–diaminopimélate de substrats peptidoglycaniques, chez *Bacillus spaericus*9602 au cours de la sporulation," *Eur. J. Biochem.*, 1979; 100:189–96.

Kuramitsu., "Proteases of *Porphyromonas gingivalis*: what don't they do?",*Oral Microbiology and Immunology*, 13:263–270 (1998).

XP002219380, "*Zylella fastidiosa* 9a5c", created on Jul. 18, 2000 [retrieved from EMBL Database] Accession No. AE004008 (3 pgs.).

XP002219381, "Glutamyl endopeptidaseprecursor (EC3.4.21.19)", created on Mar. 20, 1987; [retrieved from EMBL Database] Accession No. P04188 (1 pg.).

* cited by examiner

```
SEQ ID NO:
26  Mm-FAP    1   MKTWLKTVFGVTTLAATAIWICIVLRPSR--VYKPEGNTK-RALTLKDILNGTFSYKTYF
27  Hs-DPP    1   MKTPWKVLLGLIGAAAVTLLTPVVLLNKGTDDATADSR-KTYTLTDYLKNTVRLKLYS
28  Fm-DPP    1   ---MKKTFSLISIAVVAFHGLSAQEITLDKHYSGQTAK-GISHASIND---------
29  Pg-DPP    1   -MKRPVILLLGIVMCAMAQTGNKPVDLKETTSGMFYARSAGSHIRSMPD---------
30  PTP-A     1   --MKTIFQQIFLSVQALTVALPCSAQSPETSGKEFTLEQLMPEGKEFYN--FYPEYVV

Mm-FAP    59  PNWISEQEYTHQS--EDDNIVFYNIETRE--SYTILSNSTMKSVN--ATDYGISPDRQFVM
    Hs-DPP    60  LRWISDHEYLYK---QENHILVENAEYGN--SSVFLENSIFDEEFGHSINDYSISPDGQFIL
    Fm-DPP    48  ------GENVATI--EPTGHAKVSYKITSQ--KEKNLVDGSFQGYT----FSNDESK---
    Pg-DPP    51  ------GEHYTEMNRERTALIRYNYASCKAVDTIFSVERARECPFKQIQNYEVSTGHHL
    PTP-A     56  GLQWMGDNYVFIE----GDDLVENKANEKSAQTRFSAADLNALMPEGCKFQTDAFPSFR

Mm-FAP    114 IESDYSKLMRVSYTFATVYMDI QNGEFVRGYEL PRPIQYLONSPVGSKLAYVQNIYLK
    Hs-DPP    116 IEYNYVKQMRHSYTASYDIIYDIDLNKROLITEERIPNNTQWTMSPYGHKLLAYVWNNDIYVK
    Fm-DPP    92  LQKSSQSIYRHSFLGKFEVKDLKSRIVVSINNANWIQE--PKFSPDGSSKVAFIADNNLFYQ
    Pg-DPP    106 LFTDMESIYRHSYRAAVYDVQVRRNLVKPLSEHVGKVMIPTESPDGRMVAEVVRDNNTFIK
    PTP-A     113 TLDAGRGLVVLFTQGGLVGFDMLARKVTYLFDTNEETASLFESPVGDRKVAYVRNIMLA

Mm-FAP    174 QRP--GEPPFQTITVTGREARIFNGIIPDWVYEEEMLATKYALAWSPDGKFLAYMPFNDSDI
    Hs-DPP    176 IEP--NLPSYRIWIGKEDIIYNGIITDWVYEEEVFSAYSALMWSPNGTFLAVAQFNDTEV
    Fm-DPP    151 DLN--TGKITQITTDGKKNEIINGLGDWVYEEEFGHADYYQWN--KAGDALVFVRFDDRKV
    Pg-DPP    166 KFD--FDTEVQMTDQIINSILNGATDWVYEEEFGVTNLMSAS--ADNAELAFYRSLESAM
    PTP-A     173 RGGKLGEGMSRAIAVTIDSTETLVYGQAVHQREEGIEKGTFMS--EKGSCLAFYRMDOSSMW

Mm-FAP    232 PILAYSYVGDG----QVFRTINIPYPKAGAKNPVNRVFIVDTTYPLHVG----PMEVPVFEMI
    Hs-DPP    234 PLIEYSFYSDESLQKPKTVRVPYPKAGAVNPTVKFFVMNTDSLSSVTNATSIQITAFASM
    Fm-DPP    208 PENINPIMYQN---LYFKIMTYKYPAGEENSAVITAYVLMQLSSGKSAQ---LNFGSSEKY
    Pg-DPP    223 PEYRMPMYEK---LYFEDYTYKYPKAGEKNSTVSLHLMNVADRNIKS---VSLPIDADG
    PTP-A     232 KPTPHVDHP---LFAEKPLYZPMAGTPSHHVTVGHWFLAIGKIMY---LQTGEEKEK
```

```
Mm-FAP  582  DKEIHPAVYRKLGMVEVEDOLIAVRKFIEMGFIDEERIAIWGWSYGGYVSSLALASGEL
Hs-DPP  588  DKIMHALNERICIFEVEDOIEAROFSKMGFVDNKRIAIWGWSYGGYVTSMVLGSGSGVE
Fm-DPP  539  TKYKKVTYKNLGKYEHEDOIIAAKWLGNQSYVDKSRIGIEGWSYGGYMASTAMTKGADVE
Pg-DPP  551  EEWRKCTVMQLGVFESDDQIPAATAIGQEPYVDAARIGIWGWSYGGYTHIMSECRGNEL
             AAFEQVIHRRLGQTEMADQMGGVDFLKSQSWVDADRIGVHCWSYGGEMLINLMIHGDVE

Mm-FAP  642  KCGIAVAPVSSWEYYASIMSERFMGLPTKDDNLEHYKNSTVMARAEYFRNVDYLLIHGTA
Hs-DPP  648  KCGTAVAPVSGWEYYESVTERYMGLPTPEDNLDHYRNSTVMSRAENFKQVEYLLIHGTA
Fm-DPP  599  KMGIAVAPVSRWEYYDSIMTERELQTQENK---DGYDLNSPTTYAKLEKG-KELLIHGTA
Pg-DPP  611  KAGIAVAPVADWRFMDSVTERFMRTFKENA---SGYKMSSAIDVASQEG--NLLTVSGSA
             KVEMAGGEVIDWNRVPIMYGERYFDAPEHNP--EGYDAANILKRAGD KG--RIMIHGAI

Mm-FAP  702  DDNVHFQNSAQIAKALVNAQVDFQAMWYSDQNHGISSERQNHLYTHMTHFLKQCFSLSD
Hs-DPP  708  DDNVHFQNSTQIAKALVNAQVDFQAMWYSDQNHGLASSTAHQHIYTHMSHFIKQCFSLP-
Fm-DPP  656  DDNVHFQNSMEFSEALIQNKKQFDFMAVPDKNHSIIGGNIRPQLYEKMINVILEN-----
Pg-DPP  668  DDNVHFQNITMLITEALVQANIPFDMATYMBKNNSIYGGNLRMHIYTIRKAKELEDNL---
             DPVMMQFSLLETDACMKERTYPYVMPSHEHNMMGPD-RMHLYETIHRYFTDHL-----
                                                               *
```

Fig. 3c

|  |  |  |  | SEQ ID NO: |
|---|---|---|---|---|
| PTP-A | 556 VDADRIGMHGMSYGGFMT... | REMLIHGAIDPVMWQHSTLFLDACVKARTYPDYWVPSHEHNVMGED-R | 717 | 31 |
| DPP | 499 VDAARIGIWGMSYGGYMI... | NLLIVSGSADDNVHLQNTMLFTEAIVQANIPFDMAIMDKNHSIYGGNTR | 661 | 32 |
| DPP-H1 | 350 VDPDRIAIYGASIGCLYAH... | PLFVVQGANDPRVNINESDQIVTALRARGFEVPYMVKYNEGHGFHREENS | 524 | 33 |
| DPP-H2 | 640 VNGKKVGQFGASYGGFMI... | PLILIHGSVDNVPTAESVNLYNAIKILGREVEFIEFTQDFFTIEPERR | 810 | 34 |
| DPP-H3 | 495 VDGDRIGAVGASYGGFSV... | PILMIHGFLDFRILASQAMAAFDAAQLRGVPSEMLIKPDENEWLQBQNA | 667 | 35 |

Fig. 4

```
SEQ ID NO:
30  126PP    1   MKKTFQQLF-----LSVCALTVALPCSAQSPETSGKEFTLEQLMPGGKEF---YNFYPEYV
42   87PP    1   -----------------------------------------MPDGEHV--TEMARERT
43   65PP    1   -----------------------------------------LDKGG---NENYHLFA
44  101PP    1   MKBSLLMILSAATLSSIEAQTIQQMKAGGPWPVRAAFKTDTVGMNSSKVNPADLLRQAY
45    9PP    1   MNKKIFSMMAAS--LIGSAAMTPSAGTNTGEHLTPELFMTLSRVSEMALS--PDGKTAVY

126PP   55   VGLQWMGDVYVF-------IEGDDLVNKANG----------KSAQTTRFSAADLNALMPEGCKFQ
     87PP   16   ALLRY----NYAS----GKAVDTLFSVER---------ARECPFKQIQ---N----I---VE
     65PP   14   SNLDG-----S----NTRDLTPDGVK------------ASILNMLKEQK-----L----VM
    101PP   61   DATDKDLRNVSADKDGRIAGRKAGSKAEHSEMAVYSFALTAEHFAKADIEVFGQGRMSLW
      9PP   57   AVSFP------DVKLI----------NKATRELFTVNLD----GSGRKQITDTESN----EYAPAW

126PP  104   TTDAFPSFRTLDAGRG-------LMLFTQGGLVGHDMLARKVTYT--FQTNEETASLDFSP
     87PP   50   VSSTGHILLFTDMES------IYRHSYRAAVYDYDVRNIVKPL---SEHVGKVMIPTFSP
     65PP   46   IISMNK-----NNPQ-----IFEPYKINVTIGELIQLYEN----KDAANPLQGYEDK
    101PP  121   LDEKQIGIADSPNSKDTTLRFSASISLVPGTHLIIKSILEGTITATDVRVVLKPKTA
      9PP   98   MADGKTI-LAFMSNFGG------SMQLWVMNADSTERRQLSN-----IEGGITGFLFSP

126PP  157   -V-----------G--DRVAVVRNHN--LYIARG--GKLGEGMSRAIAVTDGTETLVVGQA-
     87PP  103   -D---------G--RMVAFMRDNN--IFIK----KFDFDTE--VQVTDGQINSTLNGATD
     65PP   90   -D---------G--ELRGYSR----------------LVNGIESELVYKD-------
    101PP  181   RDSSALYPNYTGKPFLSLKHMMSGTFLSGGSLSPTGKYVLTSYRVSRNKPAVTVNQLRD
      9PP  144   -E--KQVLFTKD-----------------------IKFGKRTKDIVPDLDK
```

Fig. 6a

```
126PP  201  -MHQREFGIEKG---TFMSPKGSCLAFYRM----------------DQS-MVKPTFIVDYH-----PI
87PP   144  WVYEEFGVTNL--MSWSADNAFLAFVES----------------DES-AVPEYRMPMYEDD---KC
65PP   112  -LATGETRILKK---THMDDTFGVIAENYA--------------SKN-KDFAYLITNLD-----S
101PP  241  AKGNILLNLNEKEALGMPHEDMMVIRKEGNAKRLVAFDPMGKGEKTLVSNLPESQFRM
9PP    170  ATGRIITDLMYK---HMDEWVETIPHPFI---------------AN-AIDGMIITGKD-----I

126PP  243  EAESKPLYKPMAGT---PSHHVTVGIYHLA-----TG-KTVYLQTGEFREKPLTNELSWSPDE
87PP   188  YPEDYTYKYPKAGE---KNSTVSLHLYNVA-----DR-NTKSVSFPIDADGYIPRIIAETDNA
65PP   153  DK-TRIVLYDLKQN---K--IIREIFANE-----DY-DVSGLHLS-RK---------------
101PP  301  SPDARYILFYKQEKGPGKDPLFIRHLDPDDRSQDWRDRSQIVLNAESGVYGPITEGYST
9PP    210  ME-GEPIEAPMKPW------S-GIEDFSWSP----DG--QNIAYASRKIG------------

126PP  296  NIFIVAE--VNTRAQNECKVNAMDAETGRFVRTIFVETDKHYVEP--LH-P---------LP
87PP   241  DELAVMT--LNRLQNDFKM-YVVHPKSLVPKLILQDMNKRYVDSDWIQ-T---------LKITT
65PP   188  -R------N-YEIDLMA--VEGEKSVVVPMSATYKEIHKLME-------------KEEK
101PP  361  TYHTDTAPDSKRALIGTLSTDWTRRPFRFATIMEYNMETGKADTLITRDPSIDADYTPD
9PP    247  -MAVSLS---TN--SDIYH-MNLASGHTHNIBEGMMGYDTYPK-----------------FSPD

126PP  346  GSNNQFIMQSR-RDGWNHLVI-----------------VDTTGRLIRQVIKGEWEVTNFA----G
87PP   292  GGG--FAYVSE--KDGFAHIDYL-------------VDNKGVMHRRIIISGNMDVEKLY----G
65PP   224  GKE---FSVM---D--------------------VDD---------------------------
101PP  421  GKH---LIVGS-ADAFGNIEINLKSGVTPNSVDKQFFLFDLSRKATALIKNFNPSVSAG
9PP    287  GKS---IAWISMERDGYES-----------------DLKRLFVADLAIGKRTHVNPTFDYNVDMI
```

```
126PP  618  DMFKVGVAGPVI----------WN---RYEIMVGERVFEA----PQENPEGYD-AANLLK
87PP   561  GTFKAGIAVEPVA---------D----------WR---FYDSVYTERFMRT---PKENASGYK-MSSALD
65PP   412  DLYACGVDYVGVSNIYTFFDSFPEYVK---------PFKEMVKEIMYELDNPEEAAIAKE-VSPFFQ
101PP  702  DIFAAVSHAGISSIS-------N----YNGSGYWMGYSTVASTDSYEWNNPDLYAGHSPLFR
9PP    557  KREAAFIAHAGIFNLEMQYATTEEMMFA-NWDIGGPFWEKDN----VVAQRTYA-TSFHKF

126PP  662  RAGDIKGRIMLIHCAIDPVVWQHSILFLDACVKARTYPDYVMVPSHEHNVMGPD-RVLHF
87PP   605  VASQLQGNLIIVSGSSADDNVHLQNIMLFTEAIVQANIPFDMAIVDKNISLYGGNTRVLL
65PP   469  DD-KINKPLFVVQGANDPRVNINESDQIVTALRARGFEVPYMVKYNEGHGFHREDNSMDL
101PP  755  AD-KIHTIPILLLHGSVPITNVPTAESVNLYNALKILGREVEFIEFTEDHFILPPRRIRW
9PP    612  MQ-NWDTEIIMIHGELFLEFRILASQAMAAFDAAQLRGVPSEMLIMPDENEHWLQEQNALLF

126PP  721  METITRVETDHE----------
87PP   665  MTRKAKFLFDNL----------
65PP   528  VPAMLGFFAKHLKK--------
101PP  814  TNSICAWEFARWLQDDPTWWNELYPPVNL
9PP    671  HRIFFGWLDRWEKK--------
```

Fig. 6d

P. gingivalis W 83 PTP sequence

SEQ ID NO: 38　13228　atgaagaagacaatcttccaacaactatttctgtctgtttgtgcc
SEQ ID NO: 30　　　　　　M   K   K   T   I   F   Q   Q   L   F   L   S   V   C   A
　　　　　　　　13273　cttacagtggccttgccttgttcggctcagtctcctgaaacgagt
　　　　　　　　　　　　L   T   V   A   L   P   C   S   A   Q   S   P   E   T   S
　　　　　　　　13318　ggtaaggagtttactcttgagcaactgatgcccggaggaaaagag
　　　　　　　　　　　　G   K   E   F   T   L   E   Q   L   M   P   G   G   K   E
　　　　　　　　13363　ttttataacttttaccccgaatacgtggtcggtttgcaatggatg
　　　　　　　　　　　　F   Y   N   F   Y   P   E   Y   V   V   G   L   Q   W   M
　　　　　　　　13408　ggagacaattatgtctttatcgagggtgatgatttagtttttaat
　　　　　　　　　　　　G   D   N   Y   V   F   I   E   G   D   D   L   V   F   N
　　　　　　　　13453　aaggcgaatggcaaatcggctcagacgaccagatttctgctgcc
　　　　　　　　　　　　K   A   N   G   K   S   A   Q   T   T   R   F   S   A   A
　　　　　　　　13498　gatctcaatgcactcatgccggagggatgcaaatttcagacgact
　　　　　　　　　　　　D   L   N   A   L   M   P   E   G   C   K   F   Q   T   T
　　　　　　　　13543　gatgctttcccttcattccgcacactcgatgccggacggggactg
　　　　　　　　　　　　D   A   F   P   S   F   R   T   L   D   A   G   R   G   L
　　　　　　　　13588　gtcgttctatttacccaaggaggattagtcggattcgatatgctt
　　　　　　　　　　　　V   V   L   F   T   Q   G   G   L   V   G   F   D   M   L
　　　　　　　　13633　gctcgaaaggtgacttatctttcgataccaatgaggagacggct
　　　　　　　　　　　　A   R   K   V   T   Y   L   F   D   T   N   E   E   T   A
　　　　　　　　13678　tctttggattttctcctgtgggagaccgtgttgcctatgtcaga
　　　　　　　　　　　　S   L   D   F   S   P   V   G   D   R   V   A   Y   V   R
　　　　　　　　13723　aaccataaccttcacattgctcgtggaggtaaattgggagaaggt
　　　　　　　　　　　　N   H   N   L   Y   I   A   R   G   G   K   L   G   E   G
　　　　　　　　13768　atgtcacgagctatcgctgtgactatcgatggaactgagactctc
　　　　　　　　　　　　M   S   R   A   I   A   V   T   I   D   G   T   E   T   L
　　　　　　　　13813　gtatatggccaggccgtacaccagcgtgaattcggtatcgaaaaa
　　　　　　　　　　　　V   Y   G   Q   A   V   H   Q   R   E   F   G   I   E   K
　　　　　　　　13858　ggtacattctggtctccaaaagggagctgccttgctttctatcga
　　　　　　　　　　　　G   T   F   W   S   P   K   G   S   C   L   A   F   Y   R
　　　　　　　　13903　atggatcagagtatggtgaagcctaccccgatagtggattatcat
　　　　　　　　　　　　M   D   Q   S   M   V   K   P   T   P   I   V   D   Y   H
　　　　　　　　13948　ccgctcgaagccgagtccaaaccgctttattaccccatggcaggt
　　　　　　　　　　　　P   L   E   A   E   S   K   P   L   Y   Y   P   M   A   G
　　　　　　　　13993　actccgtcacaccacgttacggttgggatctatcatctggccaca
　　　　　　　　　　　　T   P   S   H   H   V   T   V   G   I   Y   H   L   A   T
　　　　　　　　14038　ggtaagaccgtctatctacaaacgggtgaacccaaggaaaaattt
　　　　　　　　　　　　G   K   T   V   Y   L   Q   T   G   E   P   K   E   K   F
　　　　　　　　14083　ctgacgaatttgagttggagtccggacgaaaatatcttgtatgta
　　　　　　　　　　　　L   T   N   L   S   W   S   P   D   E   N   I   L   Y   V
　　　　　　　　14128　gctgaggtgaatcgtgctcaaaacgaatgtaaggtaaatgcctat
　　　　　　　　　　　　A   E   V   N   R   A   Q   N   E   C   K   V   N   A   Y
　　　　　　　　14173　gacgctgagaccggtagattcgtccgtacgcttttgttgaaacc
　　　　　　　　　　　　D   A   E   T   G   R   F   V   R   T   L   F   V   E   T
　　　　　　　　14218　gataaacattatgtagagccgttacatcccctgacattccttccg
　　　　　　　　　　　　D   K   H   Y   V   E   P   L   H   P   L   T   F   L   P

Fig. 7a

```
14263 ggaagtaacaatcagttcatttggcagagccgtcgcgacggatgg
       G  S  N  N  Q  F  I  W  Q  S  R  R  D  G  W
14308 aaccatctctatctgtatgatactacaggtcgtctgatccgtcag
       N  H  L  Y  L  Y  D  T  T  G  R  L  I  R  Q
14353 gtgacaaaaggggagtgggaggttacaaactttgcaggcttcgat
       V  T  K  G  E  W  E  V  T  N  F  A  G  F  D
14398 cccaagggaacacggctctatttcgaaagtaccgaagccagccct
       P  K  G  T  R  L  Y  F  E  S  T  E  A  S  P
14443 ctcgaacgccattttactgtattgatatcaaaggaggaaagaca
       L  E  R  H  F  Y  C  I  D  I  K  G  G  K  T
14488 aaagatctgactccggagtcgggaatgcaccgcactcagctatct
       K  D  L  T  P  E  S  G  M  H  R  T  Q  L  S
14533 cctgatggttctgccataatcgatatttttcagtcacctactgtc
       P  D  G  S  A  I  I  D  I  F  Q  S  P  T  V
14578 ccgcgtaaggttacagtgacaaatatcggcaaagggtctcacaca
       P  R  K  V  T  V  T  N  I  G  K  G  S  H  T
14623 ctcttggaggctaagaaccccgatacgggctatgccatgccggag
       L  L  E  A  K  N  P  D  T  G  Y  A  M  P  E
14668 atcagaacgggtaccatcatggcggccgatgggcagacacctctt
       I  R  T  G  T  I  M  A  A  D  G  Q  T  P  L
14713 tattacaagctcacgatgccgcttcatttcgatccggcaaagaaa
       Y  Y  K  L  T  M  P  L  H  F  D  P  A  K  K
14758 tatcctgttattgtctatgtttacggaggacctcatgcccaactc
       Y  P  V  I  V  Y  V  Y  G  G  P  H  A  Q  L
14803 gtaaccaagacatggcgcagctctgtcggtggatgggatatctat
       V  T  K  T  W  R  S  S  V  G  G  W  D  I  Y
14848 atggcacagaaaggctatgccgtctttacggtggatagtcgcgga
       M  A  Q  K  G  Y  A  V  F  T  V  D  S  R  G
14893 tctgccaatagaggggctgctttcgagcaggttattcatcgtcgt
       S  A  N  R  G  A  A  F  E  Q  V  I  H  R  R
14938 ttggggcagaccgagatggccgatcagatgtgcggtgtggatttc
       L  G  Q  T  E  M  A  D  Q  M  C  G  V  D  F
14983 ctcaagagccaatcatgggtggatgccgatagaataggagtacat
       L  K  S  Q  S  W  V  D  A  D  R  I  G  V  H
15028 ggctggagctatggtggctttatgactacgaatctgatgcttacg
       G  W  S  Y  G  G  F  M  T  T  N  L  M  L  T
15073 cacggcgatgtcttcaaagtcggagtagccggcgggcctgtcata
       H  G  D  V  F  K  V  G  V  A  G  G  P  V  I
15118 gactggaatcgatatgagattatgtacggtgagcgttatttcgat
       D  W  N  R  Y  E  I  M  Y  G  E  R  Y  F  D
15163 gcgccacaggaaaatcccgaaggatacgatgctgccaacctgctc
       A  P  Q  E  N  P  E  G  Y  D  A  A  N  L  L
15208 aaacgagccggtgatctgaaaggacgacttatgctgattcatgga
       K  R  A  G  D  L  K  G  R  L  M  L  I  H  G
15253 gcgatcgatccggtcgtggtatggcagcattcactccttttcctt
```

Fig. 7b

```
              A   I   D   P   V   V   V   W   Q   H   S   L   L   F   L
    15298  gatgcttgcgtgaaggcacgcacctatcctgactattacgtctat
              D   A   C   V   K   A   R   T   Y   P   D   Y   Y   V   Y
    15343  ccgagccacgaacataatgtgatggggccggacagagtacatttg
              P   S   H   E   H   N   V   M   G   P   D   R   V   H   L
    15388  tatgaaacaataacccgttatttcacagatcacttatga  15426
              Y   E   T   I   T   R   Y   F   T   D   H   L   *
```

Fig. 7c

SEQ ID NO:38  ATGAAGAAGACAATCTTCCAACAACTATTTCTGTCTGTTTGTGCCCTTACAGTGGCCTTGCCTTGTCGGC
TCAGTCTCCTGAAACGAGTGGTAAGGAGTTACTCTGAGCAACTGATGCCCGGAGAAAAGAGTTTATA
ACTTTTACCCCGAATACGTGGTCTCGGTTTGCAATGGATGGAGACAATTATGTCTTTATCGAGGGTGATGAT
TTAGTTTTTAATAAGGCAATGGCAAATCGGCTCAGACGCTGATGCTTCCTTCGCCGATCTCAATGCACT
CATGCCGAGGGATGCAAATTTCAGACGACTGATGCTTTCCCTTCATTCGCCACACTCGATGCCGACGGG
GACTGGTCGTCGTTCTATTTACCCAAGGAGAGGATTAGTCGATTCGATATGCTTGCTCGAAAGGTGACTTATCTT
TTCGATACCAATGGAGGAGACGGCTTCTTTGGATTTTTCTCCTGTGGGAGACCGTGTTGCCTATGTCAGAAA
CCATAACCTTTACATTGCTCGTGGAGTAAATTGGGAGAAGTATGTCACGAGCTATCGTGTGACTATCG
ATGGAACTGAGACTCTCGTATATGCCAGGCCGTACACCAGCTGAATTCGGTATCGAAAAAGTACATTC
TGGTCTCCAAAAGGGAGCTGCCTTGCTTTCTATCGAATGGATCAGAGTATGTGAAGCCTACCCCGATAGT
GGATTATCATCCGCTCGAGTCCGAGTCCCAAACCGCTTTATTACCCGCCAGGTACTCCGTCACACCACG
TTACGGTTGGGATCTATCATCTGGCCACAGTAAGACCGTCTATCTACAAACGGGTGAACCAAGGAAAA
TTTCTGACGAATTTGAGTTGGAGTCCGGACGAAGAAAATATCTTGTATGTAGCTGAGGTGAATCGTGCTCAAA
CGAATGTAAGGTAAATGCCTATGACGCGTAGATTCGTCCGTAGATTCGTCCGTACGCTTTTTGTTGAAACCGATA
AACATTATGTAGAGCCGTTACATCCCCTGACATTCCTTCCGGAAGTAACAATCAGTTCATTTGGCAGAGC
CGTCGCGACGGATGGAACCATTCTCTATCTGTATGATACACAGGTCGTCTGATCCGTCAGTGACAAAGG
GGAGTGGGAGGTTACAAACTTGCAGGCTTCGATCGATCCAAGGGAACACGGCTCTATTTCGAAAGTACCGAAG
CCAGCCCCTCTCGAAACGCCATTTTTACTGTATTGATATCAAAGGAGGAAAGACAAAAGATCTGACTCCGGAG
TCGGGAATGCACCCGACTCAGCTATCTCCTGATGGTTCTGCCATAATCGATATTTTCAGTCACTACTGT
CCCGCGTAAGGTTACAGTGACAAATATCGGCAAAGGGTCTCACACACTCTTGGAGGCTAAGACACCCGATA
CGGGCTATGCCATGCCGGAGATCAGAACGGTACCATCATGCGGCCGATGGGCAGACACCTCTTTATTAC
AAGCTCACGATGCCGCTTCATTTCGATCCGGCAAAGAAATATCCTGTTATTGTCTATGTTTACGAGGACC
TCATGCCCAACTCGTAACCAAGACATGGCCAGCTCTGTCGGTGGATGGATATCTATATGCCACAGAAAG
GCTATGCCGTCTTTACGGTGGATAGTCGCGGATCTGCCAATAGAGGGCTGCTTTCGAGCAGGTTATTCAT
CGTCGTTTGGGCAGACCGAGATGCCGATCAGATGTGCCGTGTGGATTTCCTCAAGAGCCAATCATGGT
GGATGCCGATAGAATAGGAGTACATGCTGGAGCTATGGTGCTTTATGACTACGAATCTGATGCTTACGC
ACGGCGATGTCTTCAAAGTCGGAGTAGCCGGCGGGAAATCCCGAAGGATACGATGCTGCCAACCTGCTCAAACGAC
GGTGAGCGTTATTCGATGCCGCCACAGGAAATCCCGAAGGATACGATGCCGGTCGTGGTATGCAGCATTCAC
CGGTGATCTGAAAGGACGACTTATGCTGATTCATGGAGCGATCGGATCCTACTATTACCGTTATTCACAGATCACTTATGA
TCCTTTTCCTTGATGCTTGCGTGAAGCACGCACCTATCCTGACTATTACGTCTATCCGAGCCACGAACAT
AATGTGATGGGCCGACAGAGTACATTTGTATGAAACAATAACCCGTTATTCACAGATCACTTATGA

Fig. 7d

PROLYL TRIPEPTIDYL PEPTIDASES NUCLEIC ACID OF *PORPHYROMONAS GINGIVALIS*

CONTINUING APPLICATION DATA

This patent application claims the benefit of U.S. provisional patent application No. 60/123,148, filed Mar. 5, 1999, now abandoned which is incorporated by reference herein.

GOVERNMENT FUNDING

The present invention was made with government support under Grant No. DE 09761, awarded by the National Institutes of Health. The Government may have certain rights in this invention.

BACKGROUND OF THE INVENTION

*Porphyromonas gingivalis* (formerly *Bacteroides gingivalis*) is an obligately anaerobic bacterium which is implicated in periodontal disease. *P. gingivalis* produces several distinct proteolytic enzymes, many of which are recognized as important virulence factors. A number of physiologically significant proteins, including collagen, fibronectin, immunoglobulins, complement factors C3, C4, C5, and B, lysozyme, iron-binding proteins, plasma proteinase inhibitors, fibrin and fibrinogen, and factors of the plasma coagulation cascade system, are hydrolyzed by *P. gingivalis* proteases. Broad proteolytic activity plays a role in the evasion of host defense mechanisms and the destruction of gingival connective tissue in progressive periodontitis.

Progressive periodontitis is characterized by acute tissue degradation promoted by collagen digestion and a vigorous inflammatory response characterized by excessive neutrophil infiltration. Gingival crevicular fluid accumulates in periodontitis as periodontal tissue erosion progresses at the foci of the infection, and numerous plasma proteins are exposed to proteinases expressed by the bacteria at the injury site. Neutrophils are recruited to the gingiva, in part, by the humoral chemotactic factor C5a. The complement components C3 and C5 are activated by complex plasma proteases with "trypsin-like" specificities called convertases. The human plasma convertases cleave the α-chains of C3 and C5 at a specific site generating biologically active factors known as anaphylatoxins (i.e. C3a and C5a). The anaphylatoxins are potent proinflammatory factors exhibiting chemotactic and/or spasmogenic activities as well as promoting increased vascular permeability. The larger products from C3 and C5 cleavage (i.e. C3b and C5b) participate in functions including complement cascade activation, opsonization, and lytic complex formation.

Recent studies have indicated that this periodontopathogen produces at least seven different enzymes belonging to the cysteine and serine catalytic classes of peptidases, among which three cysteine proteinases (gingipains) are predominant (Potempa, J., et al. (1995) *Prospect. Drug Discovery and Design* 2, 445–458). The gingipains are the best characterized group of *P. gingivalis* enzymes as their structure, function, enzymatic properties and pathological significance are known. From in vitro studies it is apparent that two gingipains R (also referred to generally as "Arg-gingipains" and more specifically as RgpA and RgpB), enzymes specific for cleavage at Arg-Xaa peptide bonds, have a significant potential to contribute to the development and/or maintenance of a pathological inflammatory state in infected periodontal pockets through: (i) activation of the kallikrein-kinin cascade, (ii) the release of neutrophil chemotactic activity from native and oxidized C5 of the complement pathway, and (iii) activation of factor X. In addition, gingipain K (also referred to as "Lys-gingipain"), an enzyme which cleaves Lys-Xaa peptide bonds, degrades fibrinogen. This may add to a bleeding on probing tendency associated with periodontitis. Finally, the presence of a hemagglutinin/adhesion domain in the non covalent multi-protein complexes of RgpA and gingipain K suggests participation of these enzymes in the binding of *P. gingivalis* to extracellular matrix proteins which may facilitate tissue invasion by this pathogen.

In comparison to the gingipains, relatively little is known about other cysteine proteinases produced by *P. gingivalis*. Two genes, referred to as tpr and prtT have been cloned and sequenced and although they encode a putative papain-like and streptopain-like cysteine proteinases, respectively, neither has been purified and characterized.

The presence of serine proteinase activity in cultures of *P. gingivalis* has been known for several years; however, only limited information is available about such enzymes. Indeed, a serine endopeptidase has been isolated from culture media, although it was only superficially characterized (Hinode D., et al., (1993) *Infect. Immun.* 59, 3060–3068). On the other hand, an enzyme referred to as glycylprolyl peptidase (DPP IV) was found to be associated with bacterial surfaces and two molecular mass forms of this peptidase have been described. This enzyme has also been shown to possess the ability to hydrolyze partially degraded type I collagen, releasing the Gly-Pro dipeptide, and it was suggested that, in collaboration with collagenase, glycylprolyl peptidase may contribute to the destruction of the periodontal ligament (Abiko, Y., et al. (1985) *J. Dent. Res.* 64, 106–111). In addition to this potential pathological function, glycylprolyl peptidase may also play a vital role in providing *P. gingivalis* with dipeptides which can be transported inside the cell and serve as a source of carbon, nitrogen, and energy for this asaccharolytic organism. Recently, a gene encoding glycylprolyl peptidase in *P. gingivalis* has been cloned and sequenced, and it is now apparent that this enzyme is homologous to dipeptidyl-peptidase IV (DPP-IV) from other organisms (Kiyama, M., et al. (1998) 1396, 39–46). The nucleotide sequence of the genome of this bacterium is currently being determined by The Institute for Genomic Research, and is available on the World Wide Web at tigr.org.

SUMMARY OF THE INVENTION

The present invention is directed to an isolated prolyl tripeptidyl-peptidase, active analog, active fragment, or active modification thereof having amidolytic activity for cleavage of a peptide bond present in a target polypeptide having at least 4 amino acids. Alternatively, the isolated prolyl tripeptidyl-peptidase, active analog, active fragment, or active modification thereof is isolated from *P. gingivalis*. Typically, amidolytic activity is determined with a prolyl tripeptidyl-peptidase:target polypeptide ratio of at least about 1:1 to no greater than about 1:10,000,000 in about 200 mM HEPES, about pH 7.5 at 37° C. for at least about 3 hours. The peptide cleaved by the isolated prolyl tripeptidyl-peptidase can include the sequence of SEQ ID NO:1, SEQ ID NO:2, SEQ ID NO:7, SEQ ID NO:8, SEQ ID NO:10, SEQ ID NO:11, H-Ala-Arg-Pro-Ala-D-Lys-amide, SEQ ID NO:13, SEQ ID NO:14, SEQ ID NO:15, SEQ ID NO:25, or SEQ ID NO:37. The amino acid sequence of the isolated prolyl tripeptidyl-peptidase can include the amino acid sequence GXSXXG (SEQ ID NO:39), the amino acid sequence GXSXGG (SEQ ID NO:40), or the amino acid sequence of SEQ ID NO:30.

Another aspect of the invention is an isolated polypeptide, active analog, active fragment, or active modification thereof having amidolytic activity for cleavage of a peptide bond present in a target polypeptide having at least 4 amino acids. Typically, the polypeptide:target polypeptide ratio of at least about 1:1 to no greater than about 1:10,000,000 in about 200 mM HEPES, about pH 7.5 at 37° C. for at least about 3 hours.

The invention is also directed to an isolated polypeptide comprising an amino acid sequence having a percentage amino acid identity of greater than 35% with SEQ ID NO:30.

An alternative aspect of the invention is an isolated nucleic acid fragment encoding a prolyl-tripeptidyl peptidase, active analog, active fragment, or active modification thereof, having amidolytic activity for cleavage of a peptide bond present in a target polypeptide having at least 4 amino acids. Typically, the prolyl tripeptidyl-peptidase:target polypeptide ratio of at least about 1:1 to no greater than about 1:10,000,000 in about 200 mM HEPES, about pH 7.5 at 37° C. for at least about 3 hours. The nucleic acid fragment can have a nucleotide sequence comprising SEQ ID NO:38. A complement of the nucleic acid fragment can hybridize to SEQ ID NO:38 under hybridization conditions of 0.5 M phosphate buffer, pH 7.2, 7% SDS, 10 mM EDTA, at 68° C., followed by three for 20 minutes washes in 2×SSC, and 0.1% SDS, at 65° C., wherein at least about 20 nucleotides of the complement hybridize.

Another aspect of the invention is an isolated nucleic acid fragment encoding a polypeptide that includes an amino acid sequence having a percentage amino acid identity of greater than 35% with SEQ ID NO:30.

The invention is also directed at a method of identifying an inhibitor of a prolyl-tripeptidyl peptidase, active analog, active fragment, or active modification thereof, including identifying a molecule that inhibits the amidolytic activity of the prolyl-tripeptidyl peptidase. The inhibitor is identified by incubating the prolyl-tripeptidyl peptidase with the molecule under conditions that promote amidolytic activity of the prolyl-tripeptidyl peptidase and determining if the amidolytic activity of the prolyl-tripeptidyl peptidase is inhibited relative to the amidolytic activity in the absence of molecule.

An aspect of the invention is a method of reducing growth of a bacterium. This method includes inhibiting a prolyl tripeptidyl-peptidase, active analog, active fragment, or active modification thereof, or a prolyl dipeptidyl-peptidase, active analog, active fragment, or active modification thereof. The method includes contacting the prolyl tripeptidyl-peptidase with an inhibitor of the prolyl tripeptidyl-peptidase. The method can be used to protect an animal from a periodontal disease caused by P. gingivalis including administering to the animal the inhibitor. The disease can be selected from the group consisting of gingivitis and periodontitis. The inhibitor can be administered by a method selected from the group consisting of subgingival application and controlled release delivery.

Another aspect of the invention is an immunogenic composition including an isolated prolyl tripeptidyl-peptidase, or an antigenic analog, antigenic fragment, or antigenic modification thereof, the prolyl tripeptidyl-peptidase having amidolytic activity for cleavage of a peptide bond present in a target peptide having at least 4 amino acids. Typically, the prolyl tripeptidyl-peptidase:target polypeptide ratio is at least about 1:1 to no greater than about 1:10,000,000 in about 200 mM HEPES, about pH 7.5 at 37° C. for at least about 3 hours. The immunogenic composition can include an adjuvant.

The invention is also directed to a composition including an inhibitor of an isolated prolyl tripeptidyl-peptidase and a pharmaceutically acceptable carrier.

Additional aspects of the invention include a dipeptidyl peptidase having an amino acid sequence including SEQ ID NO:43, SEQ ID NO:44, or SEQ ID NO:45.

Definitions

"Polypeptide" as used herein refers to a polymer of amino acids and does not refer to a specific length of a polymer of amino acids. Thus, for example, the terms peptide, oligopeptide, protein, and enzyme are included within the definition of polypeptide. This term also includes post-expression modifications of the polypeptide, for example, glycosylations, acetylations, phosphorylations, and the like. A polypeptide can be produced by an organism, or produced using recombinant techniques, or chemically or enzymatically synthesized.

"Peptidase," "proteinase," and "protease" all refer to enzymes that catalyze the hydrolysis of peptide bonds in a polypeptide. A "peptide bond" or "amide bond" is a covalent bond between the alpha-amino group of one amino acid and the alpha-carboxyl group of another amino acid. "Peptidase inhibitor," "proteinase inhibitor," "protease inhibitor," and "inhibitor" all refer to molecules that inhibit a peptidase that catalyzes the hydrolysis of peptide bonds in a polypeptide.

As used herein, the term "isolated" means that a polypeptide or a nucleic acid fragment has been either removed from its natural environment, produced using recombinant techniques, or chemically or enzymatically synthesized. Preferably, the polypeptide or nucleic acid fragment is purified, i.e., essentially free from any other polypeptides or nucleic acid fragments and associated cellular products or other impurities.

"Amidolytic activity" refers to the ability of a polypeptide to catalyze the hydrolysis of at least one peptide bond in a polypeptide. The term "cleavage" can also be used to refer to the hydrolysis of a peptide bond in a polypeptide. "Prolyl-tripeptidyl peptidase" and "PTP" refer to a polypeptide having a particular "amidolytic activity". A "prolyl-tripeptidyl peptidase" is able to hydrolyze the peptide bond between the proline and the Yaa residues in a target polypeptide with the general formula $NH_2$-Xaa-Xaa-Pro-Yaa-(Xaa)$_n$ (SEQ ID NO:25), wherein Xaa is a natural or modified amino acid, Yaa is a natural or modified amino acid except proline, and the α-amino of the amino terminal residue is not blocked. A "prolyl tripeptidyl-peptidase" does not have to cleave all members of the target peptide. The term "natural amino acid" refers to the 20 amino acids typically produced by a cell. The term "modified amino acid" refers to, for instance, acetylation, hydroxylation, methylation, amidation, and the attachment of carbohydrate or lipid moieties, cofactors, and the like.

A "target polypeptide" is a polypeptide that is the potential substrate of the amidolytic activity of a prolyl tripeptidyl-peptidase.

An active analog, active fragment, or active modification of a polypeptide of the invention is one that has amidolytic activity by hydrolysis of a peptide bond present in the target polypeptide as described herein. Active analogs, fragments, and modifications are described in greater detail herein.

"Nucleic acid fragment" as used herein refers to a linear polymeric form of nucleotides of any length, either ribonucleotides or deoxynucleotides, and includes both double- and single-stranded DNA and RNA. A nucleic acid fragment may include both coding and non-coding regions that can be obtained directly from a natural source (e.g., a microorganism), or can be prepared with the aid of recombinant or synthetic techniques. A nucleic acid molecule may be equivalent to this nucleic acid fragment or it can include this fragment in addition to one or more other nucleotides or polynucleotides, For example, the nucleic acid molecule of the invention can be a vector, such as an expression of cloning vector.

"Percentage amino acid identity" refers to a comparison of the amino acids of two polypeptides as described herein.

BRIEF DESCRIPTION OF THE FIGURES

FIG. 3. Multiple sequence alignment of *P. gingivalis* PTP-A (PTP-A) and its bacterial and eukaryotic homologues. Pg-DPP, DPP from *P. gingivalis* (Kiyama, M., et al., (1998) *Bioch. Bioph. Acta* 1396, 39–46) containing an amino-terminal sequence corrected according to the *P. gingivalis* W83 genome data available from The Institute of Genomic Research on the World Wide Web at tigr.org); Fm-DPP, DPP from Flavobacterium meningosepticum; Hs-DPP, human DPP IV; and Mm-FAP, mouse fibroblast activation protein. Peptide sequences obtained from PTP-A analysis described herein are indicated with arrows (note that the sequence of the peptide 81–97 corresponds to the N-terminus of the lower molecular weight form of PTP-A); catalytic triad is marked with asterisks; and the proposed PTP-A membrane-anchoring N-terminal a-helix is double-underlined. Homologous regions (i.e., regions of identical amino acids and/or conservative substitutions) are highlighted. Identical regions are shown as white letters on a black background.

FIG. 4. Comparison of *P. gingivalis* PTP-A and DPP active site domains to corresponding sequences of three putative homologues identified within the *P. gingivalis* genome (DPP-H1, DPP-H2 and DPP-H3). Sequences of *P. gingivalis* PTP-A, DPP, DPP-H1, DPP-H2, and DPP-H3 were obtained from conceptual translation of the following open reading frames retrieved from The Institute for Genomic Research (TIGR) unfinished *P. gingivalis* genome database: gnl |TIGR| *P. gingivalis* contig 126 (positions 13 228–15 426), contig 87 (positions 6 424–4 399), contig 65 (positions 161–1 786), contig 101 (positions 8 895–6 845), and contig 9 (positions 4 216–2 162), respectively. Residues predicted as catalytic triads are marked with asterisks. Homologous regions (i.e., regions of identical amino acids and/or conservative substitutions) are highlighted. Identical regions are shown as white letters on a black background. Similar regions (i.e., conservative substitutions) are shown as white letters on a grey background.

DETAILED DESCRIPTION OF THE INVENTION

Figure 1A:
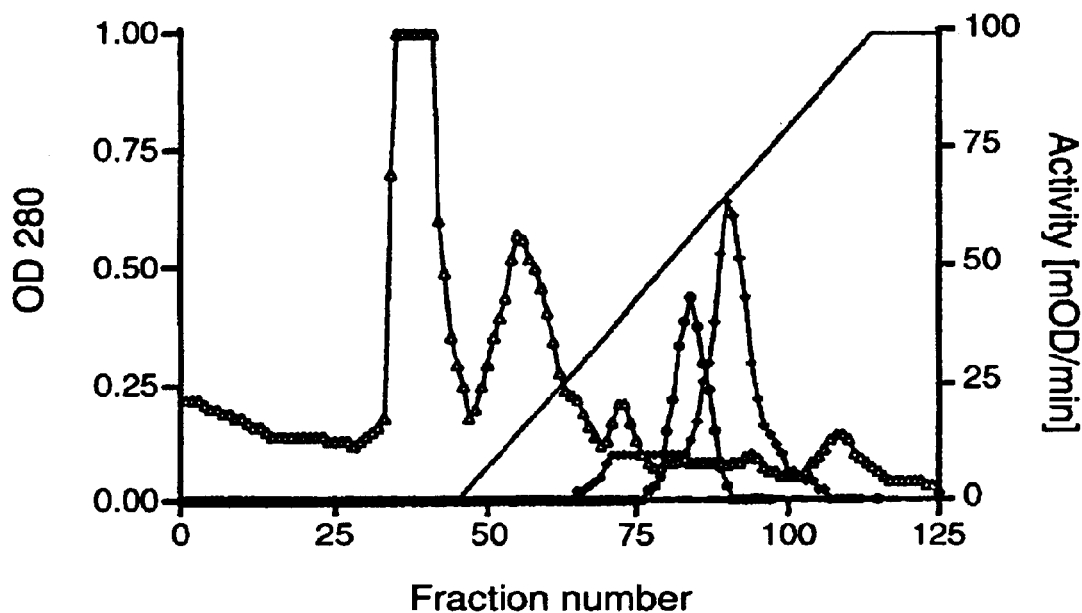
FIGS. 1A–D Purification of the prolyl tripeptidyl peptidase from the acetone precipitate of the *P. gingivalis* cell extracts. Absorbance at 280 nm (open triangles), amidolytic activity against H-Ala-Phe-Pro-pNA (closed diamonds), and H-Gly-Pro-pNA (closed circles). (a) Separation of PTP-A on hydroxyapatite. (b) Separation of PTP-A on Phenyl-Sepharose HP. (c) Separation of PTP-A on MonoQ FPLC. (d) Chromatofocusing of PTP-A on Mono-P.

The present invention provides isolated polypeptides, preferably isolated prolyl peptidases, more preferably prolyl dipeptidyl-peptidases and prolyl tripeptidyl-peptidases, most preferably prolyl-tripeptidyl peptidases, that have amidolytic activity by hydrolysis of a peptide bond present in a target polypeptide, where the bond is between a proline and an amino acid residue attached to the alpha-carboxyl group end of the proline.

When the prolyl peptidase is a prolyl tripeptidyl-peptidase, the peptidase has amidolytic activity by hydrolysis of a peptide bond present in a target polypeptide of the general formula $NH_2$-Xaa-Xaa-Pro-Yaa-(Xaa)$_n$ (SEQ ID NO:25), wherein Xaa is a natural or modified amino acid, Yaa is a natural or modified amino acid except proline, and the α-amino of the amino terminal residue is not blocked, wherein the peptide bond of the target polypeptide that is hydrolyzed is the Pro-Yaa peptide bond. Preferably, isolated polypeptides do not cleave a target peptide having a blocked α-amino of the amino terminal residue. Preferably, the only peptide bond of the target peptide that is hydrolyzed is the Pro-Yaa bond. In increasing order of preference, isolated polypeptides can cleave a target peptide that is at least 4 amino acids or at least 300 Da, at least 10 amino acids or at least 750 Da, at least 20 amino acids or at least 1,500 Da, or at least 30 amino acids or at least 3,000 Da. Preferably, the prolyl-tripeptidyl peptidases cleave peptides 1, 2, 7, 8, and 10–15 shown in Table 3, human cystatin C, and interleukin 6.

When the prolyl peptidase is a prolyl dipeptidyl-peptidase, the peptidase has amidolytic activity by hydrolysis of a peptide bond present in a target polypeptide of the general formula $NH_2$-Xaa-Zaa-Yaa-(Xaa)$_n$ (SEQ ID NO:12), wherein Xaa is a natural or modified amino acid, Zaa is a proline or alanine, Yaa is a natural or modified amino acid except proline or hydroxyproline, and the α-amino of the amino terminal residue is not blocked, wherein the peptide bond of the target polypeptide that is hydrolyzed is the Zaa-Yaa peptide bond. Preferably, isolated polypeptides does not cleave a target peptide having a blocked α-amino of the amino terminal residue. Preferably, the only peptide bond of the target peptide that is hydrolyzed is the Pro-Yaa bond.

Due to their cyclic aliphatic character proline residues bestow unique conformational constraints on polypeptide chain structures, significantly affecting the susceptibility of proximal peptide bonds to proteolytic cleavage. Those proline residues, which often appear near the amino-termini of many biologically active peptides, may protect them against proteolytic degradation by peptidases with general specificity. A specialized group of proteolytic enzymes, typically referred to as prolyl peptidases, has evolved to cleave (i.e., hydrolyze) a peptide bond adjacent to a proline residue in a polypeptide. The peptide bond adjacent to a proline residue can be referred to as a prolyl-X bond, where prolyl is the proline residue, and X is an amino acid residue attached to the alpha-carboxyl group end of the proline. The bacterial prolyl peptidases can cleave a polypeptide to liberate a tripeptide or a dipeptide. Prolyl peptidases that do not cleave a target peptide if the α-amino of the amino terminal residue is blocked can be referred to as exopeptidases. The in vivo activity of these specialized proteolytic enzymes may have important physiological significance, because it may lead to inactivation of many biologically active peptides and/or transformation of the activity of other biologically active peptides. In addition, hydrolysis of prolyl-X bonds in conjunction with general catabolic pathways should allow the complete reutilization of amino acids by living organisms, including bacteria. However, prolyl peptidases from bacterial pathogens, if released into the host environment, may interfere with the physiological functions of biologically active polypeptides and, therefore, contribute to the pathogenicity of infectious disease.

The external (i.e., cell surface) localization and uncontrolled activity of bacterial peptidases, including prolyl peptidases, likely contributes significantly to run-away inflammation in the human host and the pathological degradation of connective tissue during periodontitis. For instance, working in concert bacterial prolyl peptidases (e.g., prolyl tripeptidyl peptidases and DPP IV) have the ability to completely degrade collagen fragments locally generated by endogenous or bacterial collagenases. Because type I collagen is the major component of periodontal ligament, its enhanced degradation by bacterial prolyl peptidases may contribute to loss of tooth attachment and periodontal pocket formation. Thus, there is a need in the art to characterize bacterial peptidases to facilitate the development of therapies to inhibit the activity of the bacterial peptidases.

The polypeptides of the present invention, preferably prolyl peptidases, can be used as a source of antibodies for inhibiting the peptidase activity and thereby possibly reducing periodontitis, loss of tooth attachment and periodontal pocket formation. Antibodies to prolyl peptidases can also be used to identify and/or isolate additional prolyl peptidases. Knowledge of prolyl peptidases can also be used to make inhibitors of prolyl peptidases and to make immunogenic compositions that could be used to elicit the production of antibodies to prolyl peptidases and thereby possibly reduce gingivitis, periodontitis, loss of tooth attachment, and/or periodontal pocket formation.

An example of a prolyl-tripeptidyl peptidase is prolyl-tripeptidyl peptidase A (SEQ ID NO:30) (also referred to as PTP-A) from *P. gingivalis*. Purified PTP-A has apparent molecular masses of 81.8 and 75.8 kDa. The lower molecular mass peptidase may be due to the proteolytic cleavage of the peptidase from the surface of *P. gingivalis*. PTP-A is a new member of clan SC, family S9 of serine peptidases. Clans of serine peptidases are grouped on the basis of the order of certain amino acids in the polypeptide that make up the "catalytic triad" which plays a pivotal role peptidase activity. The members of the clan SC are characterized by the catalytic triad in the polypeptide in the order of serine, aspartic acid, and histidine. Members of the clan SC are also characterized by a tertiary structure including β/α/β units, and an α/β hydrolase fold. In addition to the catalytic triad order, the amino acid sequence GXSXXG (SEQ ID NO:39), where X is any amino acid and S is the active site serine, is a signature of all members of the clan SC with some distinguishing features specific for each family. Family S9 has the consensus sequence GXSXGG (SEQ ID NO:40). Besides this consensus sequence, there is a general similarity of primary structures which classifies peptidases to this family. For instance, peptidases of this family generally have two domains, an amino-terminal domain that contains a membrane binding domain, and a carboxy-terminal domain, also referred to as the catalytic domain. The catalytic domain contains the residues of the catalytic triad. Some members of the S9 family have only the catalytic domain.

The S9 family is diverged and divided in three subfamilies: S9A, cytosolic oligopeptidases from archae and eukaryotes; S9B, eukaryotic acylaminoacylpeptidases; and S9C, dipeptidyl peptidease IV from bacteria and eukaryotes. The catalytic domain of peptidases from family S9 typically begin at about residue 400 of SEQ ID NO:30 and include the remaining carboxy-terminal amino acids (see, e.g., Fulop, et al., (1998) *Cell* 94, 161–170). Despite structural similarities to peptidases from the S9 family, the tripeptidyl-peptidase activity of PTP-A is unusual for this family of enzymes, and no other known similar activity has so far been attributed to any other member of the S9 family. In fact, all strict tripeptidyl-peptidases belong only to the subtilisin family (S8) and S33 family of serine peptidases; however, they neither share a structural relationship with PTP-A nor have activity limited to cleavage after proline residues. In particular, there are no other known prolyl tripeptidyl peptidases with an activity that is increased by iodoacetamide relative to the same prolyl tripeptidyl peptidase in the absence of iodoacetamide under the same conditions. Iodoacetamide is a compound that is traditionally a peptidase inhibitor. Typically, the activity of a prolyl tripeptidyl peptidase is increased about two-fold. Furthermore, unlike oligopepidases, the prolyl tripeptidyl-peptidases of the present invention can cleave target peptides having as few as 4 amino acids but also target peptides having at least 30 amino acids or a molecular weight of at least 3,000 Da. In these respects, the *P. gingivalis* tripeptidyl peptidase is a unique enzyme, and the isolation and characterization of this novel bacterial prolyl peptidase will facilitate the development of therapies to inhibit the activity of the bacterial peptidases.

Examples of putative prolyl-dipeptidyl peptidases are DPP-H1 (SEQ ID NO:43), DPP-H2 (SEQ ID NO:44), and DPP-H3 (SEQ ID NO:45). These peptidases have a significant percentage amino acid similarity with DPP IV and PTP-A (see FIG. 6). Each dipeptidyl peptidase is expected to have enzymatic activity, as each has a well preserved catalytic triad (FIG. 4). DPP IV has been characterized and the gene encoding the peptidase has been cloned, however the substrate specificity has not been well characterized. DPP IV has been found to cleave SEQ ID NOs:6, 20, 23, and 24. DPP IV has been purified in two forms. One of the forms is a full length gene translation product containing a blocked amino-terminal residue. The second form had the amino-terminal amino acid sequence HSYRAAVYDYDVRRN-LVKPLSEHVG (SEQ ID NO:48), which corresponds to residues 116–140 of DPP IV (Kiyama, M., et al. (1998) *Biochin Biophys. Acta* 1396, 39–46), indicating that it was proteolytically truncated on the amino-terminus.

In *P. gingivalis*, PTP-A and DPP IV activity is cell surface associated. While not intending to be limiting, it is conceivable that the enzyme is membrane anchored through a putative signal sequence which is not cleaved but remains as a membrane spanning domain similar to other members of the prolyl oligopeptidase family. However, a significant portion of the purified PTP-A has a truncated N-terminus, apparently due to cleavage by Lys-specific peptidase and likely to be an artifact which has occurred during the purification procedure. Nevertheless, membrane bound PTP-A and DPP IV is proteolytically cleaved and shed during cultivation of the bacteria, as indicated by variable amount of soluble activities found in cell free culture media. The cell surface localization of PTP-A supports a putative physiological function in providing nutrients for growing bacterial cells. The inability of asaccharolytic *P. gingivalis* to utilize free amino acids makes the bacterium entirely dependant on an external peptide supply. In this regard, PTP-A and DPP IV activities are probably very important, if not indispensable, for bacterial growth, and inhibition of prolyl tripeptidyl-peptidases and dipeptidyl-peptidases may inhibit the in vivo growth of organisms, including *P. gingivalis*. For instance, treatment of *P. gingivalis* cultures in lagphase (i.e., the period after inoculation of a culture and before the organism begins to divide) and early logarithmic growth with the inhibitors PEFABLOCK and 3,4-dichloroisocoumarin inhibits growth of *P. gingivalis*.

Preferably, a polypeptide of the invention, preferably a prolyl peptidase, contains the amino acid sequence GXSXXG (SEQ ID NO:39), most preferably, GXSXGG (SEQ ID NO:40), where G is glycine, X is any amino acid, and S is the active site serine. The active site serine can be identified by, for instance, labeling with diisopropylfluorophosphate as described herein. Preferably, the catalytic domain of the prolyl tripeptidyl-peptidases of the invention begins at about residue 400 of SEQ ID NO:30 and includes the remaining carboxy-terminal amino acids and the corresponding amino acids of SEQ ID NOs:43–45 (see FIG. 6), more preferably, at about residue 502 of SEQ ID NO:30 and includes the remaining carboxy-terminal amino acids and the corresponding amino acids of SEQ ID NOs:43–45 (see FIG. 6), most preferably, at about residue 556 of SEQ ID NO:30 and includes the remaining carboxy-terminal amino acids and the corresponding amino acids of SEQ ID NOs:43–45 (see FIG. 6).

The invention further includes a polypeptide, preferably a prolyl tripeptidyl-peptidase, that shares a significant level of primary structure with SEQ ID NO:30. The two amino acid sequences (i.e., the amino acid sequence of the polypeptide and the sequence SEQ ID NO:30) are aligned such that the residues that make up the catalytic triad, i.e., the serine, aspartic acid, and the histidine, are in register, then further aligned to maximize the number of amino acids that they have in common along the lengths of their sequences; gaps in either or both sequences are permitted in making the alignment in order to place the residues of the catalytic triad in register and to maximize the number of shared amino acids, although the amino acids in each sequence must nonetheless remain in their proper order. The percentage amino acid identity is the higher of the following two numbers: (a) the number of amino acids that the two sequences have in common within the alignment, divided by the number of amino acids in SEQ ID NO:30, multiplied by 100; or (b) the number of amino acids that the two sequences have in common within the alignment, divided by the number of amino acids in the candidate polypeptide, multiplied by 100. Preferably, a prolyl tripeptidyl peptidase has greater than 35% identity, more preferably at least about 40% identity, most preferably at least about 45% identity with SEQ ID NO:30. Preferably, amino acids 154–732 of SEQ ID NO:30 are used, more preferably amino acids 400–732 of SEQ ID NO:30 are used. An isolated polypeptide comprising an amino acid sequence having a percentage amino acid identity of greater than 35% with SEQ ID NO:30.

In general, the amidolytic activity of the polypeptides of the invention, preferably prolyl peptidases, can be measured by assay of the cleavage of a target polypeptide in the presence of prolyl peptidase and a buffer. Preferably, the lower ratio of prolyl tripeptidyl-peptidase to target polypeptide is at least about 1:1, more preferably at least about 1:100, even more preferably at least about 1:1,000, most preferably at least about 1:10,000. Preferably, the higher ratio of prolyl peptidase to target polypeptide is no greater than about 1:10,000,000, more preferably no greater than about 1:1,000,000 and most preferably no greater than about 1:100,000. Buffers in which a prolyl peptidase is active are suitable for the assay. Preferably, the buffer is about 200 mM HEPES (N-2-hydroxyethylpeperazine,N'-2-ethansulfonic acid), more preferably about 50 mM HEPES, most preferably about 20 mM HEPES. Preferably, the pH of the buffer is at least about pH 6.0 and no greater than pH 8.0, more preferably about pH 7.5. Preferably, the temperature of the assay is at about 37° C. The assay can be carried out for at least about 1 minute to no greater than 24 hours. Preferably, the amidolytic activity of the prolyl peptidases are measured at a prolyl peptidase:target polypeptide ratio of at least about 1:100 to no greater than 1:1,000,000 in about 200 mM HEPES, about pH 7.5 at about 37° C. for at least about 3 hours. In general, the time of the assay can vary depending on the substrate and enzyme:substrate ratio. Typically, target peptides are stable under these conditions, and typically it is difficult to detect background levels of hydrolysis in the absence of a prolyl peptidase. Preferably, the assay is allowed to continue until at least 1% of the target peptide is hydrolyzed.

Prolyl-tripeptidyl peptidases of the present invention preferably are inhibited by a compound chosen from the group consisting of PEFABLOCK (4-(2-aminoethyl)-benzenesulfonyl-fluoride hydrochloride), diisopropylfluorophosphate, and 3,4-dichloroisocoumarin, more preferably PEFABLOCK and diisopropylfluorophosphate, and most preferably diisopropylfluorophosphate. The peptidases of the present invention are preferably not inhibited by a compound chosen from the group consisting of leupeptin, antipain, E-64, pepstatin, $\alpha_1$-proteinase inhibitor, $\alpha_1$-antichymotrypsin and $\alpha_2$-macroglobulin, most preferably. Significantly and unexpectedly, the amidolytic activity of a prolyl-tripeptidyl peptidase of the present invention is increased by iodoacetamide relative to the prolyl-tripeptidyl peptidase in the absence of iodoacetamide under the same conditions. Preferably, the effect of iodoacetamide on amidolytic activity is measured by incubating in 200 mM HEPES, pH 7.6, at least about 0.1 nM of the prolyl tripeptidyl-peptidase with the inhibitor for about 15 minutes, adding about 1 mM of H-Ala-Phe-Pro-pHA, and incubating for at least about 1 minute before assaying for amidolytic activity. Typically, at least about 1 mM to no greater than 100 mM of inhibitor is used.

The polypeptides of the invention include a polypeptide having SEQ ID NO:30, or an active analog, active fragment, or active modification of SEQ ID NO:30. An active analog, active fragment, or active modification of a polypeptide having SEQ ID NO:30 is one that has amidolytic activity by hydrolysis of the Pro-Yaa peptide bond present in a target polypeptide of the general formula $NH_2$-Xaa-Xaa-Pro-Yaa-$(Xaa)_n$ (SEQ ID NO:25). Active analogs of a polypeptide having SEQ ID NO:30 include prolyl-tripeptidyl peptidases having amino acid substitutions that do not eliminate hydrolysis of SEQ ID NO:25 at the Pro-Yaa peptide bond. Substitutes for an amino acid may be selected from other members of the class to which the amino acid belongs. For example, nonpolar (hydrophobic) amino acids include alanine, leucine, isoleucine, valine, proline, phenylalanine, tryptophan, and tyrosine. Polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Examples of preferred conservative substitutions include Lys for Arg and vice versa to maintain a positive charge; Glu for Asp and vice versa to maintain a negative charge; Ser for Thr so that a free —OH is maintained; and Gln for Asn to maintain a free $NH_2$.

Active fragments of a prolyl-tripeptidyl peptidase of the invention include prolyl-tripeptidyl peptidases containing deletions or additions of one or more contiguous or non-contiguous amino acids such that the resulting polypeptide will hydrolyze SEQ ID NO:25 at the Pro-Yaa peptide bond. An example of a fragment of a prolyl-tripeptidyl peptidase is a catalytic domain. Modified prolyl-tripeptidyl peptidases include prolyl-tripeptidyl peptidases that are chemically and enzymatically derivatized at one or more constituent amino acid, including side chain modifications, backbone modifications, and N- and C-terminal modifications including acetylation, hydroxylation, methylation, amidation, and the attachment of carbohydrate or lipid moieties, cofactors, and the like. Modified prolyl-tripeptidyl peptidases will hydrolyze SEQ ID NO:25 at the Pro-Yaa peptide bond.

Prolyl peptidases can be obtained by several methods. Isolation of a prolyl-tripeptidyl peptidase present on the surface of a cell producing the peptidase typically requires lysis of the cell followed by purification methods that are well known in the art. Alternatively, cels can be treated with a detergent, for instance Triton X-100, to remove the peptidase from the cell surface. The following are nonlimiting examples of suitable protein purification procedures: fractionation on immunoaffinity, ion-exchange, hydroxyapatite, Phenyl-Sepharose HP, MonoQ HR 5/5, or MonoP columns; ethanol precipitation; reverse phase HPLC; chromatography on silica or on an ion-exchange resin such as DEAE; chromatofocusing; SDS-PAGE; ammonium sulfate precipitation; gel filtration using, for example, Sephadex G-75. Preferably, isolation of a prolyl-tripeptidyl peptidase from *P. gingivalis* is accomplished using a combination of hydroxyapatite, Phenyl-Sepharose HP, MonoQ HR 5/5 and MonoP column chromatography steps as described herein.

Prolyl peptidases can also be isolated from organisms other than *P. gingivalis*. Other organisms can express a prolyl-tripeptidyl peptidase that is encoded by a coding region having similarity to the PTP-A coding region. A "coding region" is a linear form of nucleotides that encodes a polypeptide, usually via mRNA, when placed under the control of appropriate regulatory sequences. The boundaries of a coding region are generally determined by a translation start codon at its 5' end and a translation stop codon at its 3' end. "Regulatory region" refers to a nucleic acid fragment that regulates expression of a coding region to which a regulatory region is operably linked. Non limiting examples of regulatory regions include promoters, transcription initiation sites, translation start sites, translation stop sites, and terminators. "Operably linked" refers to a juxtaposition wherein the components so described are in a relationship permitting them to function in their intended manner. A regulatory element is "operably linked" to a coding region when it is joined in such a way that expression of the coding region is achieved under conditions compatible with the regulatory region. Alternatively, other organisms can express a prolyl-tripeptidyl peptidase from a recombinant coding region encoding the peptidase. The identification of similar coding regions in other organisms can be accomplished as described herein. A prolyl-tripeptidyl peptidase can be isolated using purification methods that are well known in the art. Alternatively, the peptidase can be chemically synthesized using methods that are well known in the art including, for instance, solid phase synthesis. Examples of, for instance, coding and regulatory regions are described herein.

The expression of a prolyl-tripeptidyl peptidase by an organism other than *P. gingivalis* can be detected using specific substrates of the general formula $NH_2$-Xaa-Xaa-Pro-LG or $NH_2$-Xaa-Xaa-Pro-Yaa (SEQ ID NO:41), where LG is a leaving group. The leaving group can be a chromogenic or fluorogenic group known to the art. The expression of a prolyl-tripeptidyl peptidase by an organism and subsequent cleavage of a specific substrate results in a free amino acid or a free leaving group, each of which can be assayed using techniques known to those of skill in the art. Other methods can be based on immunogenic properties of PTP-A, for instance immunoassays and histochemistry, the detection of mRNA, and PCR related methods, all of which are known to one of skill in the art.

As described in the Examples, the amino acid sequence of the amino-terminal end of a PTP-A fragment was used to identify the nucleotide sequence of the PTP coding region. The nucleotide sequence was present in a publically available database containing the nucleotide sequence of the partially finished *P. gingivalis* W83 genome. However, even though the nucleotides that encode the *P. gingivalis* PTP-A were known, there was no indication that the nucleotides were in fact transcribed and translated. The data obtained from the database only contained the nucleotide sequence of a genomic clone; there was no disclosure that the nucleotides did or did not contain an open reading frame. Moreover, there is little data known to the art regarding regulatory regions required for either the transcription or the translation of a nucleotide sequence in *P. gingivalis*.

Thus, a person of ordinary skill, having the nucleotide sequence of the genomic clone, would not be able to predict that the open reading frame encoding PTP-A was transcribed or translated. Moreover, even if there was a suggestion that the open reading frame was both transcribed and translated, there is no suggestion that the polypeptide encoded by the open reading frame would have the novel activity of PTP-A.

Accordingly, the present invention is directed to a nucleic acid fragment encoding a polypeptide, particularly a prolyl-tripeptidyl peptidase, active analog, active fragment, or active modification thereof. The nucleic acid fragment can have a nucleotide sequence as shown in SEQ ID NO:38. Alternatively, nucleic acid fragments of the invention include those whose complement hybridize to SEQ ID NO:38 under standard hybridization conditions as described herein. During hybridization the entire nucleotide sequence of the complement can hybridize with SEQ ID NO:38. Preferably, at least about 20 nucleotides of the complement hybridize with SEQ ID NO:38, more preferably at least about 50 nucleotides, most preferably at least about 100 nucleotides.

Alternatively, the nucleic acid fragment can have a nucleotide sequence encoding a polypeptide having the amino acid sequence shown in SEQ ID NO:30. An example of the class of nucleotide sequences encoding such a polypeptide is SEQ ID NO:38. This class of nucleotide sequences is large but finite, and the nucleotide sequence of each member of the class can be readily determined by one skilled in the art by reference to the standard genetic code.

The identification of similar coding regions in other organisms can be accomplished by screening individual wild-type microorganisms for the presence of nucleotide sequences that are similar to the coding region of PTP-A, which is shown in SEQ ID NO:38. Screening methods include, for instance, hybridization of a detectably labeled probe with a nucleic acid fragment.

Standard hybridizing conditions are a modification of the conditions used by Church et al. ((1984) Proc. Natl. Acad. Sci. USA 81, 1991): 0.5 M phosphate buffer, pH 7.2, 7% SDS, 10 mM EDTA, at 68° C., and three washes, each for 20 minutes in 2×SSC, 0.1% SDS, at 65° C. Preferably, a probe will hybridize to the nucleotide sequence set forth in SEQ ID NO:38 under standard hybridizing conditions. Generally the probe does not have to be complementary to all the nucleotides of the nucleic acid fragment as long as there is hybridization under the above-stated conditions.

"Complement" and "complementary" refer to the ability of two single stranded nucleic acid fragments to base pair with each other, where an adenine on one nucleic acid fragment will base pair to a thymine on a second nucleic acid fragment and a cytosine on one nucleic acid fragment will base pair to a guanine on a second nucleic acid fragment. Two nucleic acid fragments are complementary to each other when a nucleotide sequence in one nucleic acid fragment can base pair with a nucleotide sequence in a second nucleic acid fragment. For instance, 5'-ATGC and 5'-GCAT are complementary. The term complement and complementary also encompasses two nucleic acid fragments where one nucleic acid fragment contains at least one nucleotide that will not base pair to at least one nucleotide present on a second nucleic acid fragment. For instance the third nucleotide of each of the two nucleic acid fragments 5'-ATTGC and 5'-GCTAT will not base pair, but these two nucleic acid fragments are complementary as defined herein. Typically two nucleic acid fragments are complementary if they hybridize under the standard conditions referred to herein.

Preferred probes are nucleic acid fragments complementary to a coding region or another nucleotide sequence that encodes a prolyl-tripeptidyl peptidase. For instance, a probe can comprise a consecutive series of nucleotides complementary to a portion of SEQ ID NO:38. Preferably a probe is at least about 18 bases, more preferably at least about 21 bases, and most preferably at least about 24 bases in length. Particularly preferred probes are

TTCGATCCGGCAAAGAAATATCCTGTTATTGT-CTATGTTTACGGAGGAC CT (SEQ ID NO:36,

GTGGATGCCGATAGAATAGGAGTACATG-GCTGGAGCTATGGTGGCTTT (SEQ ID NO:37, and SEQ ID NO:38. Methods of detectably labeling a probe are well known to the art.

The nucleic acid fragment that is identified by the probe is further analyzed to determine if it encodes a polypeptide with amidolytic activity of the Pro-Yaa peptide bond on a target polypeptide of the general formula $NH_2$-Xaa-Xaa-Pro-Yaa-(Xaa)$_n$ (SEQ ID NO:25). Another method for screening individual microorganisms for the presence of nucleotide sequences that are similar to the coding regions of the present invention is the polymerase chain reaction (PCR).

Individual wild-type microorganisms containing nucleic acid fragments encoding a prolyl-tripeptidyl peptidase can also be identified using antibody. Preferably the antibody is directed to PTP-A. The production of antibodies to a particular polypeptide is known to a person of skill in the art, and is further detailed herein.

The use of hybridization of a probe to a coding region present in individual wild-type microorganisms can be used as a method to identify a coding region identical or similar to a coding region present in SEQ ID NO:38. The coding region can then be isolated and ligated into a vector as described below. Two nucleic acid sequences are "similar" if the two nucleic acid sequences can be aligned so that the number of identical amino acids along the lengths of their sequences are optimized. Preferably, two nucleotide acid sequences have, in increasing order of preference, preferably at least about 90%, at least about 92%, at least about 94%, at least about 96%, most preferably at least about 98% identity.

As mentioned above, a nucleic acid fragment of the invention can be inserted in a vector. Construction of vectors containing a nucleic acid fragment of the invention employs standard ligation techniques known in the art. See, e.g., Sambrook et al, Molecular Cloning: A Laboratory Manual., Cold Spring Harbor Laboratory Press (1989) or Ausubel, R. M., ed. Current Protocols in Molecular Biology (1994). A vector can provide for further cloning (amplification of the nucleic acid fragment), i.e., a cloning vector, or for expression of the polypeptide encoded by the coding region, i.e., an expression vector. The term vector includes, but is not limited to, plasmid vectors, viral vectors, cosmid vectors, or artificial chromosome vectors. Typically, a vector is capable of replication in a bacterial host, for instance E. coli. Preferably the vector is a plasmid.

Selection of a vector depends upon a variety of desired characteristics in the resulting construct, such as a selection marker, vector replication rate, and the like. Suitable plasmids for expression in E. coli, for example, include pUC(X), pKK223-3, pKK233-2, pTrc99A, and pET-(X) wherein (X) denotes a vector family in which numerous constructs are available. pUC(X) vectors can be obtained from Pharmacia Biotech (Piscataway, N.H.) or Sigma Chemical Co. (St. Louis, Mo.). pKK223-3, pKK233-2 and pTrc99A can be obtained from Pharmacia Biotech. pET-(X) vectors can be obtained from Promega (Madison, Wis.) Stratagene (La Jolla, Calif.) and Novagen (Madison, Wis.). To facilitate replication inside a host cell, the vector preferably includes an origin of replication (known as an "ori") or replicon. For example, ColE1 and P15A replicons are commonly used in plasmids that are to be propagated in E. coli.

An expression vector optionally includes regulatory regions operably linked to the coding region. The invention is not limited by the use of any particular promoter, and a wide variety are known. Promoters act as regulatory signals that bind RNA polymerase in a cell to initiate transcription of a downstream (3' direction) coding region. The promoter used in the invention can be a constitutive or an inducible promoter. It can be, but need not be, heterologous with respect to the host cell. Preferred promoters for bacterial transformation include lac, lacUV5, tac, trc, T7, SP6 and ara.

An expression vector can optionally include a Shine Dalgarno site (e.g., a ribosome binding site), and a start site (e.g., the codon ATG) to initiate translation of the transcribed message to produce the enzyme. It can also include a termination sequence to end translation. A termination sequence is typically a codon for which there exists no corresponding aminoacetyl-tRNA, thus ending polypeptide synthesis. The nucleic acid fragment used to transform the host cell can optionally further include a transcription termination sequence. The rrnB terminators, which is a stretch of DNA that contains two terminators, T1 and T2, is an often used terminator that is incorporated into bacterial expression systems (J. Brosius et al., (1981) *J. Mol. Biol.* 148 107–127).

The nucleic acid fragment used to transform the host cell optionally includes one or more marker sequences, which typically encode a polypeptide that inactivates or otherwise detects or is detected by a compound in the growth medium. For example, the inclusion of a marker sequence can render the transformed cell resistant to an antibiotic, or it can confer compound-specific metabolism on the transformed cell. Examples of a marker sequence are sequences that confer resistance to kanamycin, ampicillin, chloramphenicol, and tetracycline.

Antibodies can be produced to a polypeptide having the sequence of SEQ ID NOs:30, 43, 44 or 45, or a polypeptide having a percentage amino acid identity as described herein. Alternatively, antibodies can be made to an antigenic analog, antigenic fragment, or antigenic modification of a polypeptide having the sequence of SEQ ID NOs:30, 43, 44 or 45. An antigenic analog, antigenic fragment, or antigenic modification of a polypeptide having SEQ ID NOs:30, 43, 44 or 45 is one that generates an immune response in an animal. Antigenic analogs of a polypeptide having SEQ ID NOs:30, 43, 44 or 45 include prolyl peptidases having amino acid substitutions that do not eliminate peptide antigenicity in an animal. Substitutes for an amino acid may be selected from other members of the class to which the amino acid belongs, as described herein. Fragments of a prolyl peptidase of the invention include prolyl peptidases containing deletions or additions of one or more contiguous or noncontiguous amino acids such that the resulting polypeptide will generate an immune response in an animal. An example of a fragments of a prolylpeptidase is a catalytic domain. Modified prolyl peptidases include prolyl peptidases that are chemically and enzymatically derivatized at one or more constituent amino acids, including side chain modifications, backbone modifications, and N- and C-terminal modifications including acetylation, hydroxylation, methylation, amidation, and the attachment of carbohydrate or lipid moieties, cofactors, and the like.

Accordingly, an aspect of the invention is an immunogenic composition comprising an isolated prolyl peptidase, or an antigenic analog, antigenic fragment, or antigenic modification thereof, preferably a prolyl tripeptidyl-peptidase. The prolyl tripeptidyl-peptidase preferably has amidolytic activity for cleavage of the Pro-Yaa peptide bond present in a target polypeptide with the general formula $NH_2$-Xaa-Xaa-Pro-Yaa-(Xaa)$_n$ (SEQ ID NO:25), wherein the amidolytic activity is measured at a prolyl tripeptidyl-peptidase:target polypeptide ratio of at least about 1:100 to no greater than about 1:1,000,000 in about 200 mM HEPES, about pH 7.5 at 37° C. for at least about 3 hours.

The immunogenic composition can further include excipients or diluents that are pharmaceutically acceptable as carriers and compatible with the immunogenic composition. The term "pharmaceutically acceptable carrier" refers to a carrier(s) that is "acceptable" in the sense of being compatible with the other ingredients of a composition and not deleterious to the recipient thereof. Suitable excipients are, for example, water, saline, dextrose, glycerol, ethanol, or the like, and combinations thereof. In addition, if desired, the immunogenic composition may contain minor amounts of auxiliary substances such as wetting or emulsifying agents, pH buffering agents, and/or adjuvants which enhance the effectiveness of the immune-stimulating composition.

The immunogenic composition can be used in a method for protecting an animal from a disease caused by *P. gingivalis*. This method includes administering the immunogenic composition and eliciting antibodies to a prolyl peptidase, antigenic analog, antigenic fragment, or antigenic modification. The diseases that can be treated in this manner include periodontal diseases, which includes gingivitis and periodontitis. Clinical hallmarks of periodontitis include lose of tooth attachment and periodontal pocket formation.

Alternatively and preferably, periodontal diseases can be treated by the use of inhibitors of a prolyl peptidase. An inhibitor of a prolyl peptidase, preferably a prolyl tripeptidyl-peptidase, can be present in a composition that preferably contains a pharmaceutically acceptable carrier. For instance, inhibitors can be applied systemically, subgingivally (e.g., subgingival irrigation) and/or by controlled release delivery directly into the periodontal pocket using methods well known to the art (see, e.g., Kornman, K., (1993) *J. Periodontol.* 64, 782–791). Preferably, an inhibitor is applied subgingivally or by controlled release delivery.

The prolyl peptidases, active analogs, fragments, and modifications thereof can be used in a method of reducing growth of bacteria in vitro or in vivo. Preferably, the bacteria is a periodontal pathogen, i.e, a bacterial pathogen that causes periodontal disease, more preferably the bacteria is *P. gingivalis*. The inability of asaccharolytic *P. gingivalis* to utilize free amino acids makes the bacterium entirely dependant on an external peptide supply. The action of the polypeptides of the invention may be required for bacterial growth, and inhibition of the polypeptides of the invention may inhibit the in vivo growth of organisms, including *P. gingivalis*. The method includes decreasing the amount of dipeptides and/or tripeptides (e.g., the result of cleavage of SEQ ID NO:25 by a prolyl-tripeptidyl peptidase) and the amount of free amino acids that result from further cleavage of the dipeptides and/or tripeptides present by inhibiting a prolyl peptidase, active analog, active fragment, or active modification thereof, such that the amount of dipeptides and/or tripeptides generated by the polypeptides is decreased. The amount of dipeptides and/or tripeptides is decreased relative to the amount of dipeptides and/or tripeptides present in the absence of the inhibitor. Preferably, the amount of dipeptides and/or tripeptides generated is decreased by an inhibitor, a monoclonal antibody that inhibits the prolyl peptidase, or polyclonal antibodies that inhibit the prolyl peptidase, more preferably, the amount of dipeptides and/or tripeptides generated is decreased by an inhibitor. Preferably, an inhibitor acts to inhibit a polypeptide of the invention, preferably a prolyl peptidase, by blocking the active site of the polypeptide. The polypeptide can be present on the surface of the bacteria or secreted into the environment, preferably the polypeptide is present in the surface of the bacteria.

The present invention is also directed to a method of developing an inhibitor of a prolyl peptidase, active analog, active fragment, or active modification thereof, preferably a prolyl-tripeptidyl peptidase. The method includes identifying a molecule that inhibits the amidolytic activity of the prolyl peptidase. This can be accomplished by, for instance, incubating the prolyl peptidase with a candidate molecule under conditions that promote amidolytic activity of the prolyl peptidase and determining if the amidolytic activity of the prolyl peptidase is decreased relative to the amidolytic activity in the absence of the molecule. The amidolytic activity can be measured by cleavage of the Pro-Yaa peptide bond present in the target polypeptide SEQ ID NO:25 as described herein. One method of developing an inhibitor includes using the target peptide SEQ ID NO:25 and replacing the Xaa residues with modified amino acids. It is expected that some modified amino acids will cause the target peptide to act as an inhibitor.

EXAMPLES

The present invention is illustrated by the following examples. It is to be understood that the particular examples, materials, amounts, and procedures are to be interpreted broadly in accordance with the scope and spirit of the invention as set forth herein.

Example 1

Materials

Diisopropylfluorophosphate (DFP), leupeptin and 3,4-dichloroisocoumarin, were purchased from Calbiochem (La Jolla, Calif.). Antipain, iodoacetamide, substance P, bradykinin and bradykinin related peptides, were obtained from Sigma. Other peptides used in this study were synthesized at the Molecular Genetic Instrumental Facility (University of Georgia, Athens, Ga.) using Fmoc protocol with an advanced ChemTech MPS350 automated synthesizer. H-Ala-Phe-Pro-pNA, H-Gly-Pro-pNA, Z-Gly-Pro-pNA, Z-Ala-Pro-pNA, and H-Pro-pNA (where pNA is p-Nitroanilide; Z is benzyloxycarbonyl; and H is hydrogen and denotes an unblocked amino-terminal group) were obtained from Bachem (King of Prussia, Pa.). Prolinal was kindly provided by Dr. James Powers (Georgia Institute of Technology, Atlanta) and cystatin C by Dr. Magnus Abrahamson (University of Lund, Sweden).

Methods

Source and Cultivation o Bacteria—*P. gingivalis* HG66 was obtained from Dr. Roland Arnold (University of North Carolina, Chapel Hill), while the strains W50 (ATCC 53978) and ATCC 33277 were obtained from the ATCC. All cells were grown as described previously (Chen, Z., et al., (1992) *J. Biol. Chem.* 267, 18896–18901).

Enzyme Activity Assays—Routinely, the tripeptidyl peptidase amidolytic activity was measured with H-Ala-Phe-Pro-pNA (1 mM) in 0.2 M HEPES (N-2-hydroxyethylpeperazine,N'-2-ethansulfonic acid), pH 7.5 at 37° C. The concentration of enzyme was 0.1 nM to 1 nM. The assay was performed in a total volume of 0.2 ml on microplates, and the initial turnover rate was recorded at 405 nm using a microplate reader (Spectramax Molecular Devices, Sunnyvale, Calif.). In inhibition studies, the enzyme was first preincubated with inhibitor for 15 min at 37° C., substrate added, and residual activity recorded after 5 minutes to 30 minutes. H-Gly-Pro-pNA, Z-Ala-Pro-pNA, Z-Gly-Pro-pNA and H-Pro-pNA (1 mM final concentration) were assayed in the same manner.

Protein Determination—Protein concentration was determined using the BCA reagent kit (Sigma, St. Louis, Mo.), using bovine serum albumin as a standard.

Localization of Tripeptidyl-Peptidase Activity—Cultures of *P. gingivalis* HG66, W50 and ATCC 33277, at different phases of growth, were subjected to the following fractionation procedure. The cells were removed by centrifugation (10,000×g, 30 minutes), washed twice with 10 mM Tris, 150 mM NaCl, pH 7.4, resuspended in 50 mM Tris, pH 7.6, and disintegrated by ultrasonication in an ice bath at 1500 Hz for 5 cycles (5 minutes sonication/5 minutes brake). Unbroken cells and large debris were removed by centrifugation (10,000×g, 30 minutes) and the opalescent supernatant subjected to ultracentrifugation (150,000×g, 120 minutes), yielding a pellet containing bacterial membranes and a supernatant which was considered as membrane-free cell extract. All fractions, as well as the full culture, culture medium, and full culture after sonication, were assayed for amidolytic activity against H-Ala-Phe-Pro-pNA.

Enzyme Purification—All purification steps were performed at 4° C. except for FPLC separations, which were carried out at room temperature. Cells were harvested by centrifugation (6,000×g, 30 minutes), washed with 50 mM potassium phosphate buffer, pH 7.4, and resuspended in the same buffer (150 ml per 50 gram of cells wet weight). Triton X-100 (10% volume/volume in $H_2O$) was added slowly to the bacterial cell suspension to a final concentration of 0.05%. After 120 minutes of gentle stirring, unbroken cells were removed by centrifugation (28,000×g, 60 minutes). Proteins in the supernatant were precipitated with cold acetone (−20° C.) added to a final concentration of 60% and collected by centrifugation. The pellet was redissolved in 50 mM potassium phosphate buffer, pH 7.0, and extensively dialyzed against 20 mM potassium phosphate, pH 7.0, containing 0.02% sodium azide. The dialyzed fraction was clarified by centrifugation (28,000×g, 30 min) and applied to a hydroxyapatite column (BioRad, Melville, N.Y.) equilibrated with 20 mM potassium phosphate, pH 7.0, at a flow rate of 20 ml/hour. After equilibration, the column was washed until the $A_{280}$ fell to zero. Bound proteins were eluted with a gradient from 20–300 mM potassium phosphate and fractions (7 ml) analyzed for dipeptidyl- and tripeptidyl-peptidase activity using H-Gly-Pro-pNA and H-Ala-Phe-Pro-pNA, respectively. The activity against the latter substrate was pooled, saturated with 1 M ammonium sulfate, clarified by centrifugation, and directly loaded onto a Phenyl-Sepharose HP (Pharmacia, Piscataway, N.J.) column equilibrated with 50 mM potassium phosphate, pH 7.0, containing 1 M ammonium sulfate. The column was washed with two volumes of equilibration buffer, followed by buffer containing 0.5 M ammonium sulfate, and developed with a descending gradient of ammonium sulfate from 0.5 to 0 M. Active fractions were pooled, extensively dialyzed against 20 mM Tris, pH 7.5, and applied to a MonoQ HR 5/5 FPLC column equilibrated with the same buffer. The column was washed with 5 volumes of equilibration buffer at 1.0 ml/minute, following which bound proteins were eluted with a gradient of 0–300 mM NaCl. The active fractions were pooled, dialyzed against 25 mM Bis-Tris, pH 6.3, and subjected to chromatofocusing on a MonoP FPLC column equilibrated with Bis-Tris buffer, using a pH gradient developed with 50 ml of 10×diluted Polybuffer 74 (Pharmacia), adjusted to a pH of 4.0.

Electrophoretic Techniques—The SDS-PAGE system of Schagger and von Jagow (Schagger, H., and von Jagow, G. (1987) *Anal. Biochem.* 166, 368–379), was used to monitor enzyme purification and estimate the enzyme molecular mass. For amino-terminal sequence analysis, proteins resolved in SDS-PAGE were electroblotted to polyvinylidene difluoride membranes using 10 mM CAPS, pH 11, 10% methanol (Matsudaira, P. (1987) *J. Biol. Chem.* 262, 10035–10038). The membrane was washed thoroughly with water and stained with Coomasie Blue G250. The blot was air dried, and protein bands cut out and subjected to $NH_2$-terminal sequence analysis with an Applied Biosystems 491 Protein Sequencer using the program designed by the manufacturers.

Enzyme Fragmentation—The purified prolyl tripeptidyl peptidase (PTP-A) was partially denatured by incubation in 6 M urea in 0.02 M Tris, pH 7.6, for 60 minutes. Low molecular mass gingipain R (RgpB) (Potempa, J., et al. (1995) *Prospect. Drug Discovery and Design* 2, 445–458) from *P. gingivalis* was then added to make an enzyme:substrate molar ratio of 1:100. The reaction mixture was made in 1 mM cysteine and the sample incubated overnight at 37° C. Generated peptides were separated by reverse-phase HPLC using a µBondapak C-18 column (3.9×300 mm) (Waters, Millford, Mass.). Peptides were eluted with 0.1% trifluoroacetic acid and acetonitrile containing 0.08% trifluoroacetic acid, using a gradient from 0 to 80% acetonitrile over 60 minutes. Peptides were monitored at 220 nm and collected manually.

For determination of the active site serine residue and to confirm that the purified enzyme was a serine peptidase, 100 µg of purified PTP-A was first incubated with 170 µCi of [1,3-$^3$H]DFP (Amersham, Arlington Heights, Ill.) for 30 minutes at 25° C. in 20 mM HEPES, pH 7.5. The reaction was quenched by addition of cold DFP to a final concentration of 10 mM and the radiolabelled material analyzed by SDS-PAGE, followed by autoradiographic analysis. The gel was dehydrated, soaked in PPO solution for 2 hours, dried, and the DFP-binding proteins detected by fluorography after an exposure time of 96 hours on X-ray film (XAR; Kodak, Rochester, N.Y.). The bulk of radiolabelled protein was subjected to proteolytic fragmentation with RgpB and peptides obtained separated by reverse-phase HPLC as described above. Radioactivity in each peptide fraction was measured using a β liquid scintillation counter, and the labeled peptide, as well as other selected peptides were subjected to sequence analysis.

Identification of the PTP-A Gene—The database containing the unfinished *P. gingivalis* W83 genome, available from The Institute for Genomic Research, was searched for the presence of nucleotide sequences corresponding to the NH$_2$-terminal and the internal PTP-A amino acid sequences using the TBLASTN algorithm, BLAST version 2.0.8, and the default values for all parameters (Altschul, S. F., et al., (1997) *Nucleic Acid Res.* 25, 3389–3402). An identified clone gnl ½ TIGR ½ *P. gingivalis*_126 was retrieved from The Institute for Genomic Research data base (on the World Wide Web at tigr.org). The position of the PTP-A gene was localized using the NCBI open reading frame (ORF) finder (available from the National Center for Biotechnology Information, on the World Wide Web at ncbi.nlm.nih.gov/gorf/gorf.html). The amino acid sequence, obtained by conceptual translation of the entire ORF, was further used for homology screening by use of the NCBI BLAST search tool.

Enzyme Specificity—Peptides were incubated with 1 µg PTP-A at an enzyme:substrate molar ratio of 1:100 for 3 hours or 24 hours in 50 µl of 200 mM HEPES, pH 7.5, at 37° C., and the reaction stopped by acidification with trifluoroacetic acid. The samples were then subjected to reverse-phase high pressure liquid chromatography using a µBondapak C-18 column (3.9×300 mm) (Waters, Millford, Mass.) and an acetonitrile gradient (0–80% in 0.075% trifluoroacetic acid in 50 min). Each peak, detected at 220 nm, was collected, lyophilized, redissolved in 50% (volume/volume) methanol, 0.1% acetic acid and subjected to analysis by mass spectrometry.

Mass Spectrometry—A Finnigan MAT 95S, sector mass spectrometer (Finnigan MAT, Bremen, Germany) equipped with an electrospray source (ESI) was used operated essentially as described previously (Stenfors, C., et al., (1997) *J. Biol. Chem.* 272, 5747–5751). Peptides were identified by fitting of the obtained spectra to specific sequences using an Internet application program MsFit available at http://falcon.ludwig.ucl.ac.uk/msfit.html.

Example 2

Enzyme Localization, Purification and Initial Characterization

Figure 1B:
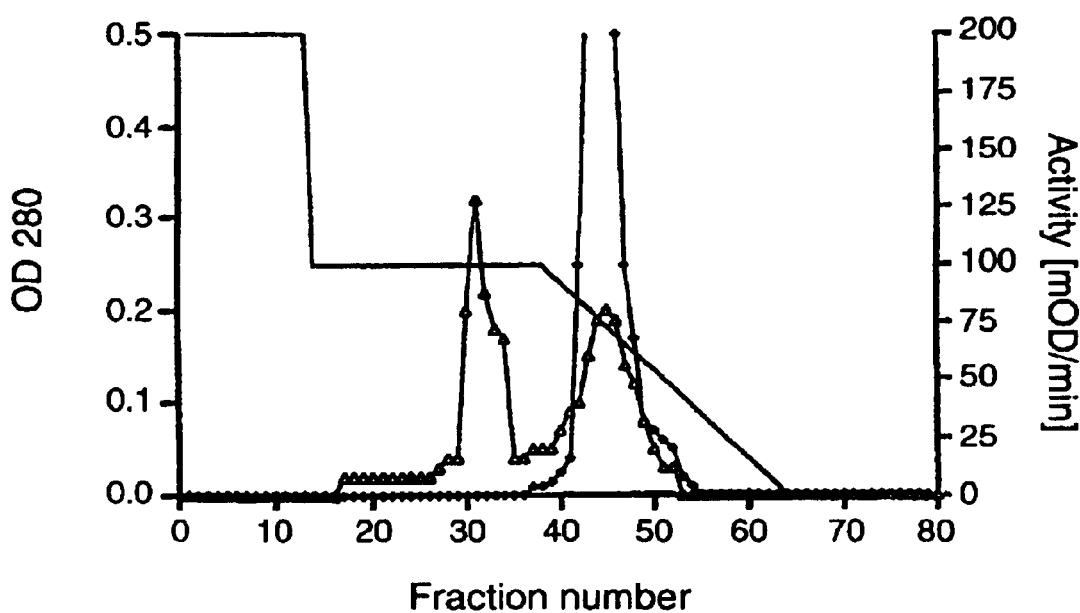
Figure 1C:
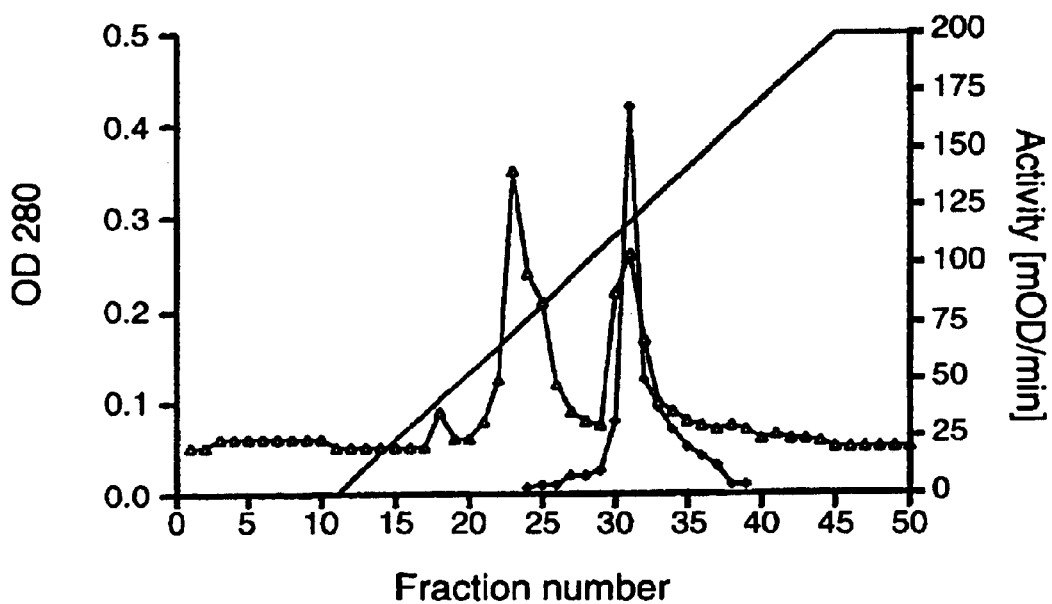
Figure 1D:
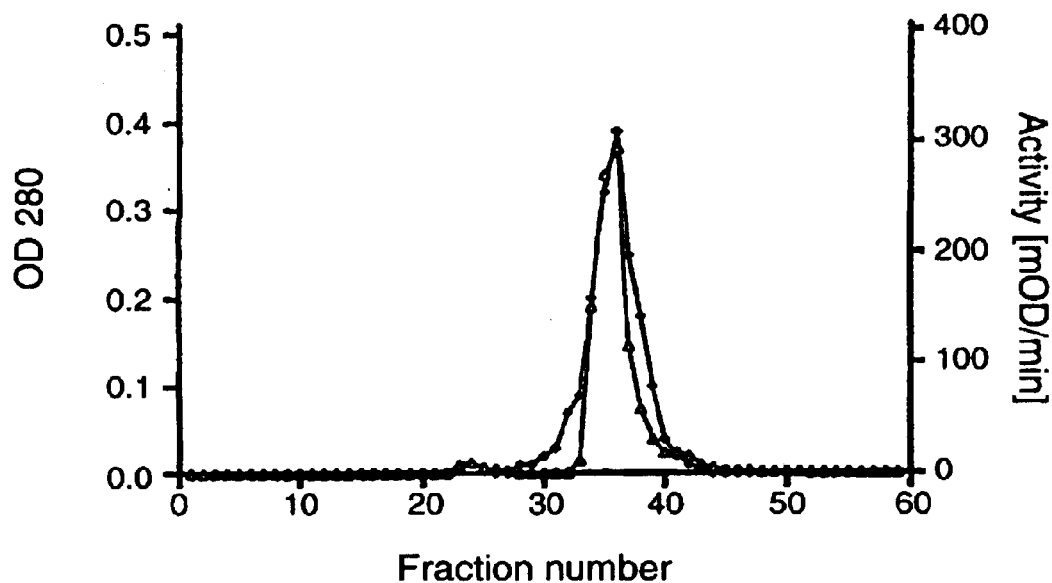

Analysis of amidolytic activity against H-Ala-Phe-Pro-pNA in several fractions of *P. gingivalis* HG66, W50 and ATCC 33277 clearly indicated that an enzyme(s) with prolyl tripeptidyl-peptidase activity is localized on the cell surface in all strains tested with less than 5% of the total activity being found in the medium regardless of the growth phase of the bacterial culture. Cell associated enzyme was easily detached from the bacterial surface by treatment with a low concentration (0.05%) of Triton X-100. This procedure released more than 85–90% of activity in a soluble form. Subsequent acetone precipitation of proteins in the Triton X-100 fraction successfully separated the activity from pigment which remained in solution. The redissolved protein fraction, after dialysis, was applied to hydroxyapatite (100 ml) equilibrated with 20 mM potassium phosphate buffer pH 7.0. The elution was carried out with 20 mM potassium phosphate buffer pH 7.0, using a phosphate gradient from 20 mM to 300 mM at flow rate 20 ml/h. At this step substantial separation of the PTP-A activity from both the DPP IV and bulk protein was achieved (FIG. 1*a*). Further purification performed by subsequent chromatography steps including Phenyl-Sepharose (FIG. 1*b*), MonoQ (FIG. 1*c*) and MonoP columns (FIG. 1*d*), resulted in the isolation of purified enzyme.

Phenyl-Sepharose HP (25 ml) was equilibrated with 50 mM potassium phosphate, 1M ammonium sulfate, pH 7.0, at flow rate 30 ml/h. The column was washed with two volumes of equilibration buffer and a step gradient of 0.5 M ammonium sulfate was applied, following which a descending gradient of 0.5 to 0 M ammonium sulfate was applied. The PTP-A containing fractions were extensively dialyzed against 20 mM Tris-HCl, pH 7.0, and concentrated by ultrafiltration. The concentrated PTP-A containing fractions were applied to a MonoQ column equilibrated with the same buffer. The column was washed with 5 volumes of equilibration buffer, following which bound protein was eluted with a gradient of 0–300 mM NaCl. The concentrated fraction of PTP-A from the MonoQ column was equilibrated with 25 mM Bis-Tris, pH 6.3, and loaded on a MonoP column equilibrated with the same buffer. A pH gradient was developed using 50 ml of Polybuffer 74, with the pH adjusted to 4.0.

Significantly, the chromatography step on the MonoP column yielded the A$_{280}$ profile much sharper than the activity peak. Although this imperfect overlap of protein and activity may suggest that the protein component does not represent the active enzyme, the rest of data argues with such a contention. This apparent contradiction may be likely explained by the enzyme inhibition by the reaction product of H-Ala-Phe-Pro-pNA hydrolysis but this possibility has not been explored. The yield of protein and activity recovery in a typical purification procedure is summarized in Table 1.

TABLE 1

Purification of the PTP-A from *P. gingivalis*

| Step | Volume (ml) | Protein (mg) | Total activity* | Specific activity (units/mg) | Purification fold | Yield (%) |
|---|---|---|---|---|---|---|
| Triton X-100 extract after centrifugation | 200 | 1200 | 757 673 | 642 | 1 | 100 |
| Acetone precipitate | 50 | 600 | 537 622 | 896 | 1.4 | 71 |
| Hydroxyapatite chromatography | 50 | 22 | 400 039 | 18183 | 28 | 53 |

TABLE 1-continued

Purification of the PTP-A from *P. gingivalis*

| Step | Volume (ml) | Protein (mg) | Total activity* | Specific activity (units/mg) | Purification fold | Yield (%) |
|---|---|---|---|---|---|---|
| Phenyl-Sepharose | 48 | 10 | 312 505 | 31250 | 48 | 41 |
| MonoQ | 3 | 1.5 | 244 828 | 163218 | 254 | 32 |
| MonoP | 4 | 0.7 | 188 400 | 269142 | 420 | 25 |

Figure 2:
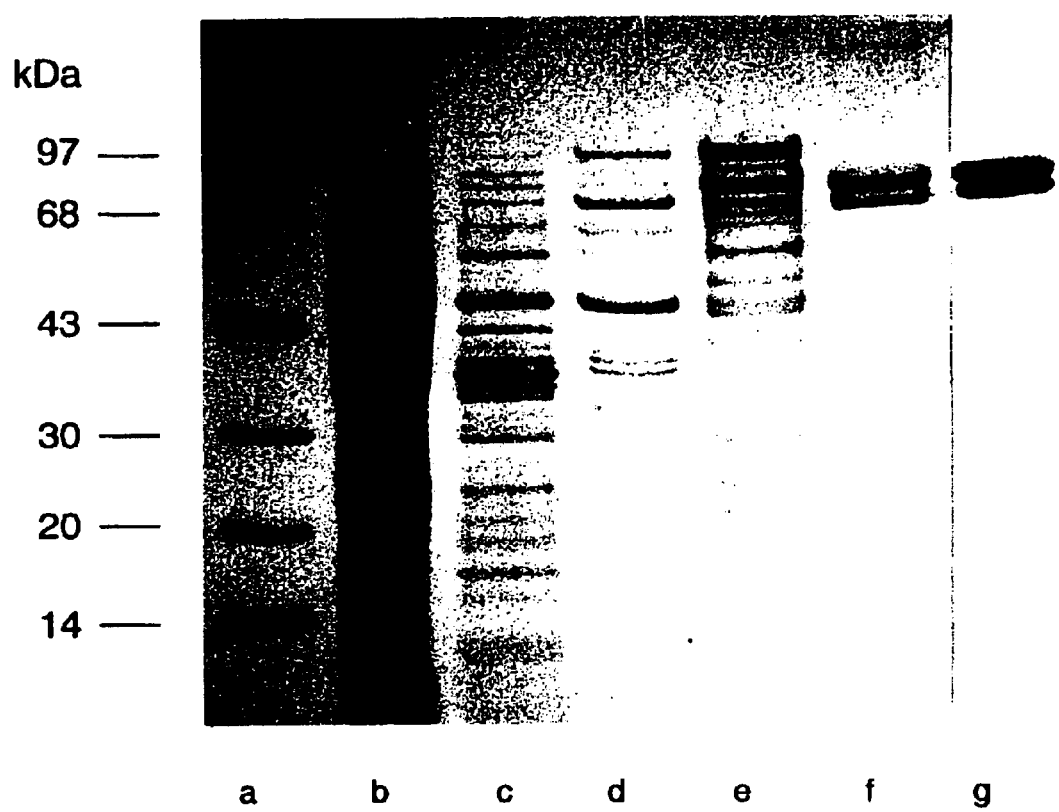
FIG. 2. SDS-PAGE of fractions from purification of PTP-A and the autoradiography of the purified enzyme. Lane a, molecular mass markers (phosphorylase B, 97 kDa; bovine serum albumin, 68 kDa; ovalbumin, 43 kDa; carbonic anhydrase, 30 kDa; soybean trypsin inhibitor, 20 kDa; α-lactalbumin, 14 kDa); lane b, acetone precipitate from Triton X-100 extract of *P. gingivalis*, lane c: hydroxyapatite column eluate; lane d, Phenyl-Sepharose column eluate; lane e, MonoQ column eluate; lane f, purified PTP-A from MonoP column wash; lane g, autoradiograph of $^3$H-DFP labeled enzyme exposed for 96 h to X-ray film. All samples were reduced and boiled prior to PAGE analysis.

*Based on the enzymatic activity using H-Ala-Phe-Pro-pNA where one unit = mOD/min/1 ml SDS-PAGE analysis of the purified enzyme revealed the presence of two protein bands with apparent molecular masses of 81.8 and 75.8 kDa, respectively (FIG. 2, lane f). Autoradiography of the enzyme sample radiolabeled with [1,3-$^3$H]DFP (FIG. 2, lane g) clearly indicated that the bands represented either two distinct serine peptidases or different molecular mass forms of the same enzyme. In an attempt to distinguish between these two options, the electrophoretically resolved proteins were subjected to amino terminal sequence analysis. Unfortunately, it was found that the 81.8 kDa form of PTP-A had a blocked N-terminus. In contrast, the sequence NH$_2$-SAQTTRFSAADLNALMP (SEQ ID NO:23) was found at the N-terminus of the lower molecular mass form of the enzyme. This result led us to the possibility that the 75.8 kDa form of PTP-A was derived from the 81.8 kDa form through proteolytic cleavage of a 6 kDa amino-terminal peptide. To confirm this hypothesis and, in addition, to localize the active site residue within *P. gingivalis* PTP-A, the mixture containing both radiolabeled enzymes was proteolytically fragmented and peptides resolved by reverse-phase HPLC. This procedure yielded only one major radioactive peptide peak, and the purified peptide was found to have a single amino acid sequence: IGVHGWXYGG-FMTINL (SEQ ID NO:24), where X apparently represents the active-site serine residue covalently and irreversibly modified by DFP. These data convincingly indicate that the two protein bands of purified PTP-A represents different forms of the same enzyme. The portion of the purified PTP-A having a truncated N-terminus may be due to cleavage by Lys-specific peptidase and is likely to be an artifact which occurred during the purification procedure. Nevertheless, the proteolytic shedding of membrane bound PTP-A also occurs during cultivation of the bacteria, as indicated by variable amount of soluble activities found in cell free culture media.

Example 3 pH Optimum, Stability and Inhibition Profile

Using the amidolytic activity assay with H-Ala-Phe-Pro-pNA it was found that the enzyme has a broad pH optimum from pH 6.0 to 8.0 and in 0.2 M HEPES, pH 7.6 was stable for at least 12 hours at 25° C. or 37° C. PTP-A activity was not affected by class specific synthetic inhibitors of cysteine or metalloproteinases (Table 2). In contrast, preincubation of the enzyme with DFP or PEFABLOCK resulted in total loss of activity, supporting its classification as a serine peptidase. Surprisingly, however, 3,4-dichloroisocumarin was only a poor inhibitor, and PMSF, leupeptin, antipain and prolinal had no effect at all. Interestingly, preincubation of PTP-A with iodoacetamide, but not with N-ethylmaleimide, stimulated enzyme amidolytic activity about two-fold. Human plasma inhibitors, such as $\alpha_1$-proteinase inhibitor, $\alpha_1$-antichymotrypsin and $\alpha_2$-macroglobulin did not affect the enzyme activity, nor were they cleaved by PTP-A.

The effect of inhibitors on amidolytic activity of DPP IV was also determined using the same conditions as those used for PTP-A, but using H-Gly-Pro-pNA as a substrate.

TABLE 2

Effect of inhibitors on the amidolytic activity of PTP-A and DPP IV. Results are for a 15-min incubation at 37 C. in 0.2 HEPES pH 7.6, with 1 mM H-Ala-Phe-Pro-pNA as substrate.

| Inhibitor | Concentration | Residual activity of PTP-A, % | Residual activity of DPP IV, % |
|---|---|---|---|
| Diisopropyl fluorophospate | 10 mM | 0 | 0 |
| Phenylmethanesulfonyl fluoride | 10 mM | 96 | 20 |
|  | 1 mg/ml | 20 | 15 |
|  | 10 mg/ml | 0 | 0 |
| PEFABLOC SC | 1 mM | 56 | 100 |
| 3,4-dichloroisocoumarin | 5 mM | 200 | 100 |
| Iodoacetamide | 5 mM | 100 | 100 |
| N-Ethylmaleimide | 1 mM | 98 | 100 |
| 1,10-orthophenanthroline | 5 mM | 93 | 100 |
|  | 0.1 mM | 100 | 100 |
| EDTA | 0.1 mM | 100 | 100 |
| Leupeptin | 0.1 mM | 100 | 20 |
| Antipain | 10 mM | 100 | 0 |
| Prolinal | 10 mM | 100 | 30 |
| Val-Pro | 10 mM | 100 | 1 |
| Ala-Pro |  |  |  |
| Ala-Gly-Pro |  |  |  |

Example 4

Substrate Specificity

Among several chromogenic substrates tested, including H-Ala-Phe-Pro-pNA, H-Gly-Pro-pNA, Z-Gly-Pro-pNA, Z-Ala-Pro-pNA, H-Pro-pNA, only H-Ala-Phe-Pro-pNA was hydrolyzed by PTP-A indicating a prolyl specific tripeptidyl-peptidase activity. To further confirm this specificity several synthetic peptides composed of 5 to 34 amino acid residues and containing at least one proline residue were tested as substrates for PTP-A. Out of 22 peptides tested only those with a proline residue in the third position from the amino terminal end were cleaved (Table 3), with the significant exception of peptides with adjacent proline residues (peptides 3, 4 and 16). In addition, a free α-amino group was absolutely required for cleavage after the third proline residue as exemplified by resistance to enzymatic hydrolysis of peptide 9, which differs from the peptide 8 only in acylation of the α-amino group of the N-terminal valine residue. Except for these two limitations, the peptide bond -Pro-↓-Yaa- was cleaved at the same rate in all peptides with the general formula NH$_2$-Xaa-Xaa-Pro-Yaa-(Xaa)$_n$ (SEQ ID NO:25), where Xaa represents any amino acid residue while Yaa could be any residue except proline, regardless of the chemical nature of the amino acids and the length of the peptide. In all cases the reaction was completed within 3 hours and prolonged incubation for 24 hours did not affect the pattern of cleavage, confirming the absolute requirement for a proline residue at the third position from the unblocked N-terminus. In addition, these data indicate that the preparation of PTP-A was free of any contamination with either aminopeptidase, dipeptidyl peptidase, or endopeptidase activities.

The cleavage specificity of DPP IV was also determined using the same conditions as those used for PTP-A. The results (Table 3) demonstrate that DPP IV does not cleave between two proline residues.

TABLE 3

Cleavage specificity of PTP-A and DPP IV on synthetic peptides.

| Substrate | Cleavage site | SEQ ID NO: |
|---|---|---|
| Peptide 1 | H-Arg-Pro-Pro-↓-Gly-Phe-Ser-Pro-Phe-Arg | 1 |
| Peptide 2 | H-Arg-Pro-Pro-↓-Gly-Phe | 2 |
| Peptide 3 | H-Lys-Arg-Pro-Pro-Gly-Phe-Ser-Pro-Phe-Arg | 3 |
| Peptide 4 | H-Tyr-Arg-Pro-Pro-Gly-Phe-Ser-Pro-Phe-Arg | 4 |
| Peptide 5 | H-Arg-Pro-Hyp-Gly-Phe-Ser-Pro-Phe-Arg | 5 |
| Peptide 6 | H-Arg-Pro-↑-Lys-Pro-↑-Gln-Gln-Phe-Phe-Gly-Leu-Met-NH$_2$ | 6 |
| Peptide 7 | H-Val-Pro-Pro-↓-Gly-Glu-Asp-Ser-Lys-Glu-Val-Ala-Ala-Pro-His-Arg-Gln | 7 |
| Peptide 8 | H-Val-Pro-Pro-↓-Gly-Glu-Asp-Ser-Lys | 8 |
| Peptide 9 | Ac-Val-Pro-Pro-Gly-Glu-Asp-Ser-Lys | 9 |
| Peptide 10 | H-Val-Glu-Pro-↓-Ile-Pro-Tyr | 10 |
| Peptide 11 | H-Arg-Gly-Pro-↓-Phe-Pro-Ile | 11 |
| Peptide 12 | H-Ala-Arg-Pro-↓-Ala-D-Lys-amide | |
| Peptide 13 | H-Pro-Asn-Pro-↓-Asn-Gln-Gly-Asn-Phe-Ile | 13 |
| Peptide 14 | H-Arg-His-Pro-↓-Lys-Tyr-Lys-Thr-Glu-Leu | 14 |
| Peptide 15 | H-Gly-Val-Pro-↓-Lys-Thr-His-Leu-Glu-Leu | 15 |
| Peptide 16 | H-Lys-Gly-Pro-Pro-Ala-Ala-Leu-Thr-Leu | 16 |
| Peptide 17 | H-Gln-Lys-Gln-Met-Ser-Asp-Arg-Arg-Glu-Asn-Asp-Met-Ser-Pro-Ser-Asn-Asn-Val-Val-Pro-Ile-His-Val-Pro-Pro-Thr-Thr-Glu-Asn-Lys-Pro-Lys-Val-Gln | 17 |
| Peptide 18 | H-Phe-Leu-Arg-Glu-Pro-Val-Ile-Phe-Leu | 18 |
| Peptide 19 | H-Gly-Ile-Arg-Pro-Tyr-Glu-Ile-Leu-Ala | 19 |
| Peptide 20 | H-Leu-Pro-↑-Asp-Leu-Asp-Ser-Ser-Leu-Ala-Ser-Ile-Gln-Glu-Leu-Leu-Ser-Pro-Gln-Glu-Pro-Pro-Arg-Pro-Pro-Glu-Ala | 20 |
| Peptide 21 | H-Cys-Leu-Ser-Ser-Gly-Thr-Leu-Pro-Gly-Pro-Gly-Asn-Asp-Ala-Ser-Arg-Glu-Leu-Glu-Ser | 21 |
| Peptide 22 | H-Lys-Ile-Ala-Gly-Tyr-His-Leu-Glu-Leu | 22 |
| Peptide 23 | H-Ser-Pro-↑-Tyr-Ser-Ser-Asp-Thr-Thr | 46 |
| Peptide 24 | H-Ala-Pro-↑-Val-Arg-Ser-Leu-Asn-Cys-Thr-Leu-Arg-Asp-Ser-Gln-Gln-Lys | 47 |

↓ indicates cleavage site mediated by PTP-A
↑ indicates cleavage site mediated by DPP IV The lack of cleavage after internal proline residues in the synthetic peptides corresponds well with the absence of any proteolytic activity on several protein substrates including IgA, IgG, albumin, azocasein, carboxymethylated rybonuclease and gelatin. However, the size of substrate, which is a limiting factor in the activity of oligopeptidases (Walter, R., et al., (1980) *Mol. Cell. Biochem.* 30, 111–127), is not restricting in the case of PTP-A, because the enzyme is able to cleave a tripeptide (NH$_2$-Xaa-Xaa-Pro) from the N-terminus of both human cystatin C and interleukin 6.

Example 5

PTP-A Sequence Analysis

Partial PTP-A amino acid sequence data allowed us to identify the *P. gingivalis* genomic clone gnl |TIGR| *P. gingivalis*_126 in the Unfinished Microbial Genomes data base, TIGR. An ORF corresponding to the PTP-A amino acid sequence was found as indicated by the fact that all sequences of the PTP-A derived peptides obtained by the enzyme polypeptide fragmentation with RgpB were present in the protein primary structure inferred from the nucleotide sequence of the ORF. The 732 amino acid polypeptide with a calculated mass of 82, 266 Da was encoded in this ORF. The homology search performed using the NCBI TBLASTN tool against GenBank+EMBL+DDBJ+PDB databases and subsequent multiple sequence alignments using the ClustalW Multiple Sequence Alignment tool (FIG. 3) indicated that PTP-A is a new member of the prolyl oligopeptidase (S9) family of serine peptidases (Rawlings, N. D., et al., (1991) *Biochem. J.* 279, 907–908).

Figures 3, 3A:
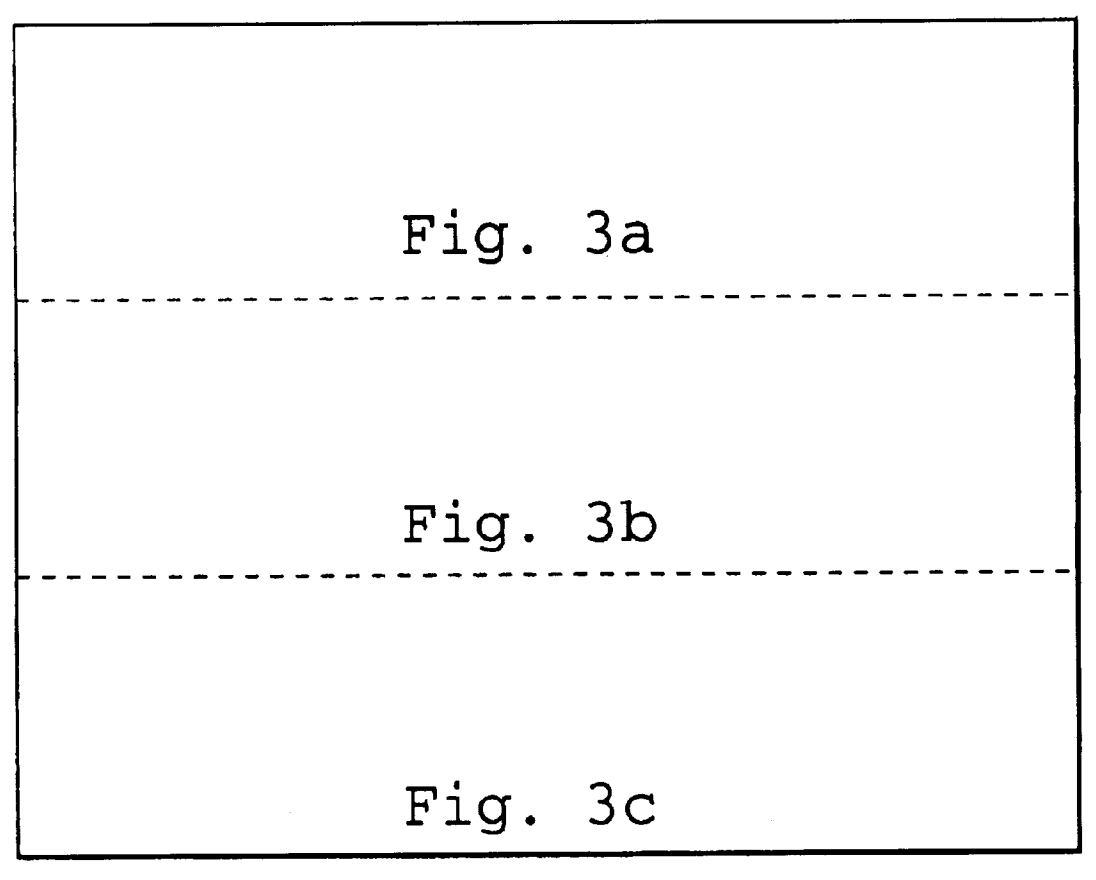
Figure 3B:
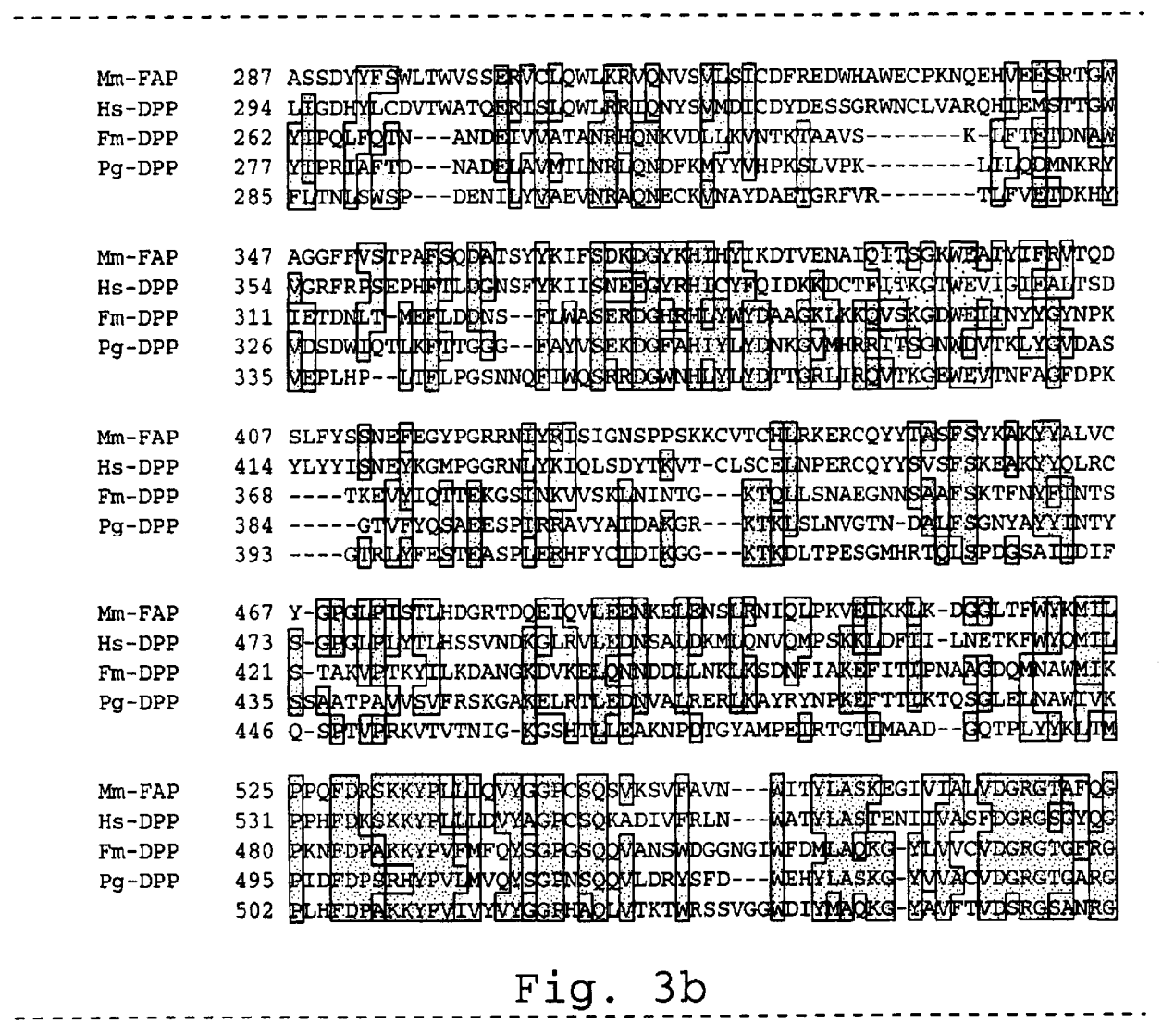

The sequence GXSXGG (SEQ ID NO:40) is a signature feature for the S9 family of serine peptidases. Within this large and diverse S9 family of evolutionary and functionally related enzymes both from prokaryotes and eukaryotes, PTP-A was most closely related to bacterial dipeptidyl peptidase IV (DPP IV) from *Flavobacterium meningosepticum*, *Xantomonas maltophilus*, and *P. gingivalis*, sharing 31.6%, 30.4%, and 28.5% amino acid sequence identity, respectively. Remarkably, the COOH-terminal region of the PTP-A molecule (residues 502–732) shows a significant similarity to the eukaryotic prolyl oligopeptidases with 34% and 33% identity to human DPP IV and mouse fibroblast activation protein (FAP), respectively (FIG. 3). This part of the molecule contains the amino acid residues which encompass the catalytic triad in all characterized prolyl oligopeptidases, and from the multiple alignments with DPP IV of confirmed active site residues (Kabashima, T., et al., (1995) *Arch. Biochem. Biophys.* 320, 123–128) it is apparent that Ser-603, Asp-678 and His-710 represent the catalytic triad of PTP-A (FIG. 3). Such an inference is further supported by the direct labeling of Ser-603 by DFP. In addition, the computer assisted search for sequential motifs characteristic for transmembrane domains revealed the presence of such a putative region within the N-terminal sequences of PTP-A, with residues 5 to 25 most likely folded into a hydrophobic α-helix responsible for membrane anchoring of this enzyme.

In *P. gingivalis* PTP-A, as well as in DPP IV, all activities are cell surface associated, and it is conceivable that the enzymes are membrane anchored through putative signal sequences which are not cleaved but remain as a membrane spanning domain similar to other members of the prolyl oligopeptidase family. The cell surface localization of di- and tripeptidyl-peptidases suggests a putative physiological function in providing nutrients for growing bacterial cells. Here, the inability of asaccharolytic *P. gingivalis* to utilize free amino acids (Dashper, S. G., et al., *J. Dent Res.* 77, 1133 (Abstract) (1996)) makes the bacterium entirely dependant on an external peptide supply. In this regard, DPP-IV and PTP-A activities are probably very important, if not indispensable, for bacterial growth.

Figure 6A:
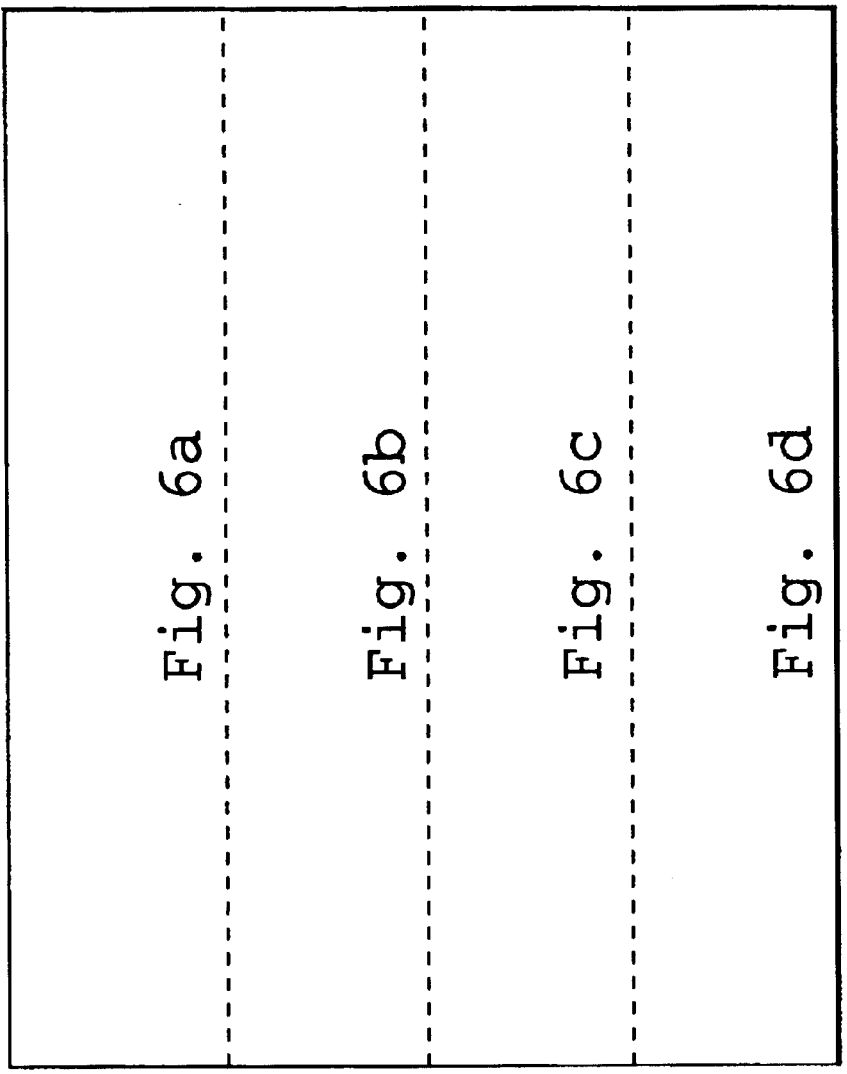
FIG. 6. Comparison of *P. gingivalis* PTP-A and DPP to sequences of three putative homologues identified within the *P. gingivalis* genome (DPP-H1, DPP-H2 and DPP-H3). Sequences of *P. gingivalis* PTP-A (126PP), DPP (87PP), DPP-H1 (65PP), DPP-H2 (101PP), and DPP-H3 (9PP) were obtained as described in FIG. 4. Homologous regions (i.e., regions of identical amino acids and/or conservative substitutions) are highlighted. Identical regions are shown as white letters on a black background. Similar regions (i.e., conservative substitutions) are shown as white letters on a grey background.
Figure 6B:
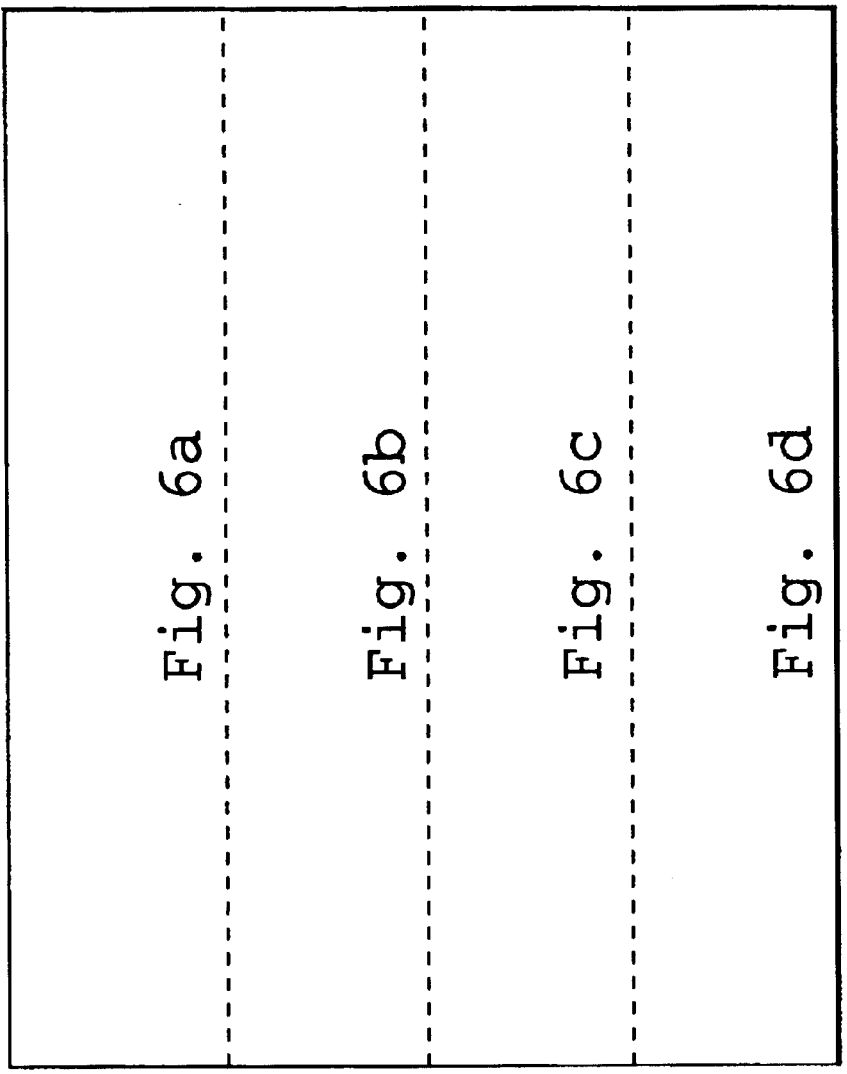
Figure 6C:
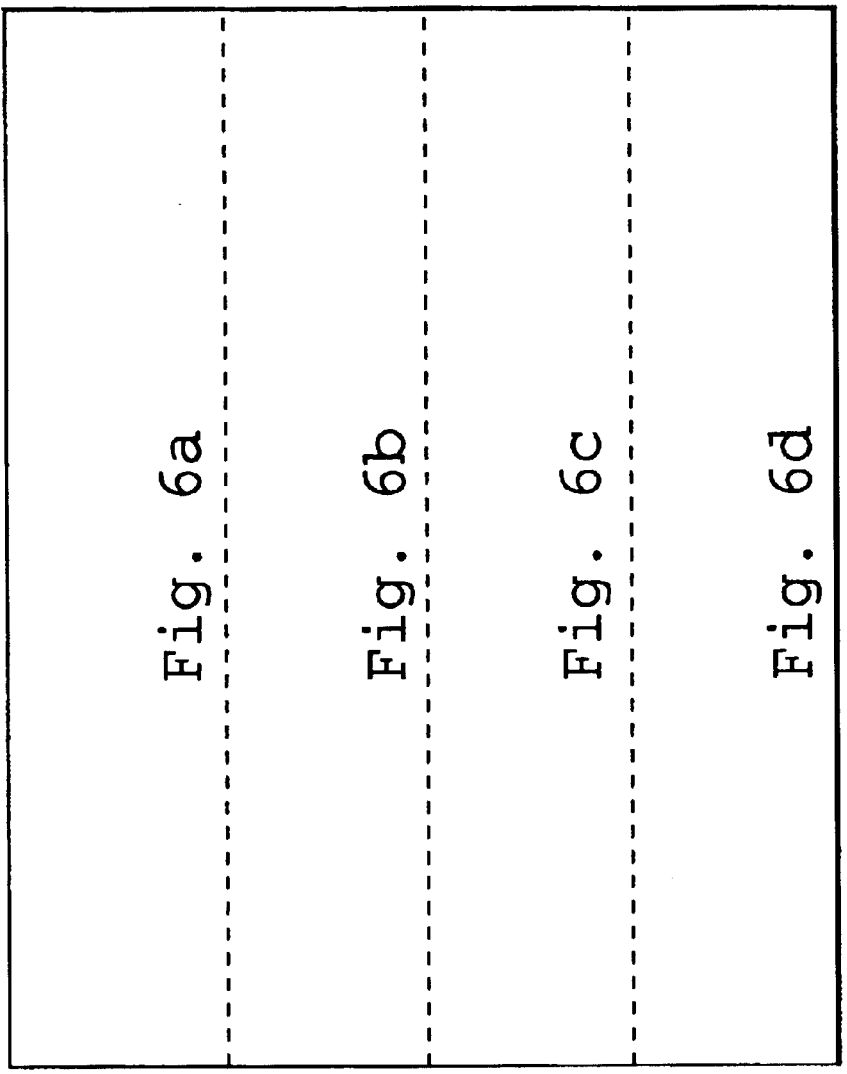
Figure 6D:
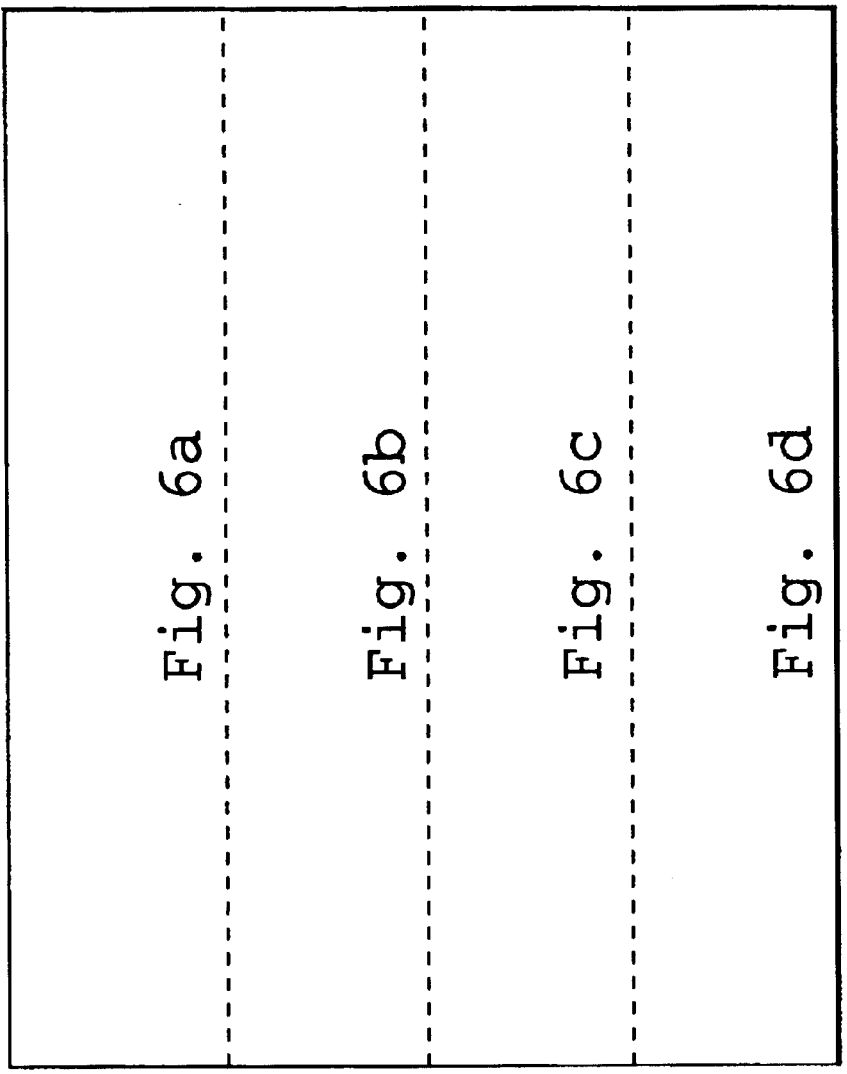
Figure 6:
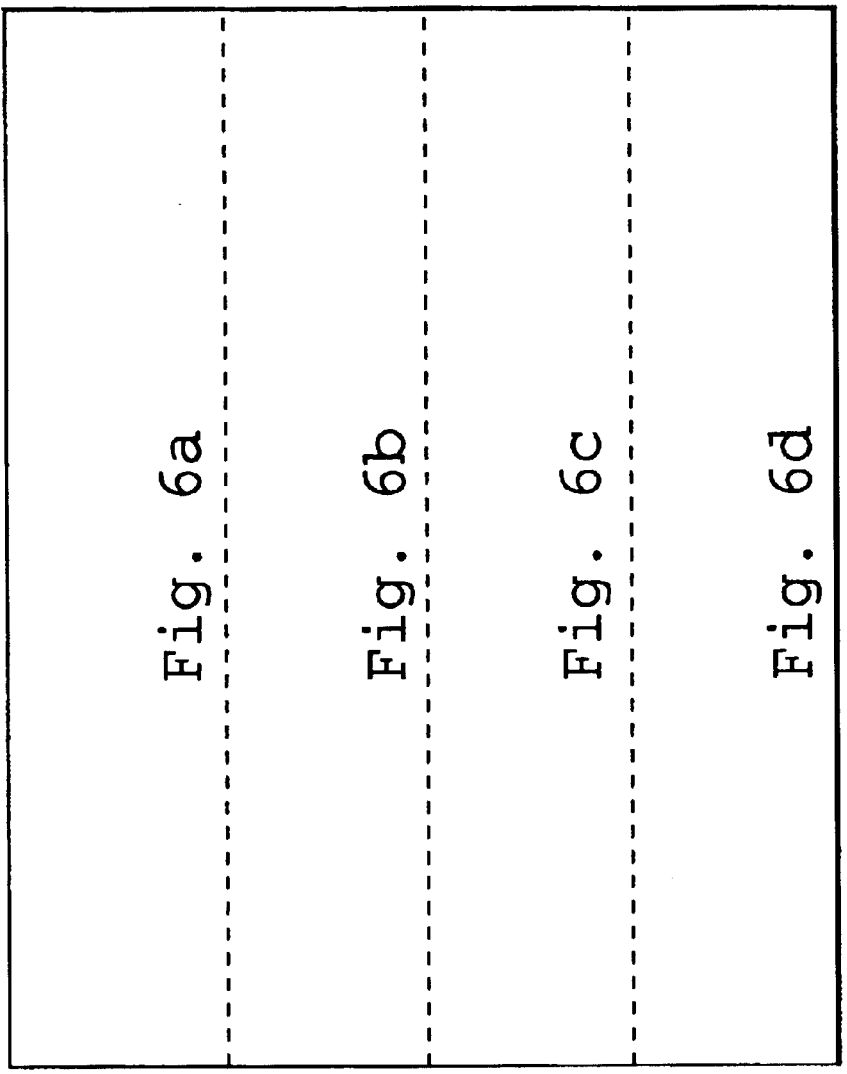
Figure 7:
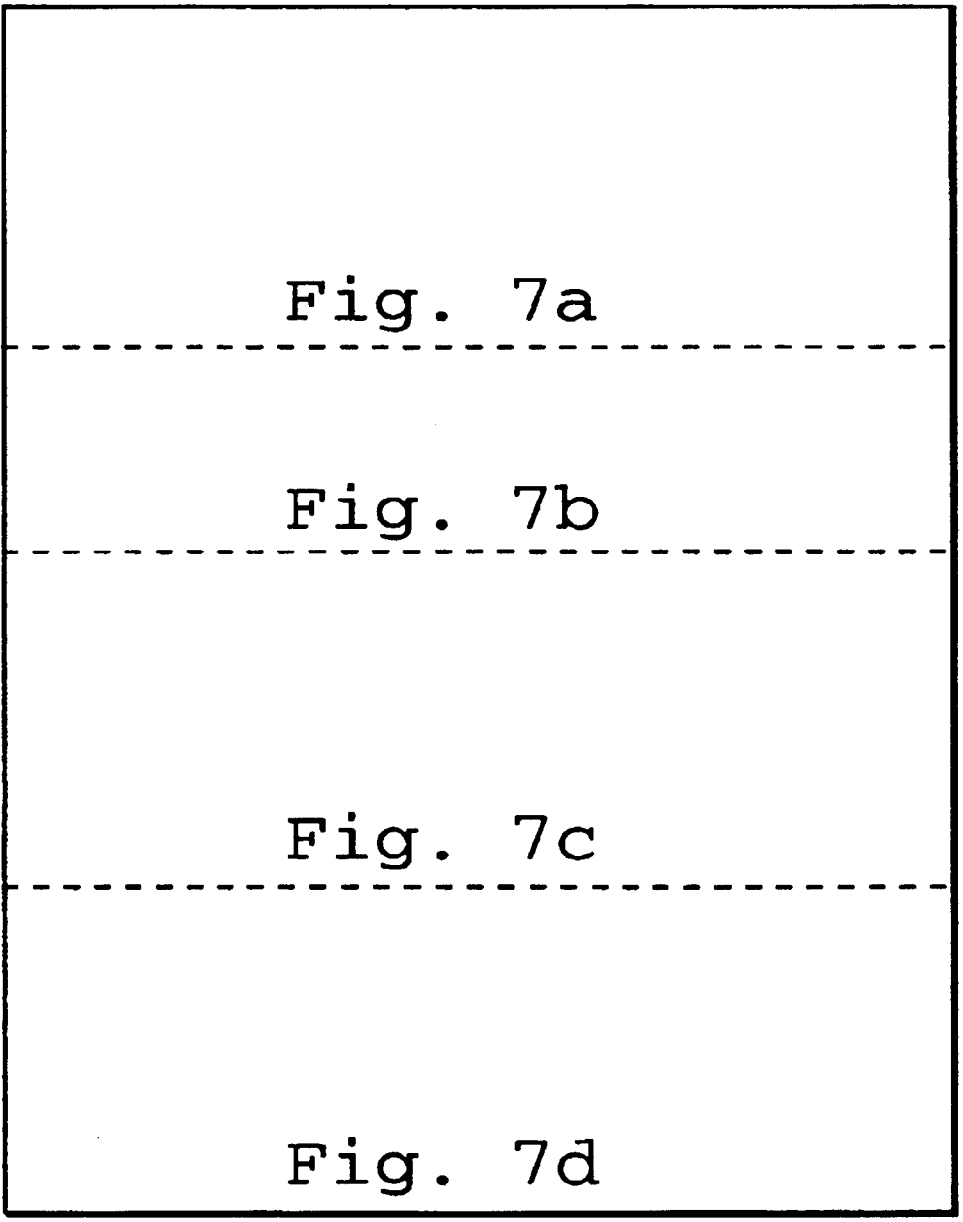
FIG. 7. Nucleotide sequence (SEQ ID NO:38) and amino acid sequence (SEQ ID NO:30) of PTP-A.

This suggestion is strongly corroborated by the fact that the *P. gingivalis* genome contains three additional genes encoding peptidases homologous with DPP-IV and PTP-A and one related to aminopeptidase B. The peptidases homologous with DPP-IV and PTP-A are referred to as homologs H1 (SEQ ID NO:43), H2 (SEQ ID NO:44), and H3 (SEQ ID NO:45) (FIG. 6). If expressed, each gene product would probably have enzymatic activity because each has a well preserved catalytic triad (FIG. 4). In addition, all of these genes encode a putative signal peptide which may act in providing membrane-anchorage motifs.

Example 6

Influence of Proteinase Inhibitor on *P. gingivalis* Growth

Figure 5:
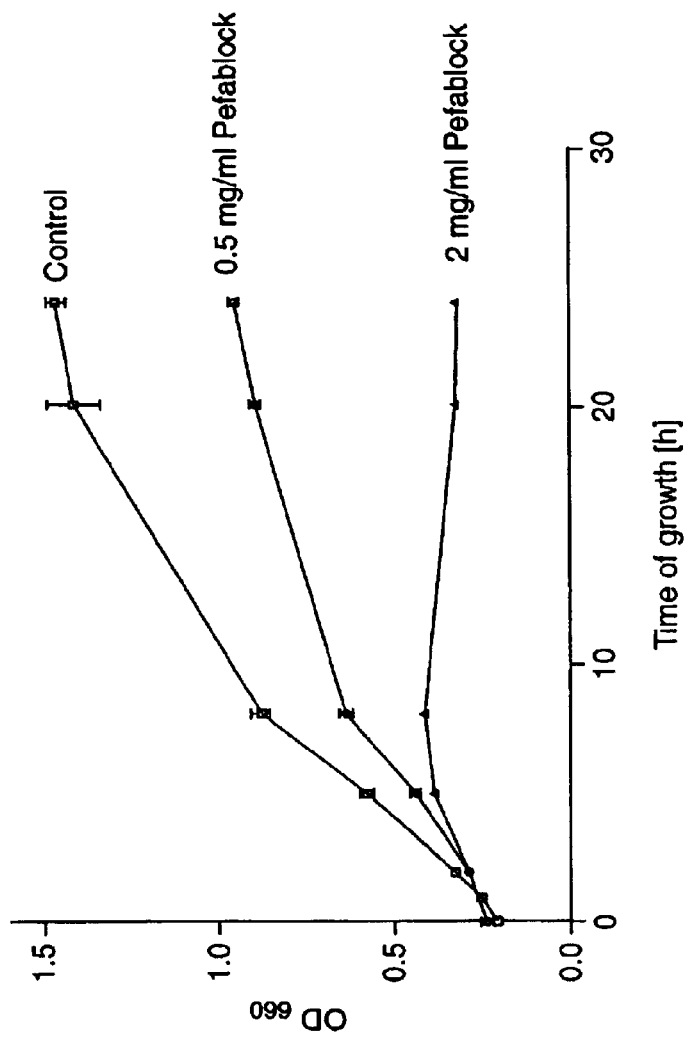
FIG. 5. Influence of Pefabloc-serine proteinase inhibitor on *P. gingivalis* growth.

To evaluate whether *P. gingivalis* growth was influenced by the presence of a peptidase inhibitor, *P. gingivalis* in logphase growth was diluted 1:5 into liquid media and incubated at 37° C. The cell density was monitored by measuring the optical density at 600 nm (OD$_{600}$). When the optical density began to increase, Pefabloc was added at 0.5 mg/ml or at 2.0 mg/ml. The control culture received no Pefabloc. The cultures receiving Pefabloc exhibited decreased growth (FIG. 5). The peptidase inhibitor had to be added before the culture reached an OD$_{600}$ of about 0.3 for the peptidase inhibitor to have an effect on growth.

The complete disclosures of all patents, patent applications, publications, and nucleic acid and protein database entries, including for example GenBank accession numbers and EMBL accession numbers, that are cited herein are hereby incorporated by reference as if individually incorporated. Various modifications and alterations of this invention will become apparent to those skilled in the art without departing from the scope and spirit of this invention, and it should be understood that this invention is not to be unduly limited to the illustrative embodiments set forth herein.

| Sequence Listing Free Text | |
| --- | --- |
| SEQ ID NOs:1–11: | Synthetic peptides |
| SEQ ID NO:12: | Target peptide |
| SEQ ID NOs:13–22: | Synthetic peptides |
| SEQ ID NO:23: | Amino-terminus of the lower molecular mass form of PTP-A. |
| SEQ ID NO:24: | Amino acid sequence present in PTP-A, where X apparently represents the active-site serine residue covalently and irreversibly modified by DFP. |
| SEQ ID NO:25: | Target peptide, where Xaa represents a natural or modified amino acid residue, Yaa represents a natural or modified amino acid residue except proline, and N is equal to or greater than 1. |
| SEQ ID NO:26: | Mouse fibroblast activation protein |
| SEQ ID NO:27: | Human DPP IV |
| SEQ ID NO:28: | DPP from *Flavobacterium meningosepticum* |
| SEQ ID NO:29: | DPP from *P. gingivalis* |
| SEQ ID NO:30: | *P. gingivalis* PTP-A |
| SEQ ID NO:31: | Portion of PTP-A |
| SEQ ID NO:32: | Portion of DPP from *P. gingivalis* |

| -continued | |
| --- | --- |
| Sequence Listing Free Text | |
| SEQ ID NO:33: | Portion of H1 homolog of *P. gingivalis* DPP |
| SEQ ID NO:34: | Portion of H2 homolog of *P. gingivalis* DPP |
| SEQ ID NO:35: | Portion of H3 homolog of *P. gingivalis* DPP |
| SEQ ID NOs:36–37: | Probes |
| SEQ ID NO:38: | Nucleotide sequence of coding region encoding PTP-A. |
| SEQ ID NO:39: | Consensus sequence for clan SC where X is any amino acid and S is the active site serine GXSXXG. |
| SEQ ID NO:40: | Consensus sequence for family S9 where X is any amino acid and S is the active site serine GXSXGG. |
| SEQ ID NO:41: | A specific substrate for a prolyl-tripeptidyl peptidase, where Xaa represents a natural or modified amino acid residue, and Yaa represents a natural or modified amino acid residue except proline. |
| SEQ ID NO:42: | DPP from *P. gingivalis* |
| SEQ ID NO:43: | H1 homolog of *P. gingivalis* DPP |
| SEQ ID NO:44: | H2 homolog of *P. gingivalis* DPP |
| SEQ ID NO:45: | H3 homolog of *P. gingivalis* DPP |
| SEQ ID NO:46: | Synthetic peptides |
| SEQ ID NO:47: | Synthetic peptides |
| SEQ ID NO:48: | Amino terminal sequence of DPP IV |

What is claimed is:

1. An isolated nucleic acid, the complement of which hybridizes to SEQ ID NO:38 under hybridization conditions of 0.5 M phosphate buffer, pH 7.2, 7% SDS, 10 mM EDTA, at 68° C., followed by three 20 minute washes in 2×SSC, and 0.1% SDS, at 65° C., wherein the isolated nucleic acid encodes a protein having prolyl-tripeptidyl peptidase amidolytic activity comprising SEQ ID NO:30, wherein prolyl-tripeptidyl peptidase amidolytic activity is defined as activity for cleaving a peptide bond between the proline and the Yaa residues in a target polypeptide of the general formula $NH_2$-Xaa-Xaa-Pro-Yaa-(Xaa)$_n$, wherein Xaa is a natural or modified amino acid, Yaa is a natural or modified amino acid except proline, and the α-amino of the amino terminal residue is not blocked, and wherein prolyl-tripeptidyl peptidase amidolytic activity is determined under conditions including a prolyl tripeptidyl-peptidase:target polypeptide ratio of at least about 1:1 to no greater than about 1:10,000,000 in about 200 mM HEPES, about pH 7.5 at 37° C. for at least about 3 hours.

2. An isolated nucleic acid consisting of nucleotide sequence SEQ ID NO:38.

3. An isolated nucleic acid encoding a protein consisting of SEQ ID NO:30.

* * * * *

SEQUENCE LISTING

```
<160> NUMBER OF SEQ ID NOS: 48

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence:  synthetic
      peptide

<400> SEQUENCE: 1

Arg Pro Pro Gly Phe Ser Pro Phe Arg
  1               5

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence:  synthetic
      peptide

<400> SEQUENCE: 2

Arg Pro Pro Gly Phe
  1               5
```

```
<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 3

Lys Arg Pro Pro Gly Phe Ser Pro Phe Arg
 1               5                  10

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 4

Tyr Arg Pro Pro Gly Phe Ser Pro Phe Arg
 1               5                  10

<210> SEQ ID NO 5
<211> LENGTH: 8
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 5

Arg Pro Gly Phe Ser Pro Phe Arg
 1               5

<210> SEQ ID NO 6
<211> LENGTH: 11
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 6

Arg Pro Lys Pro Gln Gln Phe Phe Gly Leu Met
 1               5                  10

<210> SEQ ID NO 7
<211> LENGTH: 16
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 7

Val Pro Pro Gly Glu Asp Ser Lys Glu Val Ala Ala Pro His Arg Gln
 1               5                  10                  15

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence: synthetic
      peptide
```

```
<400> SEQUENCE: 8

Val Pro Pro Gly Glu Asp Ser Lys
 1               5

<210> SEQ ID NO 9
<211> LENGTH: 8
<212> TYPE: PRT
<213> ORGANISM: Artificial Sequence
<220> FEATURE:
<223> OTHER INFORMATION: Description of Artificial Sequence:  synthetic
      peptide

<400> SEQUENCE: 9

Val Pro Pro Gly Glu Asp Ser Lys
 1               5

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence:  synthetic
      peptide

<400> SEQUENCE: 10

Val Glu Pro Ile Pro Tyr
 1               5

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence:  synthetic
      peptide

<400> SEQUENCE: 11

Arg Gly Pro Phe Pro Ile
 1               5

<210> SEQ ID NO 12
<211> LENGTH: 4
<212> TYPE: PRT
<213> ORGANISM: Artificial Sequence
<220> FEATURE:
<223> OTHER INFORMATION: Description of Artificial Sequence:  target
      peptide
<221> NAME/KEY: VARIANT
<222> LOCATION: (1)
<223> OTHER INFORMATION: A natural or modified amino acid
<221> NAME/KEY: VARIANT
<222> LOCATION: (2)
<223> OTHER INFORMATION: proline or alanine
<221> NAME/KEY: VARIANT
<222> LOCATION: (3)
<223> OTHER INFORMATION: A natural or modified amino acid except proline
      or hydroxyproline
<221> NAME/KEY: VARIANT
<222> LOCATION: (4)
<223> OTHER INFORMATION: A natural or modified amino acid

<400> SEQUENCE: 12

Xaa Xaa Xaa Xaa
 1

<210> SEQ ID NO 13
<211> LENGTH: 9
<212> TYPE: PRT
<213> ORGANISM: Artificial Sequence
```

```
<220> FEATURE:
<223> OTHER INFORMATION: Description of Artificial Sequence: synthetic
      peptide

<400> SEQUENCE: 13

Pro Asn Pro Asn Gln Gly Asn Phe Ile
  1               5

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 14

Arg His Pro Lys Tyr Lys Thr Glu Leu
  1               5

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 15

Gly Val Pro Lys Thr His Leu Glu Leu
  1               5

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 16

Lys Gly Pro Pro Ala Ala Leu Thr Leu
  1               5

<210> SEQ ID NO 17
<211> LENGTH: 34
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 17

Gln Lys Gln Met Ser Asp Arg Arg Glu Asn Asp Met Ser Pro Ser Asn
  1               5                  10                  15

Asn Val Val Pro Ile His Val Pro Pro Thr Thr Glu Asn Lys Pro Lys
                 20                  25                  30

Val Gln

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: synthetic
      peptide
```

```
<400> SEQUENCE: 18

Phe Leu Arg Glu Pro Val Ile Phe Leu
  1               5

<210> SEQ ID NO 19
<211> LENGTH: 9
<212> TYPE: PRT
<213> ORGANISM: Artificial Sequence
<220> FEATURE:
<223> OTHER INFORMATION: Description of Artificial Sequence:  synthetic
      peptide

<400> SEQUENCE: 19

Gly Ile Arg Pro Tyr Glu Ile Leu Ala
  1               5

<210> SEQ ID NO 20
<211> LENGTH: 26
<212> TYPE: PRT
<213> ORGANISM: Artificial Sequence
<220> FEATURE:
<223> OTHER INFORMATION: Description of Artificial Sequence:  synthetic
      peptide

<400> SEQUENCE: 20

Leu Pro Asp Leu Asp Ser Ser Leu Ala Ser Ile Gln Glu Leu Leu Ser
  1               5                  10                  15

Pro Gln Glu Pro Pro Arg Pro Pro Glu Ala
             20                  25

<210> SEQ ID NO 21
<211> LENGTH: 20
<212> TYPE: PRT
<213> ORGANISM: Artificial Sequence
<220> FEATURE:
<223> OTHER INFORMATION: Description of Artificial Sequence:  synthetic
      peptide

<400> SEQUENCE: 21

Cys Leu Ser Ser Gly Thr Leu Pro Gly Pro Gly Asn Asp Ala Ser Arg
  1               5                  10                  15

Glu Leu Glu Ser
             20

<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence:  synthetic
      peptide

<400> SEQUENCE: 22

Lys Ile Ala Gly Tyr His Leu Glu Leu
  1               5

<210> SEQ ID NO 23
<211> LENGTH: 17
<212> TYPE: PRT
<213> ORGANISM: Porphyromonas gingivalis

<400> SEQUENCE: 23

Ser Ala Gln Thr Thr Arg Phe Ser Ala Ala Asp Leu Asn Ala Leu Met
  1               5                  10                  15

Pro
```

<210> SEQ ID NO 24
<211> LENGTH: 16
<212> TYPE: PRT
<213> ORGANISM: Porphyromonas gingivalis
<220> FEATURE:
<221> NAME/KEY: VARIANT
<222> LOCATION: (7)
<223> OTHER INFORMATION: Active-site serine covalently and irreversibly
      modified by DFP

<400> SEQUENCE: 24

Ile Gly Val His Gly Trp Xaa Tyr Gly Gly Phe Met Thr Thr Asn Leu
 1               5                  10                  15

<210> SEQ ID NO 25
<211> LENGTH: 5
<212> TYPE: PRT
<213> ORGANISM: Artificial Sequence
<220> FEATURE:
<223> OTHER INFORMATION: Description of Artificial Sequence: target
      peptide
<221> NAME/KEY: VARIANT
<222> LOCATION: (1)
<223> OTHER INFORMATION: A natural or modified amino acid
<221> NAME/KEY: VARIANT
<222> LOCATION: (2)
<223> OTHER INFORMATION: A natural or modified amino acid
<221> NAME/KEY: VARIANT
<222> LOCATION: (4)
<223> OTHER INFORMATION: A natural or modified amino acid except proline
<221> NAME/KEY: VARIANT
<222> LOCATION: (5)
<223> OTHER INFORMATION: A natural or modified amino acid

<400> SEQUENCE: 25

Xaa Xaa Pro Xaa Xaa
 1               5

<210> SEQ ID NO 26
<211> LENGTH: 761
<212> TYPE: PRT
<213> ORGANISM: Mus musculus

<400> SEQUENCE: 26

Met Lys Thr Trp Leu Lys Thr Val Phe Gly Val Thr Thr Leu Ala Ala
 1               5                  10                  15

Leu Ala Leu Val Val Ile Cys Ile Val Leu Arg Pro Ser Arg Val Tyr
                20                  25                  30

Lys Pro Glu Gly Asn Thr Lys Arg Ala Leu Thr Leu Lys Asp Ile Leu
            35                  40                  45

Asn Gly Thr Phe Ser Tyr Lys Thr Tyr Phe Pro Asn Trp Ile Ser Glu
        50                  55                  60

Gln Glu Tyr Leu His Gln Ser Glu Asp Asp Asn Ile Val Phe Tyr Asn
65                  70                  75                  80

Ile Glu Thr Arg Glu Ser Tyr Ile Ile Leu Ser Asn Ser Thr Met Lys
                85                  90                  95

Ser Val Asn Ala Thr Asp Tyr Gly Leu Ser Pro Asp Arg Gln Phe Val
            100                 105                 110

Tyr Leu Glu Ser Asp Tyr Ser Lys Leu Trp Arg Tyr Ser Tyr Thr Ala
        115                 120                 125

Thr Tyr Tyr Ile Tyr Asp Leu Gln Asn Gly Glu Phe Val Arg Gly Tyr
    130                 135                 140

Glu Leu Pro Arg Pro Ile Gln Tyr Leu Cys Trp Ser Pro Val Gly Ser

-continued

```
            145                 150                 155                 160
Lys Leu Ala Tyr Val Tyr Gln Asn Asn Ile Tyr Leu Lys Gln Arg Pro
                165                 170                 175
Gly Asp Pro Pro Phe Gln Ile Thr Tyr Thr Gly Arg Glu Asn Arg Ile
                180                 185                 190
Phe Asn Gly Ile Pro Asp Trp Val Tyr Glu Glu Met Leu Ala Thr
                195                 200                 205
Lys Tyr Ala Leu Trp Trp Ser Pro Asp Gly Lys Phe Leu Ala Tyr Val
                210                 215                 220
Glu Phe Asn Asp Ser Asp Ile Pro Ile Ile Ala Tyr Ser Tyr Tyr Gly
225                 230                 235                 240
Asp Gly Gln Tyr Pro Arg Thr Ile Asn Ile Pro Tyr Pro Lys Ala Gly
                245                 250                 255
Ala Lys Asn Pro Val Val Arg Val Phe Ile Val Asp Thr Thr Tyr Pro
                260                 265                 270
His His Val Gly Pro Met Glu Val Pro Val Pro Glu Met Ile Ala Ser
                275                 280                 285
Ser Asp Tyr Tyr Phe Ser Trp Leu Thr Trp Val Ser Ser Glu Arg Val
                290                 295                 300
Cys Leu Gln Trp Leu Lys Arg Val Gln Asn Val Ser Val Leu Ser Ile
305                 310                 315                 320
Cys Asp Phe Arg Glu Asp Trp His Ala Trp Glu Cys Pro Lys Asn Gln
                325                 330                 335
Glu His Val Glu Glu Ser Arg Thr Gly Trp Ala Gly Gly Phe Phe Val
                340                 345                 350
Ser Thr Pro Ala Phe Ser Gln Asp Ala Thr Ser Tyr Tyr Lys Ile Phe
                355                 360                 365
Ser Asp Lys Asp Gly Tyr Lys His Ile His Tyr Ile Lys Asp Thr Val
                370                 375                 380
Glu Asn Ala Ile Gln Ile Thr Ser Gly Lys Trp Glu Ala Ile Tyr Ile
385                 390                 395                 400
Phe Arg Val Thr Gln Asp Ser Leu Phe Tyr Ser Ser Asn Glu Phe Glu
                405                 410                 415
Gly Tyr Pro Gly Arg Arg Asn Ile Tyr Arg Ile Ser Ile Gly Asn Ser
                420                 425                 430
Pro Pro Ser Lys Lys Cys Val Thr Cys His Leu Arg Lys Glu Arg Cys
                435                 440                 445
Gln Tyr Tyr Thr Ala Ser Phe Ser Tyr Lys Ala Lys Tyr Tyr Ala Leu
                450                 455                 460
Val Cys Tyr Gly Pro Gly Leu Pro Ile Ser Thr Leu His Asp Gly Arg
465                 470                 475                 480
Thr Asp Gln Glu Ile Gln Val Leu Glu Glu Asn Lys Glu Leu Glu Asn
                485                 490                 495
Ser Leu Arg Asn Ile Gln Leu Pro Lys Val Glu Ile Lys Lys Leu Lys
                500                 505                 510
Asp Gly Gly Leu Thr Phe Trp Tyr Lys Met Ile Leu Pro Pro Gln Phe
                515                 520                 525
Asp Arg Ser Lys Lys Tyr Pro Leu Leu Ile Gln Val Tyr Gly Gly Pro
                530                 535                 540
Cys Ser Gln Ser Val Lys Ser Val Phe Ala Val Asn Trp Ile Thr Tyr
545                 550                 555                 560
Leu Ala Ser Lys Glu Gly Ile Val Ile Ala Leu Val Asp Gly Arg Gly
                565                 570                 575
```

```
Thr Ala Phe Gln Gly Asp Lys Phe Leu His Ala Val Tyr Arg Lys Leu
            580                 585                 590

Gly Val Tyr Glu Val Asp Gln Leu Thr Ala Val Arg Lys Phe Ile
        595                 600                 605

Glu Met Gly Phe Ile Asp Glu Arg Ile Ala Ile Trp Gly Trp Ser
    610                 615                 620

Tyr Gly Gly Tyr Val Ser Ser Leu Ala Leu Ala Ser Gly Thr Gly Leu
625                 630                 635                 640

Phe Lys Cys Gly Ile Ala Val Ala Pro Val Ser Ser Trp Glu Tyr Tyr
                645                 650                 655

Ala Ser Ile Tyr Ser Glu Arg Phe Met Gly Leu Pro Thr Lys Asp Asp
            660                 665                 670

Asn Leu Glu His Tyr Lys Asn Ser Thr Val Met Ala Arg Ala Glu Tyr
            675                 680                 685

Phe Arg Asn Val Asp Tyr Leu Leu Ile His Gly Thr Ala Asp Asp Asn
    690                 695                 700

Val His Phe Gln Asn Ser Ala Gln Ile Ala Lys Ala Leu Val Asn Ala
705                 710                 715                 720

Gln Val Asp Phe Gln Ala Met Trp Tyr Ser Asp Gln Asn His Gly Ile
                725                 730                 735

Ser Ser Gly Arg Ser Gln Asn His Leu Tyr Thr His Met Thr His Phe
            740                 745                 750

Leu Lys Gln Cys Phe Ser Leu Ser Asp
            755                 760

<210> SEQ ID NO 27
<211> LENGTH: 766
<212> TYPE: PRT
<213> ORGANISM: Homo sapiens

<400> SEQUENCE: 27

Met Lys Thr Pro Trp Arg Val Leu Leu Gly Leu Leu Gly Ala Ala Ala
  1               5                  10                  15

Leu Val Thr Ile Ile Thr Val Pro Val Val Leu Leu Asn Lys Gly Thr
            20                  25                  30

Asp Asp Ala Thr Ala Asp Ser Arg Lys Thr Tyr Thr Leu Thr Asp Tyr
        35                  40                  45

Leu Lys Asn Thr Tyr Arg Leu Lys Leu Tyr Ser Leu Arg Trp Ile Ser
    50                  55                  60

Asp His Glu Tyr Leu Tyr Lys Gln Glu Asn Asn Ile Leu Val Phe Asn
 65                  70                  75                  80

Ala Glu Tyr Gly Asn Ser Ser Val Phe Leu Glu Asn Ser Thr Phe Asp
                85                  90                  95

Glu Phe Gly His Ser Ile Asn Asp Tyr Ser Ile Ser Pro Asp Gly Gln
            100                 105                 110

Phe Ile Leu Leu Glu Tyr Asn Tyr Val Lys Gln Trp Arg His Ser Tyr
        115                 120                 125

Thr Ala Ser Tyr Asp Ile Tyr Asp Leu Asn Lys Arg Gln Leu Ile Thr
    130                 135                 140

Glu Glu Arg Ile Pro Asn Asn Thr Gln Trp Val Thr Trp Ser Pro Val
145                 150                 155                 160

Gly His Lys Leu Ala Tyr Val Trp Asn Asn Asp Ile Tyr Val Lys Ile
                165                 170                 175

Glu Pro Asn Leu Pro Ser Tyr Arg Ile Thr Trp Thr Gly Lys Glu Asp
```

-continued

```
            180                 185                 190
Ile Ile Tyr Asn Gly Ile Thr Asp Trp Val Tyr Glu Glu Val Phe
        195                 200                 205
Ser Ala Tyr Ser Ala Leu Trp Trp Ser Pro Asn Gly Thr Phe Leu Ala
        210                 215                 220
Tyr Ala Gln Phe Asn Asp Thr Glu Val Pro Leu Ile Glu Tyr Ser Phe
225                 230                 235                 240
Tyr Ser Asp Glu Ser Leu Gln Tyr Pro Lys Thr Val Arg Val Pro Tyr
                245                 250                 255
Pro Lys Ala Gly Ala Val Asn Pro Thr Val Lys Phe Phe Val Val Asn
                260                 265                 270
Thr Asp Ser Leu Ser Ser Val Thr Asn Ala Thr Ser Ile Gln Ile Thr
                275                 280                 285
Ala Pro Ala Ser Met Leu Ile Gly Asp His Tyr Leu Cys Asp Val Thr
                290                 295                 300
Trp Ala Thr Gln Glu Arg Ile Ser Leu Gln Trp Leu Arg Arg Ile Gln
305                 310                 315                 320
Asn Tyr Ser Val Met Asp Ile Cys Asp Tyr Asp Glu Ser Ser Gly Arg
                325                 330                 335
Trp Asn Cys Leu Val Ala Arg Gln His Ile Glu Met Ser Thr Thr Gly
                340                 345                 350
Trp Val Gly Arg Phe Arg Pro Ser Glu Pro His Phe Thr Leu Asp Gly
                355                 360                 365
Asn Ser Phe Tyr Lys Ile Ser Asn Glu Glu Gly Tyr Arg His Ile
                370                 375                 380
Cys Tyr Phe Gln Ile Asp Lys Lys Asp Cys Thr Phe Ile Thr Lys Gly
385                 390                 395                 400
Thr Trp Glu Val Ile Gly Ile Glu Ala Leu Thr Ser Asp Tyr Leu Tyr
                405                 410                 415
Tyr Ile Ser Asn Glu Tyr Lys Gly Met Pro Gly Gly Arg Asn Leu Tyr
                420                 425                 430
Lys Ile Gln Leu Ser Asp Tyr Thr Lys Val Thr Cys Leu Ser Cys Glu
                435                 440                 445
Leu Asn Pro Glu Arg Cys Gln Tyr Tyr Ser Val Ser Phe Ser Lys Glu
450                 455                 460
Ala Lys Tyr Tyr Gln Leu Arg Cys Ser Gly Pro Gly Leu Pro Leu Tyr
465                 470                 475                 480
Thr Leu His Ser Ser Val Asn Asp Lys Gly Leu Arg Val Leu Glu Asp
                485                 490                 495
Asn Ser Ala Leu Asp Lys Met Leu Gln Asn Val Gln Met Pro Ser Lys
                500                 505                 510
Lys Leu Asp Phe Ile Ile Leu Asn Glu Thr Lys Phe Trp Tyr Gln Met
                515                 520                 525
Ile Leu Pro Pro His Phe Asp Lys Ser Lys Lys Tyr Pro Leu Leu Leu
                530                 535                 540
Asp Val Tyr Ala Gly Pro Cys Ser Gln Lys Ala Asp Ile Val Phe Arg
545                 550                 555                 560
Leu Asn Trp Ala Thr Tyr Leu Ala Ser Thr Glu Asn Ile Ile Val Ala
                565                 570                 575
Ser Phe Asp Gly Arg Gly Ser Gly Tyr Gln Gly Asp Lys Ile Met His
                580                 585                 590
Ala Ile Asn Arg Arg Leu Gly Thr Phe Glu Val Glu Asp Gln Ile Glu
                595                 600                 605
```

-continued

Ala Ala Arg Gln Phe Ser Lys Met Gly Phe Val Asp Asn Lys Arg Ile
        610                 615                 620

Ala Ile Trp Gly Trp Ser Tyr Gly Tyr Val Thr Ser Met Val Leu
625                 630                 635                 640

Gly Ser Gly Ser Gly Val Phe Lys Cys Gly Ile Ala Val Ala Pro Val
                645                 650                 655

Ser Arg Trp Glu Tyr Tyr Glu Ser Val Tyr Thr Glu Arg Tyr Met Gly
                660                 665                 670

Leu Pro Thr Pro Glu Asp Asn Leu Asp His Tyr Arg Asn Ser Thr Val
                675                 680                 685

Met Ser Arg Ala Glu Asn Phe Lys Gln Val Glu Tyr Leu Leu Ile His
        690                 695                 700

Gly Thr Ala Asp Asp Asn Val His Phe Gln Ser Ala Gln Ile Ser
705                 710                 715                 720

Lys Ala Leu Val Asp Val Gly Val Asp Phe Gln Ala Met Trp Tyr Thr
                725                 730                 735

Asp Glu Asp His Gly Ile Ala Ser Ser Thr Ala His Gln His Ile Tyr
                740                 745                 750

Thr His Met Ser His Phe Ile Lys Gln Cys Phe Ser Leu Pro
        755                 760                 765

<210> SEQ ID NO 28
<211> LENGTH: 710
<212> TYPE: PRT
<213> ORGANISM: Flavobacterium sp.

<400> SEQUENCE: 28

Met Lys Lys Lys Ile Phe Ser Leu Leu Ser Ile Ala Val Val Ala Phe
1               5                   10                  15

His Gly Leu Ser Ala Gln Glu Ile Thr Leu Asp Lys Ile Tyr Ser Gly
                20                  25                  30

Gln Tyr Arg Ala Lys Gly Ile Ser Gly Ile Ala Ser Leu Asn Asp Gly
            35                  40                  45

Glu Asn Tyr Ala Thr Ile Glu Pro Thr Gly Ile Ala Lys Tyr Ser Tyr
    50                  55                  60

Lys Thr Ser Gln Lys Glu Lys Asn Ile Val Asp Gly Ser Phe Gln Gly
65                  70                  75                  80

Tyr Thr Phe Ser Asn Asp Glu Ser Lys Ile Leu Leu Gln Lys Ser Ser
                85                  90                  95

Gln Ser Ile Tyr Arg His Ser Phe Leu Gly Lys Phe Glu Val Lys Asp
            100                 105                 110

Leu Lys Ser Arg Thr Val Val Ser Leu Asn Asn Ala Asn Trp Ile Gln
        115                 120                 125

Glu Pro Lys Phe Ser Pro Asp Gly Ser Lys Val Ala Phe Ile Ala Asp
130                 135                 140

Asn Asn Leu Phe Tyr Gln Asp Leu Asn Thr Gly Lys Ile Thr Gln Ile
145                 150                 155                 160

Thr Thr Asp Gly Lys Lys Asn Glu Ile Ile Asn Gly Leu Gly Asp Trp
                165                 170                 175

Val Tyr Glu Glu Phe Gly His Ala Asp Tyr Gln Trp Asn Lys
            180                 185                 190

Ala Gly Asp Ala Leu Val Phe Val Arg Phe Asp Glu Arg Lys Val Pro
        195                 200                 205

Glu Ile Asn Ile Pro Ile Tyr Tyr Gln Asn Leu Tyr Pro Lys Leu Met

-continued

```
            210                 215                 220
Thr Tyr Lys Tyr Pro Lys Ala Gly Glu Glu Asn Ser Ala Val Thr Ala
225                 230                 235                 240

Tyr Leu Tyr Gln Leu Ser Ser Gly Lys Ser Ala Gln Leu Asn Phe Gly
                245                 250                 255

Ser Ser Glu Lys Tyr Tyr Ile Pro Gln Leu Phe Gln Thr Asn Ala Asn
                260                 265                 270

Asp Glu Ile Val Val Ala Thr Ala Asn Arg His Gln Asn Lys Val Asp
                275                 280                 285

Leu Leu Lys Val Asn Thr Lys Thr Ala Val Ser Lys Leu Phe Thr
290                 295                 300

Glu Thr Asp Asn Ala Trp Ile Glu Thr Asp Asn Leu Thr Met Glu Phe
305                 310                 315                 320

Leu Asp Asp Asn Ser Phe Leu Trp Ala Ser Glu Arg Asp Gly His Arg
                325                 330                 335

His Leu Tyr Trp Tyr Asp Ala Ala Gly Lys Leu Lys Lys Gln Val Ser
                340                 345                 350

Lys Gly Asp Trp Glu Ile Ile Asn Tyr Gly Tyr Asn Pro Lys Thr
                355                 360                 365

Lys Glu Val Tyr Ile Gln Thr Thr Glu Lys Gly Ser Ile Asn Lys Val
                370                 375                 380

Val Ser Lys Leu Asn Ile Asn Thr Gly Lys Thr Gln Leu Leu Ser Asn
385                 390                 395                 400

Ala Glu Gly Asn Asn Ser Ala Ala Phe Ser Lys Thr Phe Asn Tyr Phe
                405                 410                 415

Ile Asn Thr Ser Ser Thr Ala Lys Val Pro Thr Lys Tyr Ile Leu Lys
                420                 425                 430

Asp Ala Asn Gly Lys Asp Val Lys Glu Leu Gln Asn Asn Asp Asp Leu
                435                 440                 445

Leu Asn Lys Leu Lys Ser Asp Asn Phe Ile Ala Lys Glu Phe Ile Thr
                450                 455                 460

Ile Pro Asn Ala Ala Gly Asp Gln Met Asn Ala Trp Met Ile Lys Pro
465                 470                 475                 480

Lys Asn Phe Asp Pro Ala Lys Lys Tyr Pro Val Phe Met Phe Gln Tyr
                485                 490                 495

Ser Gly Pro Gly Ser Gln Gln Val Ala Asn Ser Trp Asp Gly Gly Asn
                500                 505                 510

Gly Ile Trp Phe Asp Met Leu Ala Gln Lys Gly Tyr Leu Val Val Cys
                515                 520                 525

Val Asp Gly Arg Gly Thr Gly Phe Arg Gly Thr Lys Tyr Lys Lys Val
530                 535                 540

Thr Tyr Lys Asn Leu Gly Lys Tyr Glu Ile Glu Asp Gln Ile Thr Ala
545                 550                 555                 560

Ala Lys Trp Leu Gly Asn Gln Ser Tyr Val Asp Lys Ser Arg Ile Gly
                565                 570                 575

Ile Phe Gly Trp Ser Tyr Gly Gly Tyr Met Ala Ser Leu Ala Met Thr
                580                 585                 590

Lys Gly Ala Asp Val Phe Lys Met Gly Ile Ala Val Ala Pro Val Thr
                595                 600                 605

Asn Trp Arg Phe Tyr Asp Ser Ile Tyr Thr Glu Arg Phe Leu Gln Thr
                610                 615                 620

Pro Gln Glu Asn Lys Asp Gly Tyr Asp Leu Asn Ser Pro Thr Thr Tyr
625                 630                 635                 640
```

-continued

```
Ala Lys Leu Leu Lys Gly Lys Phe Leu Leu Ile His Gly Thr Ala Asp
                645                 650                 655

Asp Asn Val His Phe Gln Asn Ser Met Glu Phe Ser Glu Ala Leu Ile
            660                 665                 670

Gln Asn Lys Lys Gln Phe Asp Phe Met Ala Tyr Pro Asp Lys Asn His
        675                 680                 685

Ser Ile Ile Gly Gly Asn Thr Arg Pro Gln Leu Tyr Glu Lys Met Thr
690                 695                 700

Asn Tyr Ile Leu Glu Asn
705                 710

<210> SEQ ID NO 29
<211> LENGTH: 723
<212> TYPE: PRT
<213> ORGANISM: Porphyromonas gingivalis

<400> SEQUENCE: 29

Met Lys Arg Pro Val Ile Ile Leu Leu Gly Ile Val Thr Met Cys
1               5                   10                  15

Ala Met Ala Gln Thr Gly Asn Lys Pro Val Asp Leu Lys Glu Ile Thr
            20                  25                  30

Ser Gly Met Phe Tyr Ala Arg Ser Ala Gly Ser Gly Ile Arg Ser Met
        35                  40                  45

Pro Asp Gly Glu His Tyr Thr Glu Met Asn Arg Glu Arg Thr Ala Ile
    50                  55                  60

Ile Arg Tyr Asn Tyr Ala Ser Gly Lys Ala Val Asp Thr Leu Phe Ser
65                  70                  75                  80

Val Glu Arg Ala Arg Glu Cys Pro Phe Lys Gln Ile Gln Asn Tyr Glu
                85                  90                  95

Val Ser Ser Thr Gly His His Ile Leu Leu Phe Thr Asp Met Glu Ser
            100                 105                 110

Ile Tyr Arg His Ser Tyr Arg Ala Ala Val Tyr Asp Tyr Asp Val Arg
        115                 120                 125

Arg Asn Leu Val Lys Pro Leu Ser Glu His Val Gly Lys Val Met Ile
    130                 135                 140

Pro Thr Phe Ser Pro Asp Gly Arg Met Val Ala Phe Val Arg Asp Asn
145                 150                 155                 160

Asn Ile Phe Ile Lys Lys Phe Asp Phe Asp Thr Glu Val Gln Val Thr
                165                 170                 175

Thr Asp Gly Gln Ile Asn Ser Ile Leu Asn Gly Ala Thr Asp Trp Val
            180                 185                 190

Tyr Glu Glu Glu Phe Gly Val Thr Asn Leu Met Ser Trp Ser Ala Asp
        195                 200                 205

Asn Ala Phe Leu Ala Phe Val Arg Ser Asp Glu Ser Ala Val Pro Glu
    210                 215                 220

Tyr Arg Met Pro Met Tyr Glu Asp Lys Leu Tyr Pro Glu Asp Tyr Thr
225                 230                 235                 240

Tyr Lys Tyr Pro Lys Ala Gly Glu Lys Asn Ser Thr Val Ser Leu His
                245                 250                 255

Leu Tyr Asn Val Ala Asp Arg Asn Thr Lys Ser Val Ser Leu Pro Ile
            260                 265                 270

Asp Ala Asp Gly Tyr Ile Pro Arg Ile Ala Phe Thr Asp Asn Ala Asp
        275                 280                 285

Glu Leu Ala Val Met Thr Leu Asn Arg Leu Gln Asn Asp Phe Lys Met
```

-continued

```
            290                 295                 300
Tyr Tyr Val His Pro Lys Ser Leu Val Pro Lys Leu Ile Leu Gln Asp
305                 310                 315                 320

Met Asn Lys Arg Tyr Val Asp Ser Asp Trp Ile Gln Thr Leu Lys Phe
                325                 330                 335

Thr Thr Gly Gly Gly Phe Ala Tyr Val Ser Glu Lys Asp Gly Phe Ala
                340                 345                 350

His Ile Tyr Leu Tyr Asp Asn Lys Gly Val Met His Arg Arg Ile Thr
                355                 360                 365

Ser Gly Asn Trp Asp Val Thr Lys Leu Tyr Gly Val Asp Ala Ser Gly
370                 375                 380

Thr Val Phe Tyr Gln Ser Ala Glu Glu Ser Pro Ile Arg Arg Ala Val
385                 390                 395                 400

Tyr Ala Ile Asp Ala Lys Gly Arg Lys Thr Lys Leu Ser Leu Asn Val
                405                 410                 415

Gly Thr Asn Asp Ala Leu Phe Ser Gly Asn Tyr Ala Tyr Ile Asn
                420                 425                 430

Thr Tyr Ser Ser Ala Ala Thr Pro Ala Val Val Ser Val Phe Arg Ser
        435                 440                 445

Lys Gly Ala Lys Glu Leu Arg Thr Leu Glu Asp Asn Val Ala Leu Arg
        450                 455                 460

Glu Arg Leu Lys Ala Tyr Arg Tyr Asn Pro Lys Glu Phe Thr Thr Ile
465                 470                 475                 480

Lys Thr Gln Ser Gly Leu Glu Leu Asn Ala Trp Ile Val Lys Pro Ile
                485                 490                 495

Asp Phe Asp Pro Ser Arg His Tyr Pro Val Leu Met Val Gln Tyr Ser
                500                 505                 510

Gly Pro Asn Ser Gln Gln Val Leu Asp Arg Tyr Ser Phe Asp Trp Glu
        515                 520                 525

His Tyr Leu Ala Ser Lys Gly Tyr Val Val Ala Cys Val Asp Gly Arg
        530                 535                 540

Gly Thr Gly Ala Arg Gly Glu Glu Trp Arg Lys Cys Thr Tyr Met Gln
545                 550                 555                 560

Leu Gly Val Phe Glu Ser Asp Asp Gln Ile Ala Ala Thr Ala Ile
                565                 570                 575

Gly Gln Leu Pro Tyr Val Asp Ala Ala Arg Ile Gly Ile Trp Gly Trp
                580                 585                 590

Ser Tyr Gly Gly Tyr Thr Thr Leu Met Ser Leu Cys Arg Gly Asn Gly
                595                 600                 605

Thr Phe Lys Ala Gly Ile Ala Val Ala Pro Val Ala Asp Trp Arg Phe
610                 615                 620

Tyr Asp Ser Val Tyr Thr Glu Arg Phe Met Arg Thr Pro Lys Glu Asn
625                 630                 635                 640

Ala Ser Gly Tyr Lys Met Ser Ser Ala Leu Asp Val Ala Ser Gln Leu
                645                 650                 655

Gln Gly Asn Leu Leu Ile Val Ser Gly Ser Ala Asp Asp Asn Val His
                660                 665                 670

Leu Gln Asn Thr Met Leu Phe Thr Glu Ala Leu Val Gln Ala Asn Ile
                675                 680                 685

Pro Phe Asp Met Ala Ile Tyr Met Asp Lys Asn His Ser Ile Tyr Gly
                690                 695                 700

Gly Asn Thr Arg Tyr His Leu Tyr Thr Arg Lys Ala Lys Phe Leu Phe
705                 710                 715                 720
```

Asp Asn Leu

<210> SEQ ID NO 30
<211> LENGTH: 732
<212> TYPE: PRT
<213> ORGANISM: Porphyromonas gingivalis

<400> SEQUENCE: 30

```
Met Lys Lys Thr Ile Phe Gln Gln Leu Phe Leu Ser Val Cys Ala Leu
  1               5                  10                  15

Thr Val Ala Leu Pro Cys Ser Ala Gln Ser Pro Glu Thr Ser Gly Lys
             20                  25                  30

Glu Phe Thr Leu Glu Gln Leu Met Pro Gly Gly Lys Glu Phe Tyr Asn
         35                  40                  45

Phe Tyr Pro Glu Tyr Val Val Gly Leu Gln Trp Met Gly Asp Asn Tyr
     50                  55                  60

Val Phe Ile Glu Gly Asp Asp Leu Val Phe Asn Lys Ala Asn Gly Lys
 65                  70                  75                  80

Ser Ala Gln Thr Thr Arg Phe Ser Ala Ala Asp Leu Asn Ala Leu Met
                 85                  90                  95

Pro Glu Gly Cys Lys Phe Gln Thr Thr Asp Ala Phe Pro Ser Phe Arg
            100                 105                 110

Thr Leu Asp Ala Gly Arg Gly Leu Val Val Leu Phe Thr Gln Gly Gly
        115                 120                 125

Leu Val Gly Phe Asp Met Leu Ala Arg Lys Val Thr Tyr Leu Phe Asp
130                 135                 140

Thr Asn Glu Glu Thr Ala Ser Leu Asp Phe Ser Pro Val Gly Asp Arg
145                 150                 155                 160

Val Ala Tyr Val Arg Asn His Asn Leu Tyr Ile Ala Arg Gly Gly Lys
                165                 170                 175

Leu Gly Glu Gly Met Ser Arg Ala Ile Ala Val Thr Ile Asp Gly Thr
            180                 185                 190

Glu Thr Leu Val Tyr Gly Gln Ala Val His Gln Arg Glu Phe Gly Ile
        195                 200                 205

Glu Lys Gly Thr Phe Trp Ser Pro Lys Gly Ser Cys Leu Ala Phe Tyr
    210                 215                 220

Arg Met Asp Gln Ser Met Val Lys Pro Thr Pro Ile Val Asp Tyr His
225                 230                 235                 240

Pro Leu Glu Ala Glu Ser Lys Pro Leu Tyr Tyr Pro Met Ala Gly Thr
                245                 250                 255

Pro Ser His His Val Thr Val Gly Ile Tyr His Leu Ala Thr Gly Lys
            260                 265                 270

Thr Val Tyr Leu Gln Thr Gly Glu Pro Lys Glu Lys Phe Leu Thr Asn
        275                 280                 285

Leu Ser Trp Ser Pro Asp Glu Asn Ile Leu Tyr Val Ala Glu Val Asn
    290                 295                 300

Arg Ala Gln Asn Glu Cys Lys Val Asn Ala Tyr Asp Ala Glu Thr Gly
305                 310                 315                 320

Arg Phe Val Arg Thr Leu Phe Val Glu Thr Asp Lys His Tyr Val Glu
                325                 330                 335

Pro Leu His Pro Leu Thr Phe Leu Pro Gly Ser Asn Asn Gln Phe Ile
            340                 345                 350

Trp Gln Ser Arg Arg Asp Gly Trp Asn His Leu Tyr Leu Tyr Asp Thr
        355                 360                 365
```

```
Thr Gly Arg Leu Ile Arg Gln Val Thr Lys Gly Glu Trp Glu Val Thr
        370                 375                 380

Asn Phe Ala Gly Phe Asp Pro Lys Gly Thr Arg Leu Tyr Phe Glu Ser
385                 390                 395                 400

Thr Glu Ala Ser Pro Leu Glu Arg His Phe Tyr Cys Ile Asp Ile Lys
                405                 410                 415

Gly Gly Lys Thr Lys Asp Leu Thr Pro Glu Ser Gly Met His Arg Thr
            420                 425                 430

Gln Leu Ser Pro Asp Gly Ser Ala Ile Ile Asp Ile Phe Gln Ser Pro
        435                 440                 445

Thr Val Pro Arg Lys Val Thr Val Thr Asn Ile Gly Lys Gly Ser His
        450                 455                 460

Thr Leu Leu Glu Ala Lys Asn Pro Asp Thr Gly Tyr Ala Met Pro Glu
465                 470                 475                 480

Ile Arg Thr Gly Thr Ile Met Ala Ala Asp Gly Gln Thr Pro Leu Tyr
                485                 490                 495

Tyr Lys Leu Thr Met Pro Leu His Phe Asp Pro Ala Lys Lys Tyr Pro
            500                 505                 510

Val Ile Val Tyr Val Tyr Gly Gly Pro His Ala Gln Leu Val Thr Lys
        515                 520                 525

Thr Trp Arg Ser Ser Val Gly Gly Trp Asp Ile Tyr Met Ala Gln Lys
        530                 535                 540

Gly Tyr Ala Val Phe Thr Val Asp Ser Arg Gly Ser Ala Asn Arg Gly
545                 550                 555                 560

Ala Ala Phe Glu Gln Val Ile His Arg Arg Leu Gly Gln Thr Glu Met
                565                 570                 575

Ala Asp Gln Met Cys Gly Val Asp Phe Leu Lys Ser Gln Ser Trp Val
            580                 585                 590

Asp Ala Asp Arg Ile Gly Val His Gly Trp Ser Tyr Gly Gly Phe Met
        595                 600                 605

Thr Thr Asn Leu Met Leu Thr His Gly Asp Val Phe Lys Val Gly Val
        610                 615                 620

Ala Gly Gly Pro Val Ile Asp Trp Asn Arg Tyr Glu Ile Met Tyr Gly
625                 630                 635                 640

Glu Arg Tyr Phe Asp Ala Pro Gln Glu Asn Pro Glu Gly Tyr Asp Ala
                645                 650                 655

Ala Asn Leu Leu Lys Arg Ala Gly Asp Leu Lys Gly Arg Leu Met Leu
            660                 665                 670

Ile His Gly Ala Ile Asp Pro Val Val Trp Gln His Ser Leu Leu
        675                 680                 685

Phe Leu Asp Ala Cys Val Lys Ala Arg Thr Tyr Pro Asp Tyr Tyr Val
        690                 695                 700

Tyr Pro Ser His Glu His Asn Val Met Gly Pro Asp Arg Val His Leu
705                 710                 715                 720

Tyr Glu Thr Ile Thr Arg Tyr Phe Thr Asp His Leu
                725                 730

<210> SEQ ID NO 31
<211> LENGTH: 67
<212> TYPE: PRT
<213> ORGANISM: Porphyromonas gingivalis

<400> SEQUENCE: 31

Val Asp Ala Asp Arg Ile Gly Val His Gly Trp Ser Tyr Gly Gly Phe
```

-continued

```
                1               5                  10                    15
Met Thr Arg Leu Met Leu Ile His Gly Ala Ile Asp Pro Val Val
                       20                  25                  30

Trp Gln His Ser Leu Leu Phe Leu Asp Ala Cys Val Lys Ala Arg Thr
                       35                  40                  45

Tyr Pro Asp Tyr Tyr Val Tyr Pro Ser His Glu His Asn Val Met Gly
                  50                  55                  60

Pro Asp Arg
 65
```

<210> SEQ ID NO 32
<211> LENGTH: 68
<212> TYPE: PRT
<213> ORGANISM: Porphyromonas gingivalis

<400> SEQUENCE: 32

```
Val Asp Ala Ala Arg Ile Gly Ile Trp Gly Trp Ser Tyr Gly Gly Tyr
 1               5                  10                    15

Thr Thr Asn Leu Leu Ile Val Ser Gly Ser Ala Asp Asp Asn Val His
                       20                  25                  30

Leu Gln Asn Thr Met Leu Phe Thr Glu Ala Leu Val Gln Ala Asn Ile
                       35                  40                  45

Pro Phe Asp Met Ala Ile Tyr Met Asp Lys Asn His Ser Ile Tyr Gly
                  50                  55                  60

Gly Asn Thr Arg
 65
```

<210> SEQ ID NO 33
<211> LENGTH: 68
<212> TYPE: PRT
<213> ORGANISM: Porphyromonas gingivalis

<400> SEQUENCE: 33

```
Val Asp Pro Asp Arg Ile Ala Ile Tyr Gly Ala Ser His Gly Gly Tyr
 1               5                  10                    15

Ala Thr Pro Leu Phe Val Val Gln Gly Ala Asn Asp Pro Arg Val Asn
                       20                  25                  30

Ile Asn Glu Ser Asp Gln Ile Val Thr Ala Leu Arg Ala Arg Gly Phe
                       35                  40                  45

Glu Val Pro Tyr Met Val Lys Tyr Asn Glu Gly His Gly Phe His Arg
                  50                  55                  60

Glu Glu Asn Ser
 65
```

<210> SEQ ID NO 34
<211> LENGTH: 68
<212> TYPE: PRT
<213> ORGANISM: Porphyromonas gingivalis

<400> SEQUENCE: 34

```
Val Asn Gly Lys Lys Val Gly Cys Phe Gly Ala Ser Tyr Gly Gly Phe
 1               5                  10                    15

Met Thr Pro Leu Leu Leu Leu His Gly Ser Val Asp Thr Asn Val Pro
                       20                  25                  30

Thr Ala Glu Ser Val Asn Leu Tyr Asn Ala Leu Lys Ile Leu Gly Arg
                       35                  40                  45

Glu Val Glu Phe Ile Glu Phe Thr Glu Gln Asp His Phe Ile Leu Glu
                  50                  55                  60
```

```
Pro Glu Arg Arg
 65

<210> SEQ ID NO 35
<211> LENGTH: 68
<212> TYPE: PRT
<213> ORGANISM: Porphyromonas gingivalis

<400> SEQUENCE: 35

Val Asp Gly Asp Arg Ile Gly Ala Val Gly Ala Ser Tyr Gly Gly Phe
 1               5                  10                  15

Ser Val Pro Ile Leu Met Ile His Gly Glu Leu Asp Phe Arg Ile Leu
            20                  25                  30

Ala Ser Gln Ala Met Ala Ala Phe Asp Ala Ala Gln Leu Arg Gly Val
        35                  40                  45

Pro Ser Glu Met Leu Ile Tyr Pro Asp Glu Asn His Trp Val Leu Gln
    50                  55                  60

Pro Gln Asn Ala
 65

<210> SEQ ID NO 36
<211> LENGTH: 51
<212> TYPE: DNA
<213> ORGANISM: Artificial Sequence
<220> FEATURE:
<223> OTHER INFORMATION: Description of Artificial Sequence: probe

<400> SEQUENCE: 36
ttcgatccgg caaagaaata tcctgttatt gtctatgttt acggaggacc t            51

<210> SEQ ID NO 37
<211> LENGTH: 48
<212> TYPE: DNA
<213> ORGANISM: Artificial Sequence
<220> FEATURE:
<223> OTHER INFORMATION: Description of Artificial Sequence: probe

<400> SEQUENCE: 37
gtggatgccg atagaatagg agtacatggc tggagctatg gtggcttt                48

<210> SEQ ID NO 38
<211> LENGTH: 2199
<212> TYPE: DNA
<213> ORGANISM: Porphyromonas gingivalis

<400> SEQUENCE: 38
atgaagaaga caatcttcca acaactattt ctgtctgttt gtgcccttac agtggccttg      60
ccttgttcgg ctcagtctcc tgaaacgagt ggtaaggagt ttactcttga gcaactgatg     120
cccggaggaa aagagtttta aactttttac cccgaatacg tggtcggttt gcaatggatg     180
ggagacaatt atgtctttat cgagggtgat gatttagttt ttaataaggc gaatggcaaa     240
tcggctcaga cgaccagatt ttctgctgcc gatctcaatg cactcatgcc ggagggatgc     300
aaatttcaga cgactgatgc tttcccttca ttccgcacac tcgatgccgg acggggactg     360
gtcgttctat ttacccaagg aggattagtc ggattcgata tgcttgctcg aaaggtgact     420
tatcttttcg ataccaatga ggagacggct tcttggatt tttctcctgt gggagaccgt     480
gttgcctatg tcagaaacca taacctttac attgctcgtg gaggtaaatt gggagaaggt     540
atgtcacgag ctatcgctgt gactatcgat ggaactgaga ctctcgtata tggccaggcc     600
```

```
gtacaccagc gtgaattcgg tatcgaaaaa ggtacattct ggtctccaaa agggagctgc    660
cttgctttct atcgaatgga tcagagtatg gtgaagccta ccccgatagt ggattatcat    720
ccgctcgaag ccgagtccaa accgctttat taccccatgg caggtactcc gtcacaccac    780
gttacggttg ggatctatca tctggccaca ggtaagaccg tctatctaca aacgggtgaa    840
cccaaggaaa aatttctgac gaatttgagt tggagtccgg acgaaaatat cttgtatgta    900
gctgaggtga atcgtgctca aaacgaatgt aaggtaaatg cctatgacgc tgagaccggt    960
agattcgtcc gtacgctttt tgttgaaacc gataaacatt atgtagagcc gttacatccc   1020
ctgacattcc ttccgggaag taacaatcag ttcatttggc agagccgtcg cgacggatgg   1080
aaccatctct atctgtatga tactacaggt cgtctgatcc gtcaggtgac aaaaggggag   1140
tgggaggtta caaactttgc aggcttcgat cccaagggaa cacggctcta tttcgaaagt   1200
accgaagcca gccctctcga cgccattttt tactgtattg atatcaaagg aggaaagaca   1260
aaagatctga ctccggagtc gggaatgcac cgcactcagc tatctcctga tggttctgcc   1320
ataatcgata ttttttcagtc acctactgtc ccgcgtaagg ttacagtgac aaatatcggc   1380
aaagggtctc acacactctt ggaggctaag aaccccgata cgggctatgc catgccggag   1440
atcagaacgg gtaccatcat ggcggccgat gggcagacac ctctttatta caagctcacg   1500
atgccgcttc atttcgatcc ggcaaagaaa tatcctgtta ttgtctatgt ttacggagga   1560
cctcatgccc aactcgtaac caagacatgg cgcagctctg tcggtggatg ggatatctat   1620
atggcacaga aaggctatgc cgtctttacg gtggatagtc gcggatctgc caatagaggg   1680
gctgctttcg agcaggttat tcatcgtcgt ttggggcaga ccgagatggc cgatcagatg   1740
tgcggtgtgg atttcctcaa gagccaatca tgggtggatg ccgatagaat aggagtacat   1800
ggctggagct atggtggctt tatgactacg aatctgatgc ttacgcacgg cgatgtcttc   1860
aaagtcggag tagccggcgg gcctgtcata gactggaatc gatatgagat tatgtacggt   1920
gagcgttatt tcgatgcgcc acaggaaaat cccgaaggat acgatgctgc caacctgctc   1980
aaacgagccg gtgatctgaa aggacgactt atgctgattc atggagcgat cgatccggtc   2040
gtggtatggc agcattcact ccttttcctt gatgcttgcg tgaaggcacg cacctatcct   2100
gactattacg tctatccgag ccacgaacat aatgtgatgg ggccggacag agtacatttg   2160
tatgaaacaa taacccgtta tttcacagat cacttatga                          2199
```

<210> SEQ ID NO 39
<211> LENGTH: 6
<212> TYPE: PRT
<213> ORGANISM: Artificial Sequence
<220> FEATURE:
<223> OTHER INFORMATION: Description of Artificial Sequence: consensus
      sequence
<221> NAME/KEY: VARIANT
<222> LOCATION: (2)
<223> OTHER INFORMATION: Any amino acid
<221> NAME/KEY: VARIANT
<222> LOCATION: (4)
<223> OTHER INFORMATION: Any amino acid
<221> NAME/KEY: VARIANT
<222> LOCATION: (5)
<223> OTHER INFORMATION: Any amino acid

<400> SEQUENCE: 39

Gly Xaa Ser Xaa Xaa Gly
 1               5

<210> SEQ ID NO 40

```
<211> LENGTH: 6
<212> TYPE: PRT
<213> ORGANISM: Artificial Sequence
<220> FEATURE:
<223> OTHER INFORMATION: Description of Artificial Sequence: consensus
      sequence
<221> NAME/KEY: VARIANT
<222> LOCATION: (2)
<223> OTHER INFORMATION: Any amino acid
<221> NAME/KEY: VARIANT
<222> LOCATION: (4)
<223> OTHER INFORMATION: Any amino acid

<400> SEQUENCE: 40

Gly Xaa Ser Xaa Gly Gly
 1               5

<210> SEQ ID NO 41
<211> LENGTH: 4
<212> TYPE: PRT
<213> ORGANISM: Artificial Sequence
<220> FEATURE:
<223> OTHER INFORMATION: Description of Artificial Sequence: A specific
      substrate for a prolyl-tripeptidyl peptidase
<221> NAME/KEY: VARIANT
<222> LOCATION: (1)
<223> OTHER INFORMATION: A natural or modified amino acid
<221> NAME/KEY: VARIANT
<222> LOCATION: (2)
<223> OTHER INFORMATION: A natural or modified amino acid
<221> NAME/KEY: VARIANT
<222> LOCATION: (4)
<223> OTHER INFORMATION: A natural or modified amino acid except proline

<400> SEQUENCE: 41

Xaa Xaa Pro Xaa
 1

<210> SEQ ID NO 42
<211> LENGTH: 676
<212> TYPE: PRT
<213> ORGANISM: Porphyromonas gingivalis

<400> SEQUENCE: 42

Met Pro Asp Gly Glu His Tyr Thr Glu Met Asn Arg Glu Arg Thr Ala
 1               5                  10                  15

Ile Ile Arg Tyr Asn Tyr Ala Ser Gly Lys Ala Val Asp Thr Leu Phe
                20                  25                  30

Ser Val Glu Arg Ala Arg Glu Cys Pro Phe Lys Gln Ile Gln Asn Tyr
         35                  40                  45

Glu Val Ser Ser Thr Gly His His Ile Leu Leu Phe Thr Asp Met Glu
     50                  55                  60

Ser Ile Tyr Arg His Ser Tyr Arg Ala Ala Val Tyr Asp Tyr Asp Val
 65                  70                  75                  80

Arg Arg Asn Leu Val Lys Pro Leu Ser Glu His Val Gly Lys Val Met
                 85                  90                  95

Ile Pro Thr Phe Ser Pro Asp Gly Arg Met Val Ala Phe Val Arg Asp
            100                 105                 110

Asn Asn Ile Phe Ile Lys Lys Phe Asp Phe Asp Thr Glu Val Gln Val
        115                 120                 125

Thr Thr Asp Gly Gln Ile Asn Ser Ile Leu Asn Gly Ala Thr Asp Trp
    130                 135                 140

Val Tyr Glu Glu Glu Phe Gly Val Thr Asn Leu Met Ser Trp Ser Ala
145                 150                 155                 160
```

```
Asp Asn Ala Phe Leu Ala Phe Val Arg Ser Asp Glu Ser Ala Val Pro
                165                 170                 175

Glu Tyr Arg Met Pro Met Tyr Glu Asp Lys Leu Tyr Pro Glu Asp Tyr
            180                 185                 190

Thr Tyr Lys Tyr Pro Lys Ala Gly Glu Lys Asn Ser Thr Val Ser Leu
        195                 200                 205

His Leu Tyr Asn Val Ala Asp Arg Asn Thr Lys Ser Val Ser Leu Pro
    210                 215                 220

Ile Asp Ala Asp Gly Tyr Ile Pro Arg Ile Ala Phe Thr Asp Asn Ala
225                 230                 235                 240

Asp Glu Leu Ala Val Met Thr Leu Asn Arg Leu Gln Asn Asp Phe Lys
                245                 250                 255

Met Tyr Tyr Val His Pro Lys Ser Leu Val Pro Lys Leu Ile Leu Gln
            260                 265                 270

Asp Met Asn Lys Arg Tyr Val Asp Ser Asp Trp Ile Gln Thr Leu Lys
        275                 280                 285

Phe Thr Thr Gly Gly Gly Phe Ala Tyr Val Ser Glu Lys Asp Gly Phe
    290                 295                 300

Ala His Ile Tyr Leu Tyr Asp Asn Lys Gly Val Met His Arg Arg Ile
305                 310                 315                 320

Thr Ser Gly Asn Trp Asp Val Thr Lys Leu Tyr Gly Val Asp Ala Ser
                325                 330                 335

Gly Thr Val Phe Tyr Gln Ser Ala Glu Glu Ser Pro Ile Arg Arg Ala
            340                 345                 350

Val Tyr Ala Ile Asp Ala Lys Gly Arg Lys Thr Lys Leu Ser Leu Asn
        355                 360                 365

Val Gly Thr Asn Asp Ala Leu Phe Ser Gly Asn Tyr Ala Tyr Tyr Ile
    370                 375                 380

Asn Thr Tyr Ser Ser Ala Ala Thr Pro Ala Val Val Ser Val Phe Arg
385                 390                 395                 400

Ser Lys Gly Ala Lys Glu Leu Arg Thr Leu Glu Asp Asn Val Ala Leu
                405                 410                 415

Arg Glu Arg Leu Lys Ala Tyr Arg Tyr Asn Pro Lys Glu Phe Thr Thr
            420                 425                 430

Ile Lys Thr Gln Ser Gly Leu Glu Leu Asn Ala Trp Ile Val Lys Pro
        435                 440                 445

Ile Asp Phe Asp Pro Ser Arg His Tyr Pro Val Leu Met Val Gln Tyr
450                 455                 460

Ser Gly Pro Asn Ser Gln Gln Val Leu Asp Arg Tyr Ser Phe Asp Trp
465                 470                 475                 480

Glu His Tyr Leu Ala Ser Lys Gly Tyr Val Val Ala Cys Val Asp Gly
                485                 490                 495

Arg Gly Thr Gly Ala Arg Gly Glu Glu Trp Arg Lys Cys Thr Tyr Met
            500                 505                 510

Gln Leu Gly Val Phe Glu Ser Asp Gln Ile Ala Ala Ala Thr Ala
        515                 520                 525

Ile Gly Gln Leu Pro Tyr Val Asp Ala Ala Arg Ile Gly Ile Trp Gly
    530                 535                 540

Trp Ser Tyr Gly Gly Tyr Thr Thr Leu Met Ser Leu Cys Arg Gly Asn
545                 550                 555                 560

Gly Thr Phe Lys Ala Gly Ile Ala Val Ala Pro Val Ala Asp Trp Arg
                565                 570                 575

Phe Tyr Asp Ser Val Tyr Thr Glu Arg Phe Met Arg Thr Pro Lys Glu
```

-continued

```
                580                 585                 590
Asn Ala Ser Gly Tyr Lys Met Ser Ala Leu Asp Val Ala Ser Gln
            595                 600                 605
Leu Gln Gly Asn Leu Leu Ile Val Ser Gly Ser Ala Asp Asp Asn Val
        610                 615                 620
His Leu Gln Asn Thr Met Leu Phe Thr Glu Ala Leu Val Gln Ala Asn
625                 630                 635                 640
Ile Pro Phe Asp Met Ala Ile Tyr Met Asp Lys Asn His Ser Ile Tyr
                645                 650                 655
Gly Gly Asn Thr Arg Tyr His Leu Tyr Thr Arg Lys Ala Lys Phe Leu
            660                 665                 670
Phe Asp Asn Leu
        675

<210> SEQ ID NO 43
<211> LENGTH: 541
<212> TYPE: PRT
<213> ORGANISM: Porphyromonas gingivalis

<400> SEQUENCE: 43

Met Asp Lys Gly Gly Asn Glu Asn Tyr His Leu Phe Ala Ser Asn Ile
1               5                   10                  15
Asp Gly Ser Asn Thr Arg Asp Leu Thr Pro Phe Asp Gly Val Lys Ala
            20                  25                  30
Ser Ile Leu Asn Met Leu Lys Glu Gln Lys Asp Tyr Met Ile Ile Ser
        35                  40                  45
Met Asn Lys Asn Asn Pro Gln Ile Phe Glu Pro Tyr Lys Leu Asn Val
    50                  55                  60
Val Thr Gly Glu Leu Thr Gln Leu Tyr Glu Asn Lys Asp Ala Ala Asn
65                  70                  75                  80
Pro Ile Gln Gly Tyr Glu Phe Asp Lys Asp Gly Glu Leu Arg Gly Tyr
                85                  90                  95
Ser Arg Leu Val Asn Gly Ile Glu Ser Glu Leu Tyr Tyr Lys Asp Leu
            100                 105                 110
Ala Thr Gly Glu Phe Arg Leu Leu Lys Lys Thr His Trp Asp Asp Thr
        115                 120                 125
Phe Gly Val Ile Ala Phe Asn Tyr Ala Ser Lys Asn Lys Asp Glu Ala
    130                 135                 140
Tyr Val Leu Thr Asn Leu Asp Ser Asp Lys Thr Arg Ile Val Leu Tyr
145                 150                 155                 160
Asp Leu Lys Gln Asn Lys Ile Ile Arg Glu Ile Phe Ala Asn Glu Asp
                165                 170                 175
Tyr Asp Val Ser Gly Leu His Leu Ser Arg Lys Arg Asn Tyr Glu Ile
            180                 185                 190
Asp Leu Met Ala Tyr Glu Gly Glu Lys Ser Val Val Pro Val Ser
        195                 200                 205
Ala Thr Tyr Lys Glu Leu His Lys Leu Met Glu Lys Glu Phe Lys Gly
    210                 215                 220
Lys Glu Phe Ser Val Val Asp Tyr Asp Asp Glu Thr Ile Leu Leu
225                 230                 235                 240
Ile Ala Val Gln Ser Asp Lys Leu Tyr Gly Thr Tyr Tyr Gln Phe Asp
                245                 250                 255
Thr Arg Thr Lys Lys Phe Thr Leu Leu Tyr Asp Leu Met Pro Gln Leu
            260                 265                 270
```

```
Lys Glu Glu Asp Met Ala Glu Met Arg Pro Ile Lys Phe Lys Ser Arg
            275                 280                 285

Asp Gly Leu Thr Ile His Gly Phe Ile Thr Leu Pro Lys Ala Ala Leu
        290                 295                 300

Glu Gly Lys Lys Val Pro Leu Ile Val Asn Pro His Gly Gly Pro Gln
305                 310                 315                 320

Gly Ile Arg Asp Ser Trp Gly Phe Asn Pro Glu Thr Gln Leu Phe Ala
                325                 330                 335

Ser Arg Gly Tyr Ala Thr Leu Gln Val Asn Phe Arg Ile Ser Gly Gly
            340                 345                 350

Tyr Gly Lys Glu Phe Leu Arg Ala Gly Phe Lys Gln Ile Gly Arg Lys
        355                 360                 365

Ala Met Asp Asp Val Glu Asp Gly Val Arg Tyr Ala Ile Ser Gln Gly
    370                 375                 380

Trp Val Asp Pro Asp Arg Ile Ala Ile Tyr Gly Ala Ser His Gly Gly
385                 390                 395                 400

Tyr Ala Thr Leu Met Gly Leu Val Lys Thr Pro Asp Leu Tyr Ala Cys
                405                 410                 415

Gly Val Asp Tyr Val Gly Val Ser Asn Ile Tyr Thr Phe Phe Asp Ser
            420                 425                 430

Phe Pro Glu Tyr Trp Lys Pro Phe Lys Glu Met Val Lys Glu Ile Trp
        435                 440                 445

Tyr Asp Leu Asp Asn Pro Glu Glu Ala Ala Ile Ala Lys Glu Val Ser
    450                 455                 460

Pro Phe Phe Gln Ile Asp Lys Ile Asn Lys Pro Leu Phe Val Val Gln
465                 470                 475                 480

Gly Ala Asn Asp Pro Arg Val Asn Ile Asn Glu Ser Asp Gln Ile Val
                485                 490                 495

Thr Ala Leu Arg Ala Arg Gly Phe Glu Val Pro Tyr Met Val Lys Tyr
            500                 505                 510

Asn Glu Gly His Gly Phe His Arg Glu Glu Asn Ser Met Glu Leu Tyr
        515                 520                 525

Arg Ala Met Leu Gly Phe Phe Ala Lys His Leu Lys Lys
    530                 535                 540

<210> SEQ ID NO 44
<211> LENGTH: 841
<212> TYPE: PRT
<213> ORGANISM: Porphyromonas gingivalis

<400> SEQUENCE: 44

Met Lys Lys Ser Leu Leu Met Leu Leu Leu Ser Ala Ala Thr Leu Ser
1               5                   10                  15

Ser Ile Glu Ala Gln Thr Ile Gln Gln Met Lys Ala Gly Gly Pro Trp
            20                  25                  30

Pro Val Arg Ala Ala Phe Lys Thr Asp Thr Val Gly Met Asn Gly Ser
        35                  40                  45

Lys Tyr Asn Pro Ala Asp Leu Leu Arg Gln Ala Tyr Asp Ala Thr Asp
    50                  55                  60

Lys Asp Leu Arg Asn Val Ser Ala Asp Lys Asp Gly Arg Ile Ala Gly
65                  70                  75                  80

Arg Lys Ala Gly Ser Lys Ala Glu Arg Ser Glu Met Ala Val Tyr Ser
                85                  90                  95

Phe Ala Leu Thr Ala Glu His Phe Ala Lys Ala Asp Ile Glu Val Phe
            100                 105                 110
```

```
Gly Gln Gly Arg Met Ser Leu Trp Leu Asp Asp Lys Gln Ile Gly Ile
    115                 120                 125

Ala Asp Ser Pro Asn Ser Lys Gly Asp Thr Thr Leu Arg Phe Ser Ala
130                 135                 140

Ser Leu Ser Leu Val Pro Gly Thr His Leu Leu Leu Lys Ser Leu
145                 150                 155                 160

Leu Leu Glu Gly Asp Thr Thr Ala Thr Asp Val Arg Val Leu Lys
                165                 170                 175

Pro Lys Thr Ala Arg Asp Ser Ser Ala Leu Tyr Pro Asn Tyr Thr Gly
            180                 185                 190

Lys Glu Arg Leu Ser Leu Lys His Met Met Ser Gly Thr Phe Leu Ser
        195                 200                 205

Gly Gly Ser Leu Ser Pro Thr Gly Lys Tyr Val Leu Thr Ser Tyr Arg
        210                 215                 220

Val Ser Arg Asp Asn Lys Pro Ala Val Thr Tyr Asn Gln Leu Arg Asp
225                 230                 235                 240

Ala Lys Gly Asn Ile Leu Leu Asn Leu Asn Glu Lys Glu Ala Leu Gly
                245                 250                 255

Trp Met Pro His Glu Asp Met Leu Met Val Ile Arg Lys Glu Gly Asn
            260                 265                 270

Ala Lys Arg Leu Val Ala Phe Asp Pro Met Gly Lys Gly Glu Lys Thr
        275                 280                 285

Leu Val Ser Asn Leu Pro Glu Ser Gln Phe Arg Met Ser Pro Asp Ala
    290                 295                 300

Arg Tyr Tyr Leu Phe Tyr Lys Gln Glu Lys Gly Pro Gly Lys Asp Pro
305                 310                 315                 320

Leu Phe Ile Arg His Leu Asp Pro Asp Asp Arg Gln Ser Asp Trp Arg
                325                 330                 335

Asp Arg Ser Gln Ile Tyr Leu Leu Asn Ala Glu Ser Gly Val Tyr Gly
            340                 345                 350

Pro Leu Thr Phe Gly Tyr Ser Thr Thr Tyr Ile Tyr Asp Ile Ala Pro
        355                 360                 365

Asp Ser Lys Arg Ala Leu Ile Gly Thr Leu Ser Thr Asp Trp Thr Arg
370                 375                 380

Arg Pro Phe Arg Phe Ala Thr Ile Met Glu Tyr Asn Met Glu Thr Gly
385                 390                 395                 400

Lys Ala Asp Thr Leu Ile Thr Arg Asp Pro Ser Ile Asp Ala Ile Gln
                405                 410                 415

Tyr Thr Pro Asp Gly Lys His Leu Ile Val Met Gly Ser Ala Asp Ala
            420                 425                 430

Phe Gly Asn Ile Gly Leu Asn Leu Lys Ser Gly Val Thr Pro Asn Ser
        435                 440                 445

Tyr Asp Lys Gln Phe Phe Leu Phe Asp Leu Ser Thr Arg Lys Ala Thr
    450                 455                 460

Ala Leu Thr Lys Asn Phe Asn Pro Ser Val Ser Ala Gly Arg Phe Asp
465                 470                 475                 480

Arg Lys Asn Asn Tyr Tyr Phe Arg Ala Glu Asn Gly Ser Arg Lys
                485                 490                 495

Gln Leu Tyr Arg Leu Asp Leu Lys Thr Leu Glu Ile Ser Gln Ile Gln
            500                 505                 510

Thr Gly Glu Asp Val Val Gln Trp Phe Gly Val Ala Ala Asp Asn Gly
        515                 520                 525
```

-continued

```
Ala Val Trp Tyr Ser Gly Gln Ser Ala Asn Asn Ala Asp Arg Leu Tyr
        530                 535                 540

Arg Leu Asp Gly Thr Lys Gly Lys Leu Val Trp Asp Leu Ser Ala Glu
545                 550                 555                 560

Lys Leu Ala Asn Ile Asp Phe Thr Pro Ala Arg Asp Trp Asn Tyr Thr
                565                 570                 575

Ala Pro Asp Gly Thr Val Val Glu Gly Trp Tyr Tyr Leu Pro Pro Gln
            580                 585                 590

Phe Asp Pro Ser Lys Lys Tyr Pro Met Leu Val Tyr Tyr Gly Gly
        595                 600                 605

Thr Ser Pro Ile Asn Arg Thr Leu Glu Gly His Tyr Ser Leu Ala Met
    610                 615                 620

Tyr Ala Ala Gln Gly Tyr Val Val Tyr Thr Leu Asn Pro Ser Gly Thr
625                 630                 635                 640

Thr Gly Tyr Gly Gln Glu Tyr Ala Ala Arg His Val Asn Ala Trp Gly
                645                 650                 655

Asp Arg Thr Ala Asp Glu Ile Ile Gly Ala Thr Lys Glu Phe Ile Arg
            660                 665                 670

Thr His Ser Phe Val Asn Gly Lys Lys Val Gly Cys Phe Gly Ala Ser
        675                 680                 685

Tyr Gly Gly Phe Met Thr Gln Tyr Leu Gln Thr Lys Thr Asp Ile Phe
690                 695                 700

Ala Ala Ala Val Ser His Ala Gly Ile Ser Ser Ile Ser Asn Tyr Trp
705                 710                 715                 720

Gly Ser Gly Tyr Trp Gly Met Gly Tyr Ser Thr Val Ala Ser Thr Asp
                725                 730                 735

Ser Tyr Pro Trp Asn Asn Pro Asp Leu Tyr Ala Gly His Ser Pro Leu
            740                 745                 750

Phe Arg Ala Asp Lys Ile His Thr Pro Leu Leu Leu His Gly Ser
        755                 760                 765

Val Asp Thr Asn Val Pro Thr Ala Glu Ser Val Asn Leu Tyr Asn Ala
770                 775                 780

Leu Lys Ile Leu Gly Arg Glu Val Glu Phe Ile Glu Phe Thr Glu Gln
785                 790                 795                 800

Asp His Phe Ile Leu Glu Pro Glu Arg Arg Ile Arg Trp Thr Asn Ser
                805                 810                 815

Ile Cys Ala Trp Phe Ala Arg Trp Leu Gln Asp Asp Pro Thr Trp Trp
            820                 825                 830

Asn Glu Leu Tyr Pro Pro Val Asn Leu
        835                 840
```

<210> SEQ ID NO 45
<211> LENGTH: 684
<212> TYPE: PRT
<213> ORGANISM: Porphyromonas gingivalis

<400> SEQUENCE: 45

```
Met Asn Lys Lys Ile Phe Ser Met Met Ala Ala Ser Ile Ile Gly Ser
1               5                  10                  15

Ala Ala Met Thr Pro Ser Ala Gly Thr Asn Thr Gly Glu His Leu Thr
            20                  25                  30

Pro Glu Leu Phe Met Thr Leu Ser Arg Val Ser Glu Met Ala Leu Ser
        35                  40                  45

Pro Asp Gly Lys Thr Ala Val Tyr Ala Val Ser Phe Pro Asp Val Lys
    50                  55                  60
```

-continued

```
Thr Asn Lys Ala Thr Arg Glu Leu Phe Thr Val Asn Leu Asp Gly Ser
 65                  70                  75                  80

Gly Arg Lys Gln Ile Thr Asp Thr Glu Ser Asn Glu Tyr Ala Pro Ala
                 85                  90                  95

Trp Met Ala Asp Gly Lys Arg Ile Ala Phe Met Ser Asn Glu Gly Gly
            100                 105                 110

Ser Met Gln Leu Trp Val Met Asn Ala Asp Gly Thr Glu Arg Arg Gln
        115                 120                 125

Leu Ser Asn Ile Glu Gly Gly Ile Thr Gly Phe Leu Phe Ser Pro Asp
130                 135                 140

Glu Lys Gln Val Leu Phe Thr Lys Asp Ile Lys Phe Gly Lys Arg Thr
145                 150                 155                 160

Lys Asp Ile Tyr Pro Asp Leu Asp Lys Ala Thr Gly Arg Ile Ile Thr
                165                 170                 175

Asp Leu Met Tyr Lys His Trp Asp Glu Trp Val Glu Thr Ile Pro His
            180                 185                 190

Pro Phe Ile Ala Asn Ala Thr Asp Gly Met Ile Thr Thr Gly Lys Asp
        195                 200                 205

Ile Met Glu Gly Glu Pro Tyr Glu Ala Pro Met Lys Pro Trp Ser Gly
210                 215                 220

Ile Glu Asp Phe Ser Trp Ser Pro Asp Gly Gln Asn Ile Ala Tyr Ala
225                 230                 235                 240

Ser Arg Lys Lys Thr Gly Met Ala Tyr Ser Leu Ser Thr Asn Ser Asp
                245                 250                 255

Ile Tyr Ile Tyr Asn Leu Ala Ser Gly Arg Thr His Asn Ile Ser Glu
            260                 265                 270

Gly Met Met Gly Tyr Asp Thr Tyr Pro Lys Phe Ser Pro Asp Gly Lys
        275                 280                 285

Ser Ile Ala Trp Ile Ser Met Glu Arg Asp Gly Tyr Glu Ser Asp Leu
290                 295                 300

Lys Arg Leu Phe Val Ala Asp Leu Ala Thr Gly Lys Arg Thr His Val
305                 310                 315                 320

Asn Pro Thr Phe Asp Tyr Asn Val Asp Met Ile Gln Trp Ala Pro Asp
                325                 330                 335

Ser Lys Gly Ile Tyr Phe Leu Ala Cys Lys Glu Ala Glu Thr Asn Leu
            340                 345                 350

Trp Glu Ile Thr Leu Lys Thr Gly Lys Ile Arg Gln Ile Thr Gln Gly
        355                 360                 365

Gln His Asp Tyr Ala Asp Phe Ser Val Arg Asn Asp Val Met Leu Ala
370                 375                 380

Lys Arg His Ser Phe Glu Leu Pro Asp Asp Leu Tyr Arg Val Asn Leu
385                 390                 395                 400

Lys Asn Gly Ala Ala Gln Ala Val Thr Ala Glu Asn Lys Val Ile Leu
                405                 410                 415

Asp Arg Leu Thr Pro Ile Thr Cys Glu Lys Arg Trp Met Lys Thr Thr
            420                 425                 430

Asp Gly Gly Asn Met Leu Thr Trp Val Val Leu Pro Pro Asn Phe Asp
        435                 440                 445

Lys Asn Lys Lys Tyr Pro Ala Ile Leu Tyr Cys Gln Gly Gly Pro Gln
450                 455                 460

Asn Thr Val Ser Gln Phe Trp Ser Phe Arg Trp Asn Leu Arg Leu Met
465                 470                 475                 480
```

-continued

Ala Glu Gln Gly Tyr Ile Val Ile Ala Pro Asn Arg His Gly Val Pro
                485                 490                 495

Gly Phe Gly Gln Lys Trp Asn Glu Gln Ile Ser Gly Asp Tyr Gly Gly
            500                 505                 510

Gln Asn Met Arg Asp Tyr Leu Thr Ala Val Asp Glu Met Lys Lys Glu
        515                 520                 525

Pro Tyr Val Asp Gly Asp Arg Ile Gly Ala Val Gly Ala Ser Tyr Gly
    530                 535                 540

Gly Phe Ser Val Tyr Trp Leu Ala Gly His His Asp Lys Arg Phe Ala
545                 550                 555                 560

Ala Phe Ile Ala His Ala Gly Ile Phe Asn Leu Glu Met Gln Tyr Ala
                565                 570                 575

Thr Thr Glu Glu Met Trp Phe Ala Asn Trp Asp Ile Gly Gly Pro Phe
            580                 585                 590

Trp Glu Lys Asp Asn Val Val Ala Gln Arg Thr Tyr Ala Thr Ser Pro
        595                 600                 605

His Lys Phe Val Gln Asn Trp Asp Thr Pro Ile Leu Met Ile His Gly
    610                 615                 620

Glu Leu Asp Phe Arg Ile Leu Ala Ser Gln Ala Met Ala Ala Phe Asp
625                 630                 635                 640

Ala Ala Gln Leu Arg Gly Val Pro Ser Glu Met Leu Ile Tyr Pro Asp
                645                 650                 655

Glu Asn His Trp Val Leu Gln Pro Gln Asn Ala Leu Leu Phe His Arg
            660                 665                 670

Thr Phe Phe Gly Trp Leu Asp Arg Trp Leu Lys Lys
        675                 680

<210> SEQ ID NO 46
<211> LENGTH: 8
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 46

Ser Pro Tyr Ser Ser Asp Thr Thr
  1               5

<210> SEQ ID NO 47
<211> LENGTH: 16
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 47

Ala Pro Val Arg Ser Leu Asn Cys Thr Leu Arg Asp Ser Gln Gln Lys
  1               5                  10                  15

<210> SEQ ID NO 48
<211> LENGTH: 25
<212> TYPE: PRT
<213> ORGANISM: Porphyromonas gingivalis

```
<400> SEQUENCE: 48

His Ser Tyr Arg Ala Ala Val Tyr Asp Tyr Asp Val Arg Arg Asn Leu
  1               5                  10                  15

Val Lys Pro Leu Ser Glu His Val Gly
             20              25
```